(12) United States Patent
Jaszai

(10) Patent No.: US 6,591,429 B1
(45) Date of Patent: *Jul. 15, 2003

(54) PHYSICAL PROTECTOR

(75) Inventor: Zoltan Kazmer Jaszai, Tokyo (JP)

(73) Assignee: Burlington Consolidated Limited Incorporation, Dublin (IE)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/930,192

(22) PCT Filed: Apr. 30, 1996

(86) PCT No.: PCT/JP96/01186
§ 371 (c)(1),
(2), (4) Date: Oct. 15, 1997

(87) PCT Pub. No.: WO96/34220
PCT Pub. Date: Oct. 31, 1996

(30) Foreign Application Priority Data

Apr. 28, 1995 (JP) .............................................. 7-106381
Jul. 12, 1995 (JP) .............................................. 7-176478

(51) Int. Cl.[7] .............................................. A41D 13/00
(52) U.S. Cl. ........................ 2/455; 251/335.2; 251/331; 251/339; 5/706; 5/654
(58) Field of Search ........................... 2/455, 413, 414; 36/29; 251/335.2, 331, 339; 137/223; 5/706, 708, 713, 654

(56) References Cited

U.S. PATENT DOCUMENTS

| | | | | |
|---|---|---|---|---|
| 2,566,576 A | * | 9/1951 | Marsh | 137/223 |
| 2,589,716 A | * | 3/1952 | Marsh | 137/223 |
| 2,604,297 A | * | 7/1952 | Winstead | 137/223 |
| 2,942,614 A | * | 6/1960 | Lardner | 137/223 |
| 2,949,927 A | * | 8/1960 | Mackal | 137/223 |
| 3,433,455 A | * | 3/1969 | Cook | 251/321 |
| 3,864,766 A | * | 2/1975 | Prete, Jr. | 5/337 |
| 4,966,185 A | * | 10/1990 | Schram | 137/223 |
| 5,031,246 A | * | 7/1991 | Kronenberger | 2/197 |
| 5,074,765 A | * | 12/1991 | Pekar | 417/480 |
| 5,113,599 A | * | 5/1992 | Cohen et al. | 36/88 |
| 5,158,767 A | * | 10/1992 | Cohen et al. | 36/88 |
| 5,315,715 A | * | 5/1994 | Kronenberger | 2/183 |
| 5,344,437 A | * | 9/1994 | Pistay | 607/109 |
| 5,372,487 A | * | 12/1994 | Pekar | 417/480 |
| 5,406,661 A | * | 4/1995 | Pekar | 5/454 |
| 5,588,227 A | * | 12/1996 | Goldston et al. | 36/93 |
| 6,012,188 A | * | 1/2000 | Daniels et al. | 5/654 |

* cited by examiner

*Primary Examiner*—Michael A. Neas
(74) *Attorney, Agent, or Firm*—Wenderoth, Lind & Ponack, L.L.P.

(57) ABSTRACT

A physical protector has a bag member (10) formed of gas-barrier seal members (1,2) different in deformability, and a valve (a) by which an air passage is formed by exerting a pushing force to the seal members (1,2) to elastically deform the seal members and closed by releasing the pushing force to resume the original shape of the seal members. The physical protector is attached to physical parts such as the human trunk or limbs and inflated by operating the valve (a) to introduce air into the bag member (10), thus protecting the physical parts. Since the air can be arbitrarily introduced into or discharged from the bag member by operating the valve (a), the protector can be used repeatedly. The valve (a) is made flat and compact so as not to give the user an unpleasant feeling.

43 Claims, 71 Drawing Sheets

PHYSICAL PROTECTOR

TECHNICAL FIELD

This invention relates to a physical protector having an inflatable bag member with a small and simple vent valve which can be fittingly worn on or around various parts of the human body to conveniently protect them.

BACKGROUND ART

A variety of physical protectors for protecting the parts of the human body, including the trunk, arms and legs, have been used in medical, sports and other various fields.

One of the physical protectors is a chest pad formed by covering a pad base formed of elastic material such as foamed urethane, and has a curved surface fit for the chest with a soft material such as cloth. This chest pad has a commonly acceptable size so as to be generally fitted to a human's chest with an average physique.

On the other hand, an elastic supporter which is formed by weaving elastic strings into a cylindrical texture of a befitting length is used for protecting the arms and legs. Since differences among individuals in sizes of the human's wrist, arm and ankle are not noticeable, preparation of at least three supporters of large, medium and small sizes may suffice for every person.

Thus, it may be useful to prepare physical protectors of different sizes fit for every person different in physique. However, the irrationality of having many protectors of different sizes ready for various users has been pointed out.

Furthermore, the size and shape of the chest pad as noted above are not completely conformable to those individuals different in physique. Therefore, when the chest pad of this sort is put on the chest of a man with his clothes on, it will be uncomfortable to wear in most cases. Although the chest pad has generally the pad base as a core formed of elastic material such as foamed urethane, it cannot be closely fitted to the chests of all men, and therefore every man does not always feel comfortable and cannot be protected completely.

The inventor of the present invention has proposed arm and finger protective holders each formed of a bag-shaped flat wrapping member in Japanese Patent Application Disclosure No. HEI 6-239268(A). The flat wrapping member of the proposed holder is provided with a vent valve and inflated with air introduced through the vent valve in a state wound around the arm or finger, thus protecting the arm or finger.

The vent valve on the wrapping member of the aforesaid holder is formed by boring a small hole in a membrane of the wrapping member and sealing the hole with an adhesive seal upon introducing air into the bag-shaped wrapping member through the hole. However, the vent valve of this structure makes it impossible to subtly control the expansion of the wrapping member. Moreover, the adhesive seal is used with the intention of using the holder repeatedly, but the vent valve can neither endure repeated use nor discharge the air efficiently.

In general, the vent valve of this type has a complicated structure including a valve body for performing the opening and closing operations and a spring member for urging the valve body in one direction. Thus, this complicated vent valve mounted on the protective device entails a structural disadvantage such that it makes the protective device complicated and bulky, although the protective device itself should be simple in structure and easy to handle.

A simple check valve may possibly be assembled in an air pipe to form another vent valve. However, the vent valve also makes the protective device thick and bulky, and besides, it is too hard to wear comfortably.

SUMMERY OF THE INVENTION

The present invention was made to remedy the drawbacks suffered by the conventional physical protectors mentioned above and has an object of providing a physical protector which is simple and compact in structure, has excellent durability, and is provided with a vent valve capable of performing selective introduction and release of air.

Another object of the present invention is to provide a physical protector which can be conformably fitted to an object to be protected, thereby suitably protecting the object.

Still another object of the present invention is to provide a physical protector capable of effectively protecting not only the human body and limbs, but also various articles and commodities.

To attain the objects described above according to the present invention, there is provided a physical protector comprising gas-barrier seal members which are different in deformability, a valve which is opened by elastically deforming the seal members with a pushing force to form an air passage and closed by releasing the pushing force to resume the original shape of the seal members, thus closing the air passage, and a bag member formed of sheet-like gas-barrier membranes so as to be attached to the human body or limbs. The valve is mounted onto the bag member so as to open or close the bag member.

The valve is opened by utilizing the deformability of the seal members to thereby let air in the bag member through the air passage, thus inflating the bag member with the air. The bag member thus inflated is worn on a part of the human body. When the valve resumes its original shape, the air passage is closed. Therefore, by controlling the pushing force exerted on the seal members, the inflation of the bag member can be regulated to the desired condition. The discharge of the air from the bag member is accomplished by pressing the seal members to open the air passage and then pressing the bag member.

The seal members may be made of soft and rigid seal materials. Since two soft and rigid seal members of different kinds are different in deformability, a void is defined between the seal members to open the air passage when elastically deforming the seal members and closed when elastically restoring the seal members due to the difference in deformability between the soft and rigid seal members.

The soft seal member noted above may be made of a film sheet, and the rigid seal member may be made of a thick sheet having a desired thickness. The seal members have vent holes at different positions, respectively, and are laid one on top of another and closely in surface contact with each other. Thus, the void through which the vent holes formed at different positions in the seal members are connected is defined between the rigid and soft seal members to secure the air passage. Since the rigid and soft seal members are laminated as noted above, the air passage assumes its closed state under a normal condition, thus fulfilling the function of a valve.

As another way, on the top of an elastically deformable rigid member having a spherical surface with a central protrusion, a soft member having a similar spherical surface may be closely placed, thus constituting the seal members. With this structure in which the soft seal member is elastically supported by the central protrusion of the rigid seal member, the air passage defined between the seal members can be securely sealed.

Otherwise, the soft seal member may have a vent hole in its central portion, and the rigid seal member may have a vent hole in its peripheral portion. In this embodiment, by depressing the rigid seal member with a pointed tool or the like through the central vent hole in the soft seal member, the void is formed between the seal members to enlarge the air passage. By pulling out the pointed tool, the rigid seal member regains its original shape, thereby closing the vent hole bored in the peripheral portion of the rigid seal member. Thus, the function of a valve can be fulfilled as well.

The soft seal member may be provided with elongated vent holes extending from the central portion toward the peripheral portion of the seal member, and the vent hole formed in the rigid seal member may be located apart from the elongated vent holes. With this structure, by depressing the portion of the soft seal member in which one of the elongated vent holes is formed with a finger, a void is formed between the soft seal member and the rigid seal member. Simultaneously, the remaining elongated vent holes formed in the portions of the soft seal member to which the depressing force is not applied are open to form air passages. When the depressing force is released, the peripheral portion of the rigid soft member first elastically restores its original shape to cause the peripheral portion of the rigid seal member in which the vent holes are formed to be brought into intimate contact with the soft seal member, consequently fulfilling the function of a valve.

The rigid seal member may be provided with a support column extending downward from the lower surface of the rigid seal member. By depressing the rigid seal member, the bag member is pushed down through the support column to widen the opening of the bag member.

The soft seal member may have a substantially H-shaped vertical cross section so as to serve as a valve body to be set in a fitting hole which is formed in the rigid seal member as a sleeve-like valve seat. The valve body is elastically deformed to secure the air passage between itself and the fitting hole in the valve seat. According to this, the soft seal member is elastically deformed to form the air passage between the soft seal member and the rigid valve seat.

Or again, the soft seal member may have a substantially H-shaped vertical cross section so as to serve as a valve body to be set in a fitting hole which is formed in the rigid seal member as a sleeve-like valve seat. The valve body is elastically deformed by operating a rotary press means to secure the air passage between itself and the fitting hole in the valve seat. With this embodiment, by rotating the rotary press means to depress the soft valve body, the soft seal member is elastically deformed to form the air passage between the soft seal member and the rigid valve seat.

As a countermeasure, the rigid seal member may have a substantially H-shaped vertical cross section so as to serve as a valve body to be set in a fitting hole which is formed in the soft seal member as a sleeve-like valve seat. The valve body is elastically deformed to secure the air passage between itself and the fitting hole in the valve seat. According to this, the rigid seal member is elastically deformed to form the air passage between the rigid seal member and the soft valve seat.

The soft seal member may be formed into a valve body having a tapered base portion so as to have a substantially H-shaped vertical cross section as a whole, and the rigid seal member may be formed into a sleeve-like valve seat having a tapered fitting hole. By depressing the valve body to slide the valve body, an air passage is formed between the base portion of the valve body and the fitting hole of the valve seat. According to this, by sliding the valve body along the tapered face on the fitting hole of the valve seat, a void is formed between the valve body and the fitting hole of the valve seat, and by bringing the valve body and the valve seat into close contact with each other, sealing between the fitting hole and the base portion can be achieved.

The soft seal member may be provided with a pump for pressurizing fluid in the air passage. Furthermore, a watertight cap may be disposed on a part of the seal member to increases the water resisting property of the bag member.

DETAILED DESCRIPTION OF THE PREFERRED EMBODIMENTS

The embodiments of a physical protector according to this invention will be described hereinafter with reference to the accompanying drawings.

Figure 1:
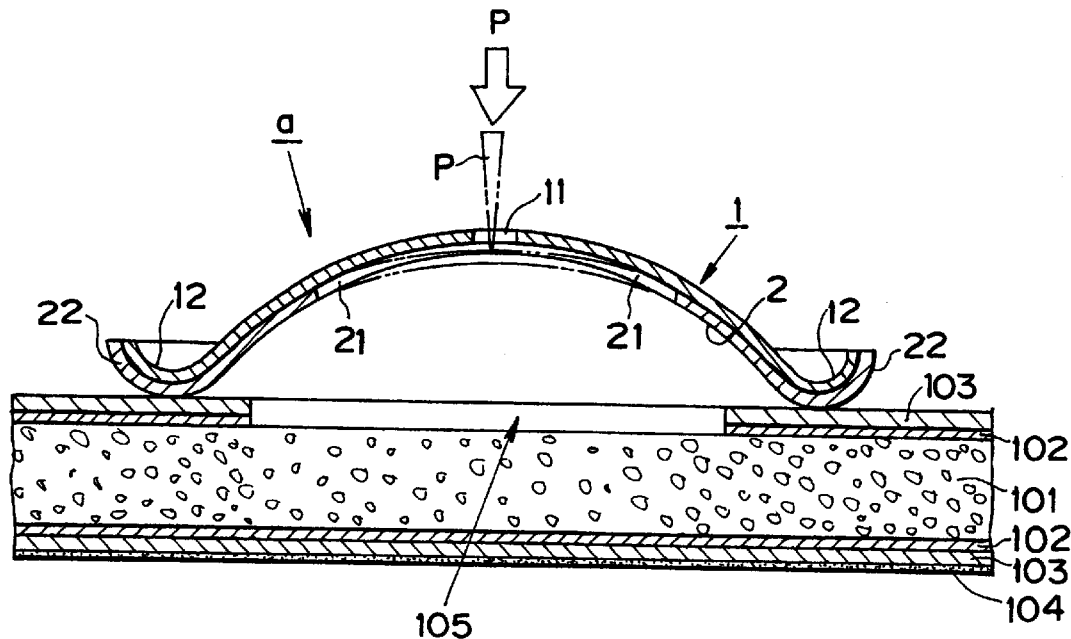
FIG. 1 is a sectional view showing a first embodiment of a valve of a physical protector according to this invention.
Figure 2:
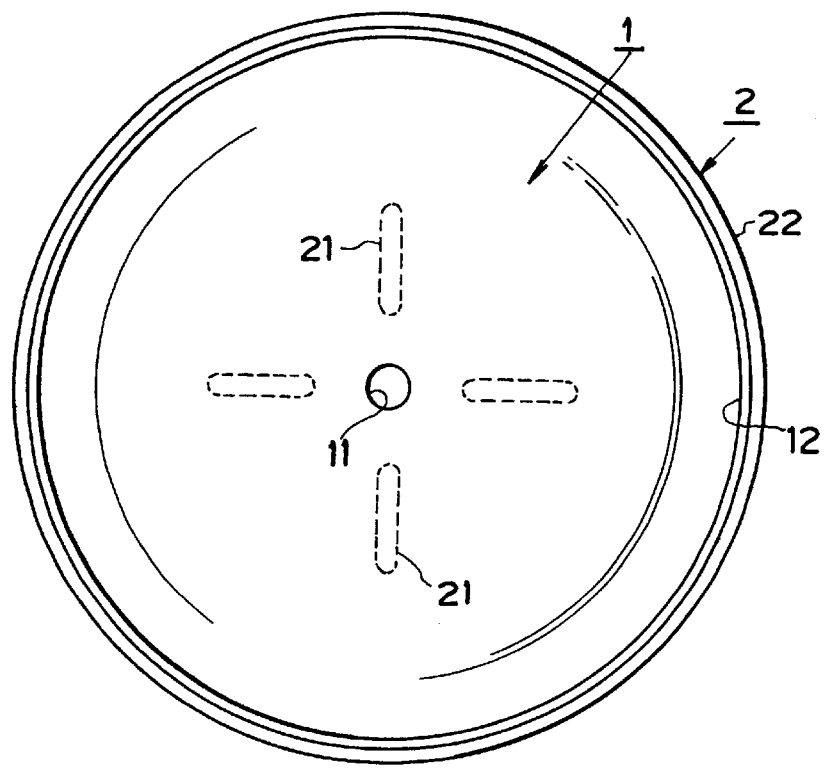
FIG. 2 is a plan view of the valve of FIG. 1.
Figure 3:
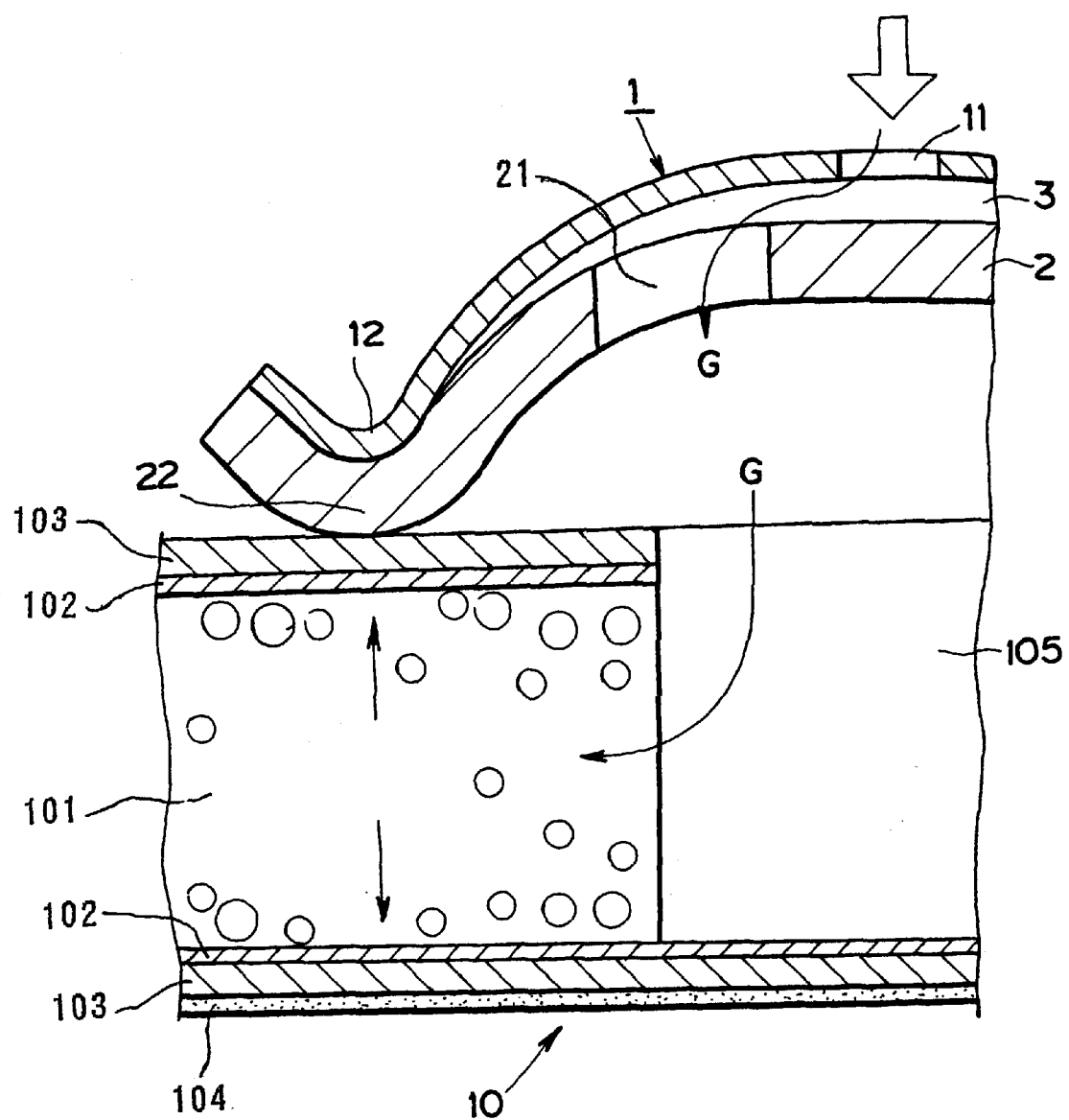
FIG. 3 is an enlarged operational view of a principal portion of FIG. 1.

FIG. 1 through FIG. 3 shows a first embodiment of a valve provided on the physical protector according to this invention.

The valve a in this embodiment comprises one seal member 1 which is relatively soft and thin and has a spherical surface, and another seal member 2 which is relatively rigid and thick and overlaid in layers with the soft seal member. Both seal members 1 and 2 are made of gas-barrier sheet material, i.e. synthetic resin such as silicone and polypropylene, and artificial or natural rubber. The layered seal members are made by vacuum forming in the form of a spherical protrusion and have an elastic recovery property with respect to a depressing force. It is desirable that one seal member 1 has a thickness of about 0.01 mm to 1 mm, and the other seal member 2 has a thickness of about 0.5 mm to 3 mm.

The seal members 1 and 2 have vent holes 11 and 21 which are placed at different positions so as to close each other when the seal members are laminated. The surfaces of the laminated seal members 1 and 2 are desired to be planished so as to be brought into intimate contact with each other with great strength.

The vent hole 11 is formed in a round shape in one seal member 1 to allow fluid G such as air to pass therethrough and placed at the center of the seal member. The seal member 1 has a curved peripheral rim 12. The elongated vent holes 21 are formed radially in the seal member 2 and slightly displaced from the center toward the periphery of the seal member. The seal member 2 has a curved peripheral rim 22. Both seal members 1 and 2 are bonded along the rims 12 and 22 to a bag member 10 by high-frequency welding or with adhesive, but the surfaces except the rims 12 and 22 are not intimately sealed and in mere contact with each other.

According to this embodiment, both seal members 1 and 2 made of the respective materials as noted above are different in elastic recovery property. Thus, one seal member 1 is airtightly bonded with the other seal member 2, so that the vent holes 11 and 21 are stopped by the intimately connected seal members 1 and 2.

By inserting a pin-like tool into the vent hole 11 of one seal member 1 to depress the other seal member 2 as shown in FIG. 3, the other seal member 2 is deformed, but the seal member 1 is little deformed. As a result, an air passage 3 is secured between both seal members 1 and 2 to allow the fluid G to flow into or out of the bag member 10 through an opening 105. Likewise, when releasing the depressing force exerted on the laminated seal members 1 and 2, the air passage 3 is formed therebetween due to the difference in elastic deformability between the seal members.

Therefore, although the valve thus constructed is very simple and compact, the air passage 3 for the fluid G can be reliably opened or closed. Furthermore, since the laminated seal members 1 and 2 are not embrittled even if they are repeatedly deformed, the valve excels in durability. Besides, the rims 12 and 22 of the both seal members 1 and 2 bring about the effect of maintaining the shape of the overall valve and function as a stopper for retaining the valve on various devices.

The rims 12 and 22 are basically provided on the valve of the first embodiment, but are not absolutely necessary to this invention. Although not shown in the accompanying drawings, the portions corresponding to the rims of the seal members may be flat and confronted by the bag member 10 to widen the area on which the bag member 10 and the valve a are disposed. Moreover, the number and shape of the vent holes 11 and 21 are by no means limitative as long as the vent holes formed in the respective seal members do not coincide with each other.

Figure 4:
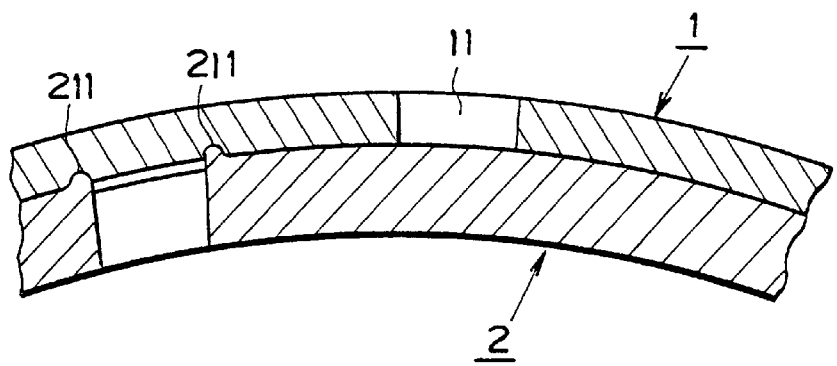
FIG. 4 is an enlarged view showing a principal portion of a second embodiment of a valve of a physical protector according to this invention.
Figure 5:
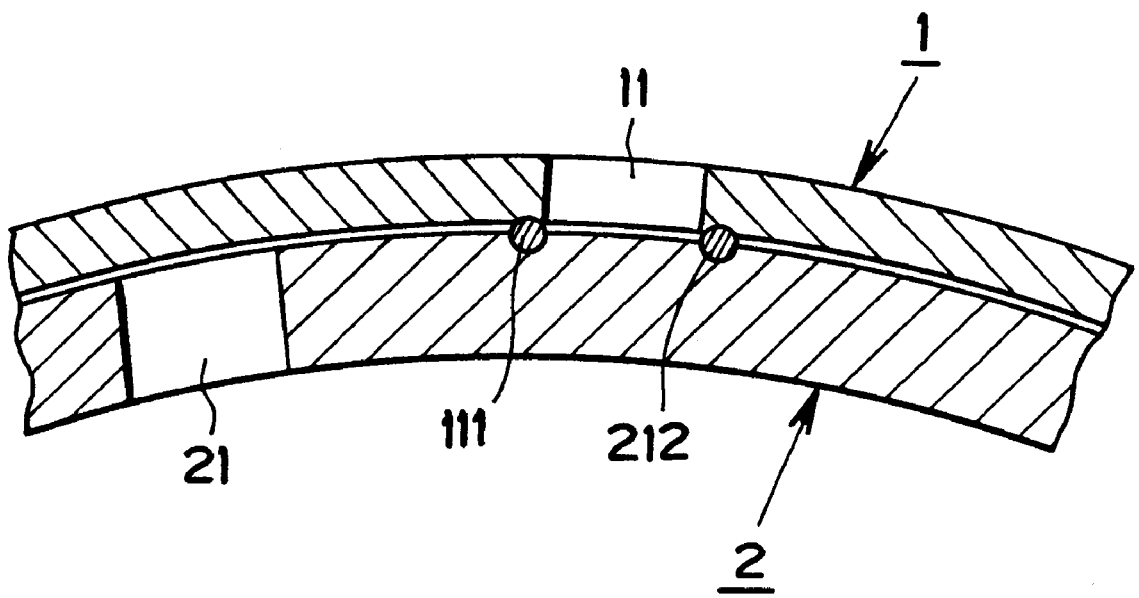
FIG. 5 is a sectional view showing a modified form of FIG. 4.

FIG. 4 and FIG. 5 show a second embodiment of a valve for use in a physical protector of the present invention.

On one of the mating surfaces of the laminated seal members 1 and 2, an annular small ridge 211 is formed. The small ridge in the illustrated embodiment is formed around the vent hole 21 bored in the seal member 2. In this embodiment, the mating surfaces of the seal members are in close contact with each other to mutually close the vent holes in an ordinary state. However, when the vent holes are opened to let in the air or the like, the mating surfaces of the seal members can easily be separated to widen the air passage due to the small ridge 211, thereby facilitating the flowing of air or the like. Though not shown, the small ridge may be formed on the mating surface of the seal member 1 around the vent hole 11.

Instead of the aforenoted small ridge 211, a combination of an O-ring 111 and an O-ring receiving groove 212 can be used as shown in FIG. 5. The O-ring 111 is bonded to the periphery of the vent hole 11 of the seal member 1 with adhesive. The O-ring receiving groove 212 is formed in the portion of the other seal member 2, which is opposite to the vent hole 11.

Figure 6:
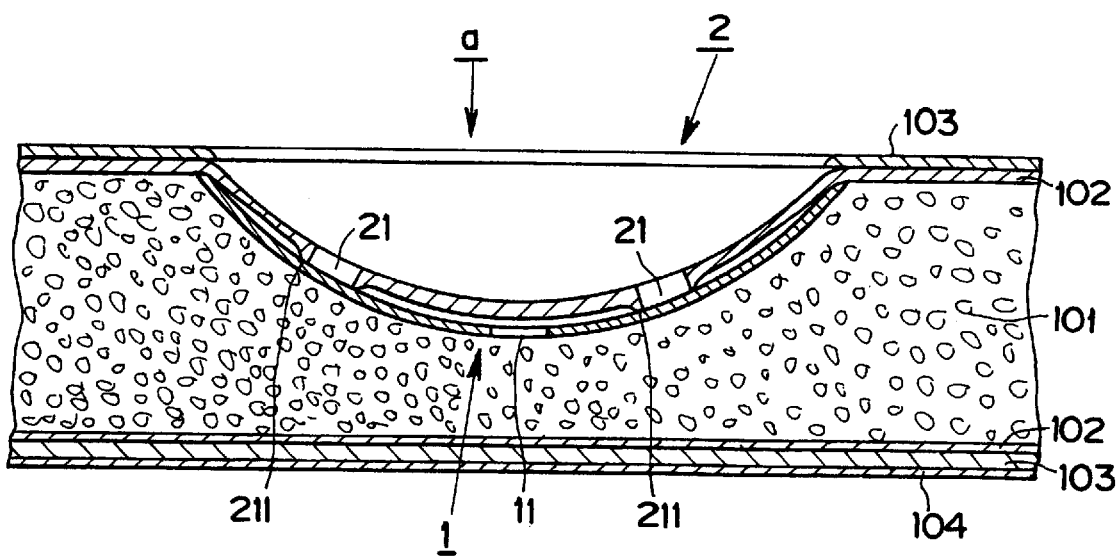
FIG. 6 is a sectional view showing a third embodiment of a valve of a physical protector according to this invention.

FIG. 6 shows a third embodiment of a valve assembled in a physical protector according to this invention, in which the shape relation between the seal members is reverse to the first and second embodiments.

The valve a in this embodiment subsides in the bag member 10 so as not to form a protrusion on the bag member 10. According to such a valve structure, the protector can be worn without feeling an unpleasant sensation.

Figure 7:
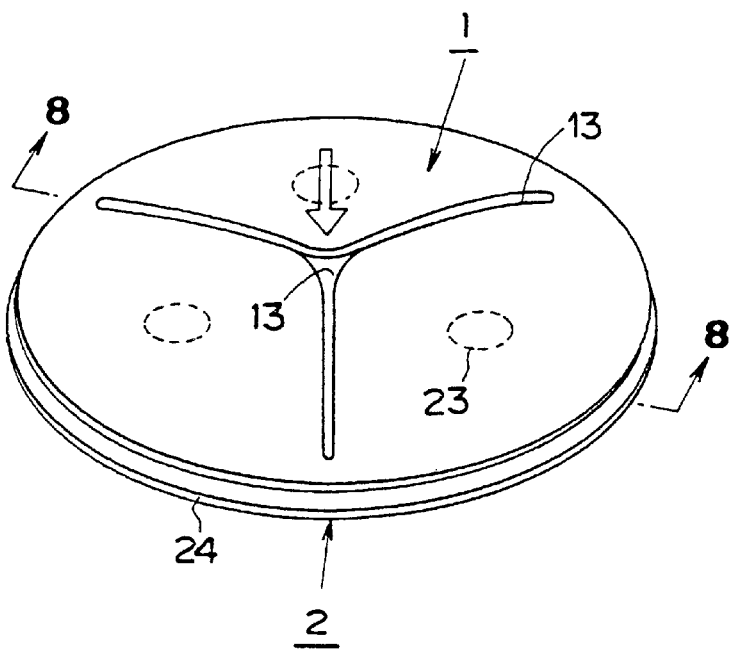
FIG. 7 is a sectional view showing a fourth embodiment of a valve of a physical protector according to this invention.
Figure 8:
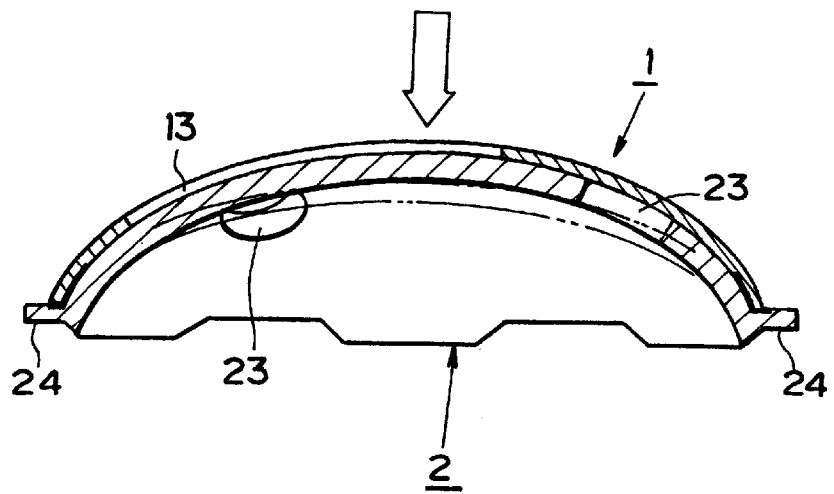
FIG. 8 is a section taken on line 8—8 in FIG. 7.
Figure 9:
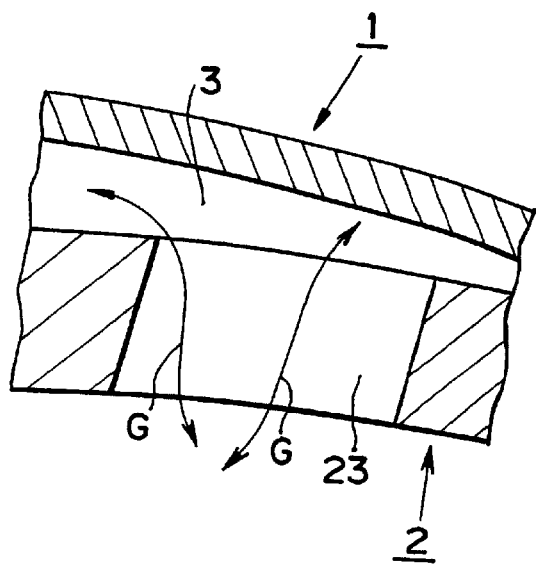
FIG. 9 is an enlarged operational view of a principal portion of FIG. 8.

FIG. 7 through FIG. 9 shows a fourth embodiment of a valve for use in a physical protector of the invention.

The seal member 1 has split-shaped vent holes 13 extending radially from the center toward the periphery of the seal member. Although the vent holes 13 in this embodiment extend in three radial directions, the number of the vent holes and the direction in which the vent holes extend are not limitative. The other seal member 2 has round vent holes 23 placed at positions displaced from the center of the seal member 1 and the split-shaped vent holes 13 formed in the seal member 1. The seal member 2 further has a flange 24. This flange 24 extends vertically outward from the peripheral edge of the seal member.

According to this embodiment having the aforesaid structure, the vent holes 13 and 23 are mutually closed with the seal members similarly to the first embodiment. By pushing down one tongue piece formed between the adjacent vent holes 13 of the seal member 1, an air passage 3 is formed between the other tongue pieces of the seal member 1 and the seal member 2 which is depressed with the tongue piece pushed down, as shown in FIG. 8 and FIG. 9, thus permitting fluid G to pass therethrough.

This embodiment brings about other operations and effects similar to those brought about by the first embodiment. The flange 24 of the seal member 2 has the effect of maintaining the shape of the overall valve. As a countermeasure, it is possible to form the vent holes 23 in the seal member 1 and the split-shaped vent holes 13 in the other seal member 2.

Figure 10:
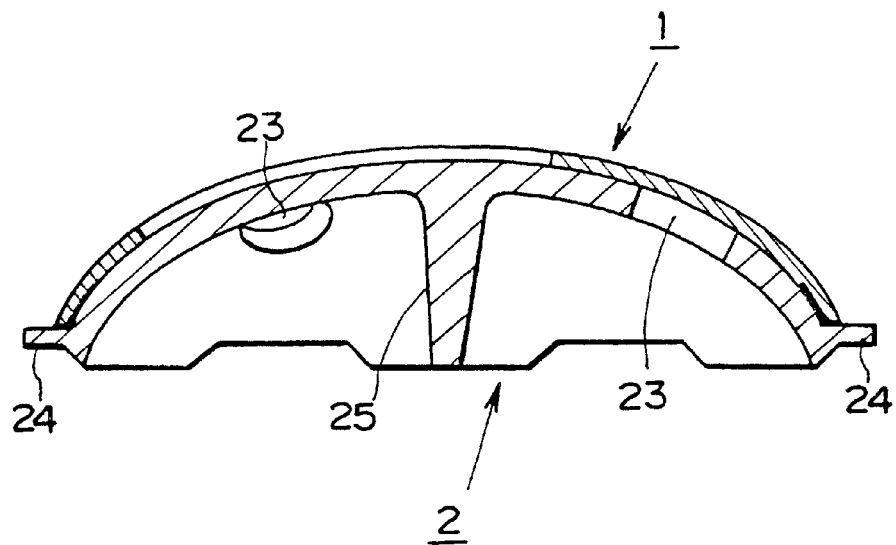
FIG. 10 is a sectional view showing a fifth embodiment of a valve of a physical protector according to this invention.

FIG. 10 shows a fifth embodiment of a valve for use in a physical protector of the invention, in which a support column 25 is provided on a central portion of the inside of the seal member 2 of the aforenoted fourth embodiment.

According to this embodiment, the shape of the overall valve can be maintained by the support column 25, so that the seal member 2 is prevented from being deformed unnecessarily. By depressing the valve, the support column 25 is thrust into the opening in the bag member 11, thereby facilitating the flowing of the air therethrough. Other operations and effects are the same as those of the aforesaid fourth embodiment.

Figure 11:
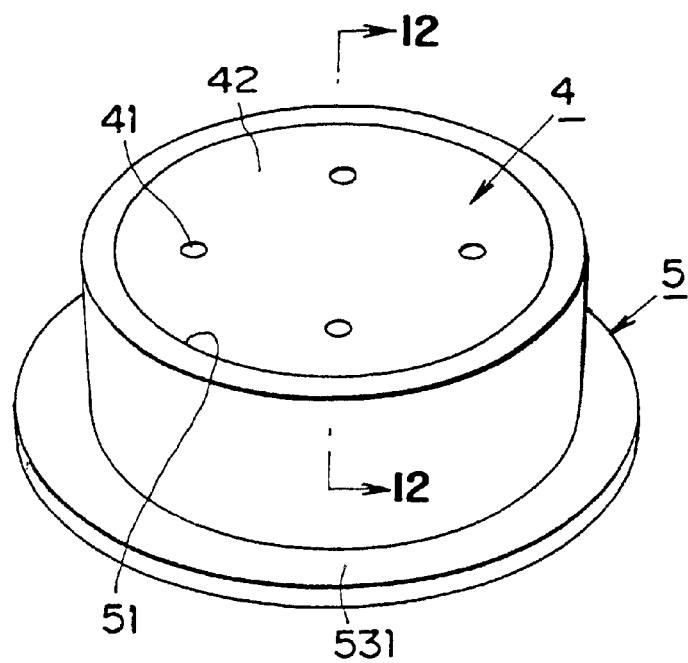
FIG. 11 is a sectional view showing a sixth embodiment of a valve of a physical protector according to this invention.
Figure 12:
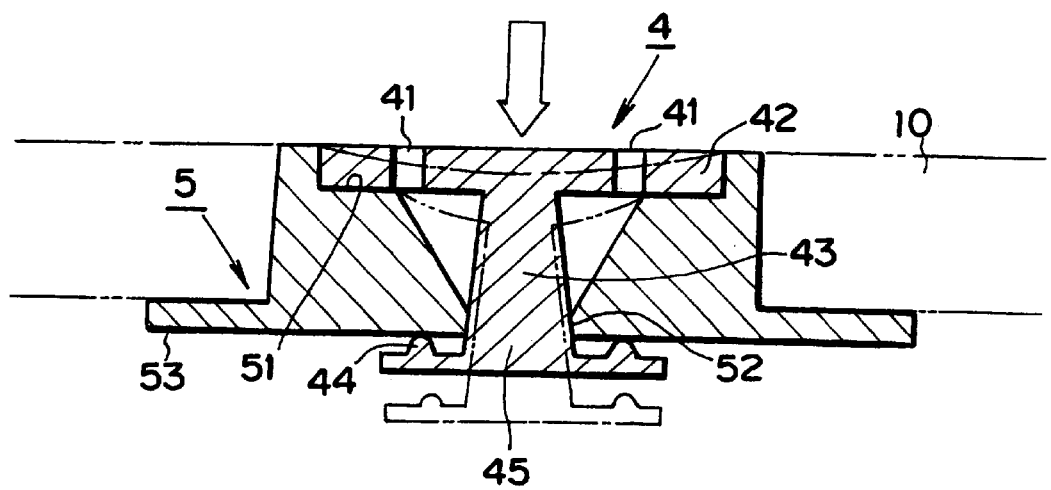
FIG. 12 is a section taken on line 12—12 in FIG. 11.
Figure 13:
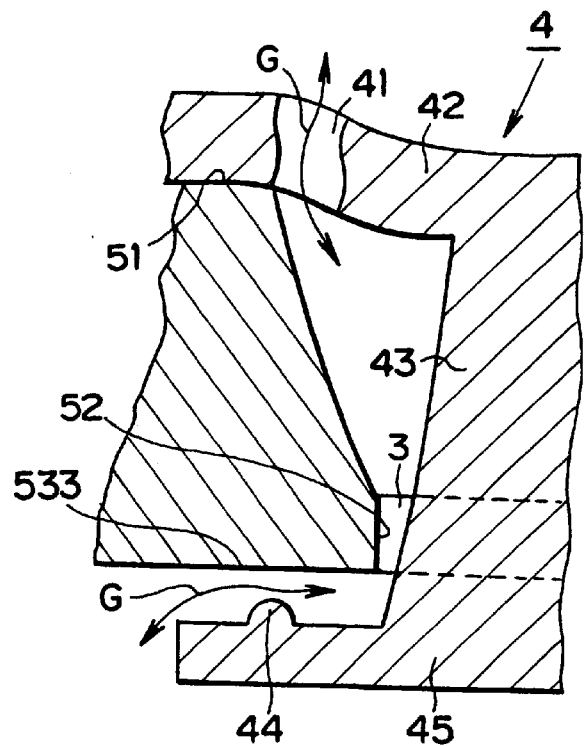
FIG. 13 is an enlarged operational view of a principal portion of FIG. 12.

FIG. 11 through FIG. 13 show a sixth embodiment of a valve for use in the physical protector of the invention, which comprises one seal member 4 formed of relatively soft synthetic resin in the shape of a valve body, and another seal member 5 formed of relatively rigid synthetic resin in the shape of a valve seat.

The seal member 4 comprises a thin depressing plate 42 with vent holes 41, a conical leg portion 43 extending from the depressing plate 42, and a bottom plate 45 with a protrusion 44 confronting the depressing plate 42 astride the leg portion 43. Thus, the seal member 4 has a substantially H-shaped vertical cross section as illustrated. The other seal member 5 is formed in a sleeve for accommodating the seal member 4, and comprises a step portion 51 with which the depressing plate 42 is engaged, a fitting hole 52 serving as an accommodating hole for receiving the largest part 431 of the aforesaid leg portion 43, and a flat flange 53 projecting outward.

According to this embodiment, the overall valve is made thin so that the bag member 11 can be engaged with an outer peripheral portion 532 and the flange 531 of the other seal member 5. In the assembled state of the both seal members 4 and 5, the largest part 431 of the leg portion 43 and the fitting hole 52 are fitted in a tapering state to thereby close the air passage 3. At that time, the protrusion 44 on the bottom plate 45 is in contact with a bottom surface 533 of the other seal member 5 to close the air passage 3. By pushing down the depressing plate 42 of the seal member 4, only the seal member 4 is deformed without deforming the other seal member 5. As a result, the largest part 431 of the leg portion 43 and the fitting hole 52 are disengaged, and simultaneously, the protrusion 44 and the bottom surface 533 are disengaged, consequently opening the air passage 3.

The protrusion 44 of the seal member 4 has a function of preventing the bottom plate 45 from touching the other seal member 5. The other operations and effects are the same as those of the first embodiment.

FIG. 14 through FIG. 17 show a seventh embodiment of a valve for use in a physical protector of the invention, in which the depressing plate 42 in the aforenoted sixth embodiment is provided on its central portion with a projection 421.

Figure 14:
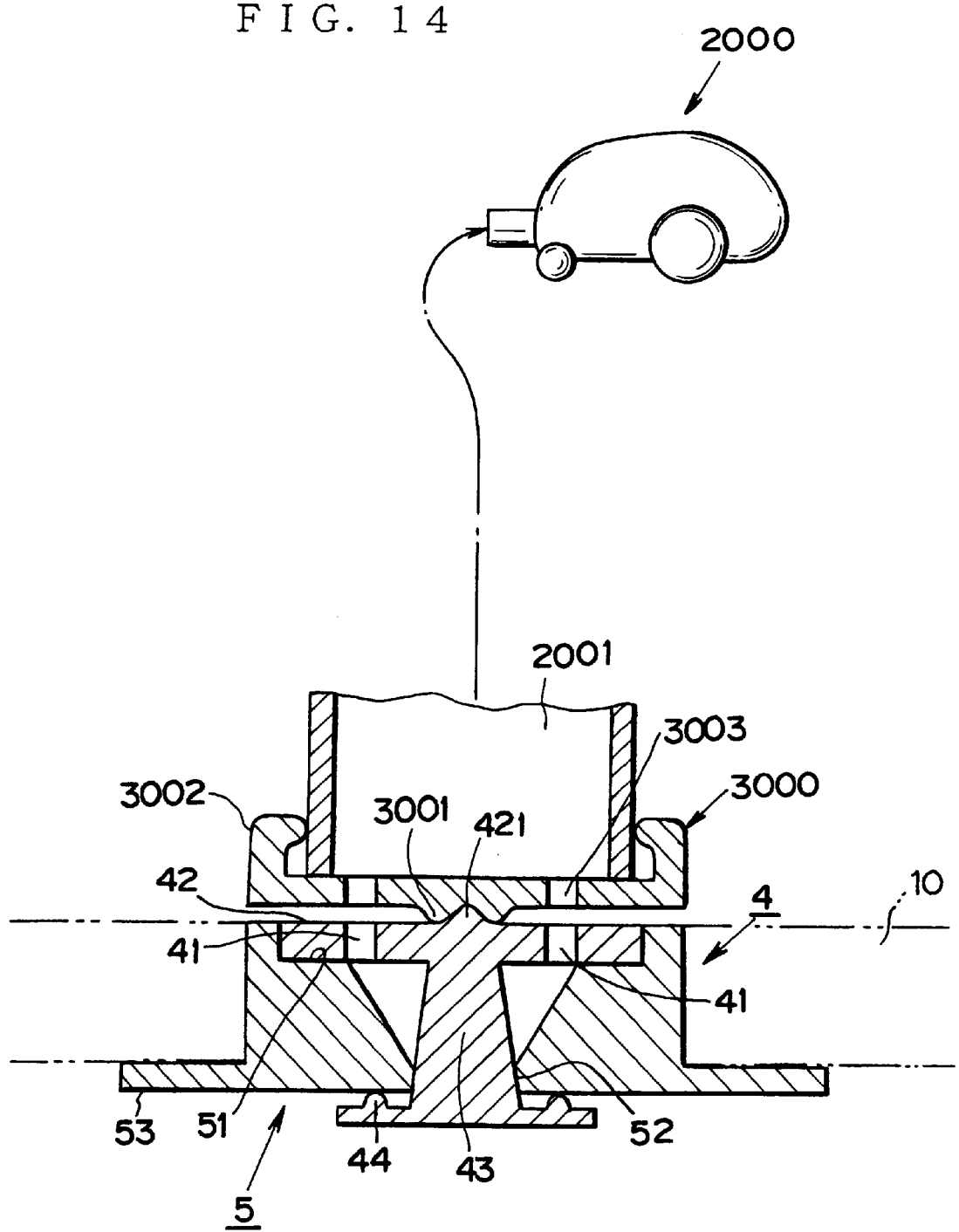
FIG. 14 is a sectional view showing a seventh embodiment of a valve of a physical protector according to this invention.
Figure 15:
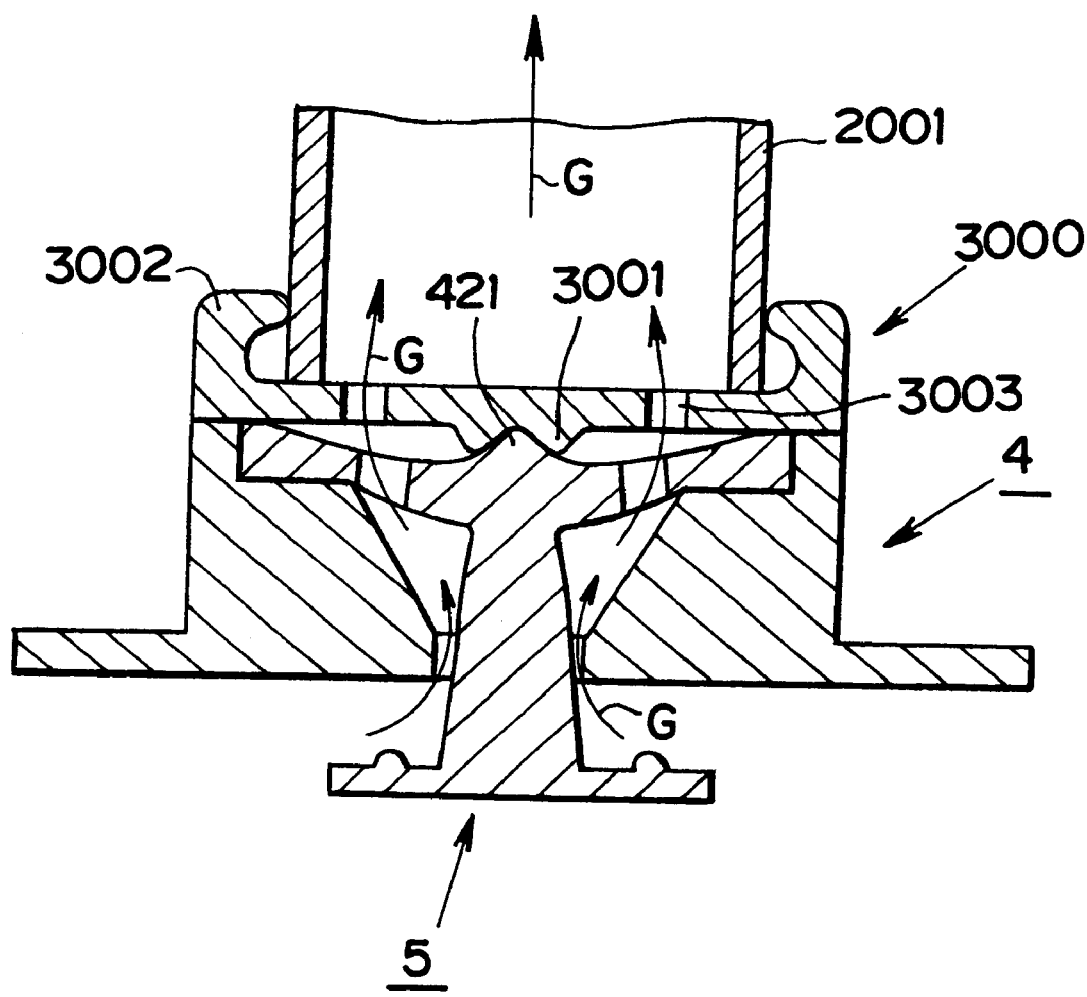
FIG. 15 is a view showing the valve of FIG. 14 in use.

This embodiment makes use of a home vacuum cleaner 2000, so as to attach a suction hose 2001 of the cleaner to an adapter 3000 to forcibly discharge fluid G, as shown in FIG. 14 and FIG. 15. The adapter 3000 has a projection receiver 3001 having a function of depressing the aforesaid projection 421, a retaining portion 3002 for the suction hose 2001, and a vent hole 3003 for connecting the projection receiver 3001 to the retaining portion 3002.

Figure 16:
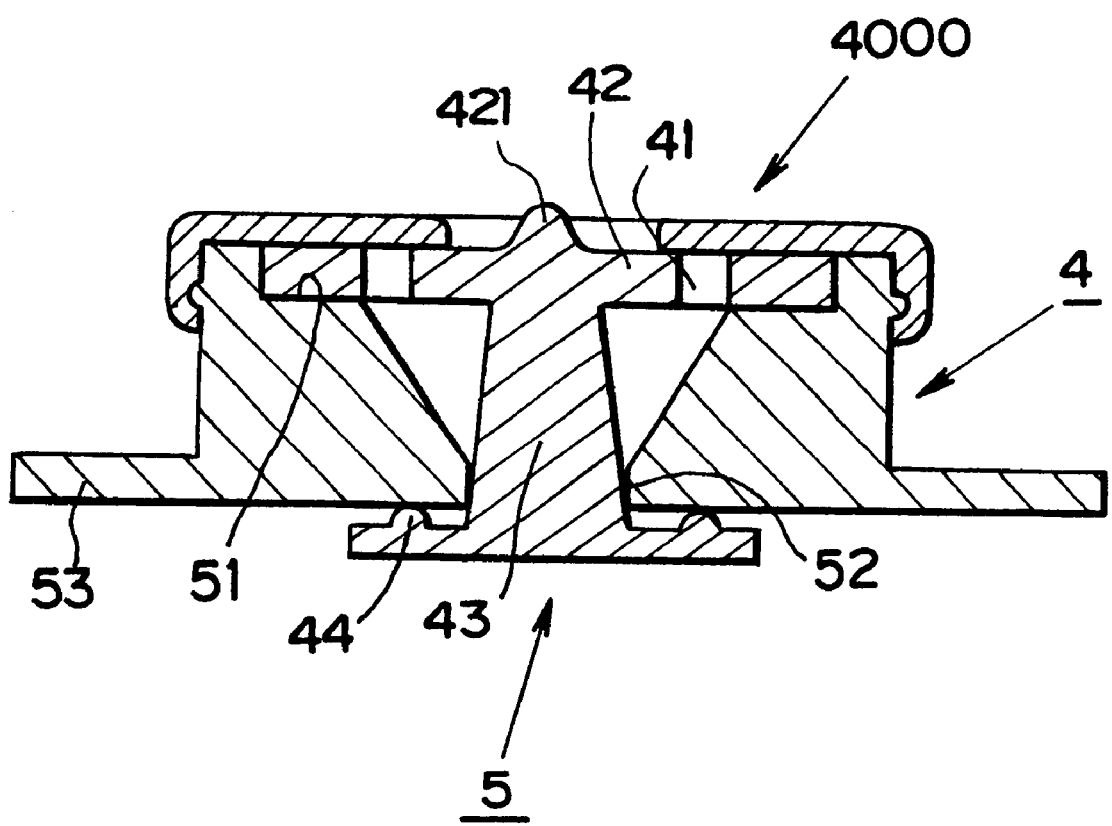
FIG. 16 is a view showing another state in which the valve of FIGS. 14 and 15 is used.
Figure 17:
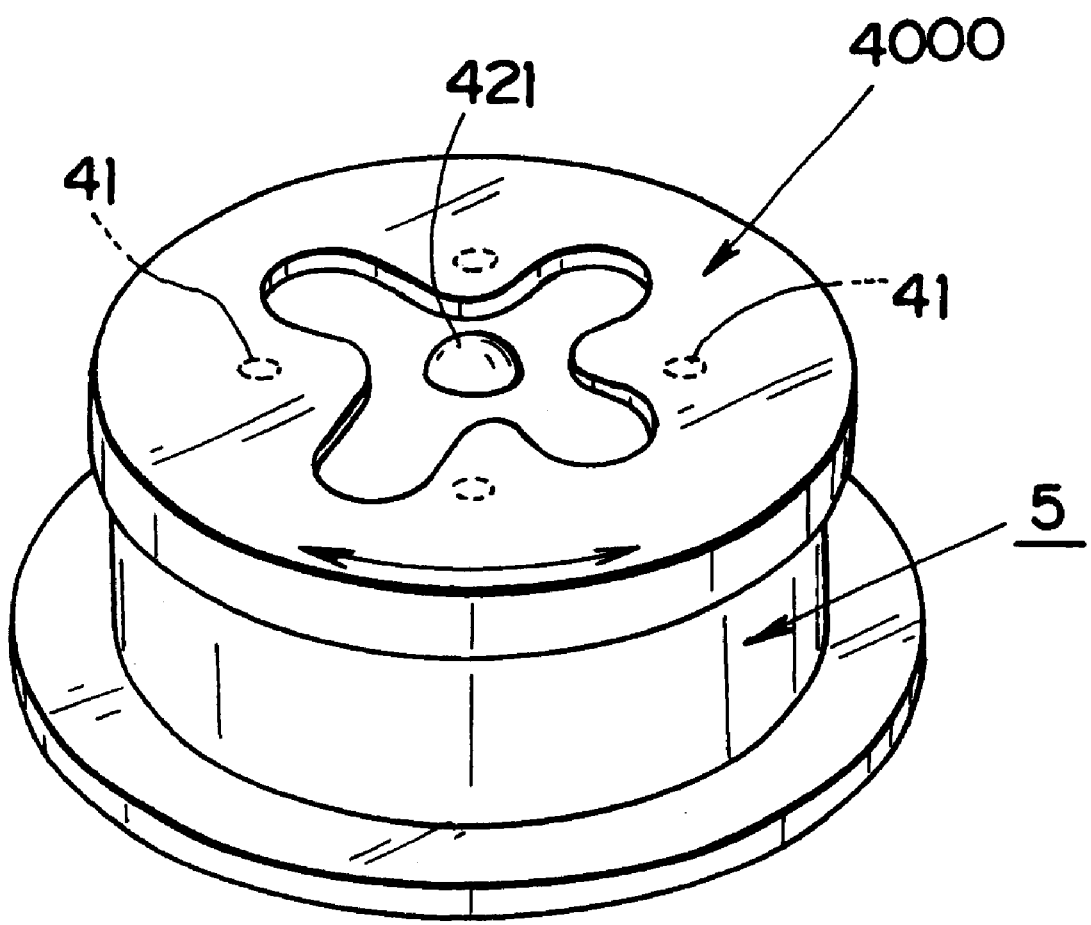
FIG. 17 is a perspective view of FIG. 16.

The vent hole 41 in the seal member 4 is closed with a screw cap 4000 to be attached to the united seal members 4 and 5, as shown in FIG. 16 and FIG. 17, thus improving its sealing property. Furthermore, since the projection 421 rises, handling of the valve is not spoiled even when the screw cap 4000 is attached to the united seal members 4 and 5.

Figure 18:
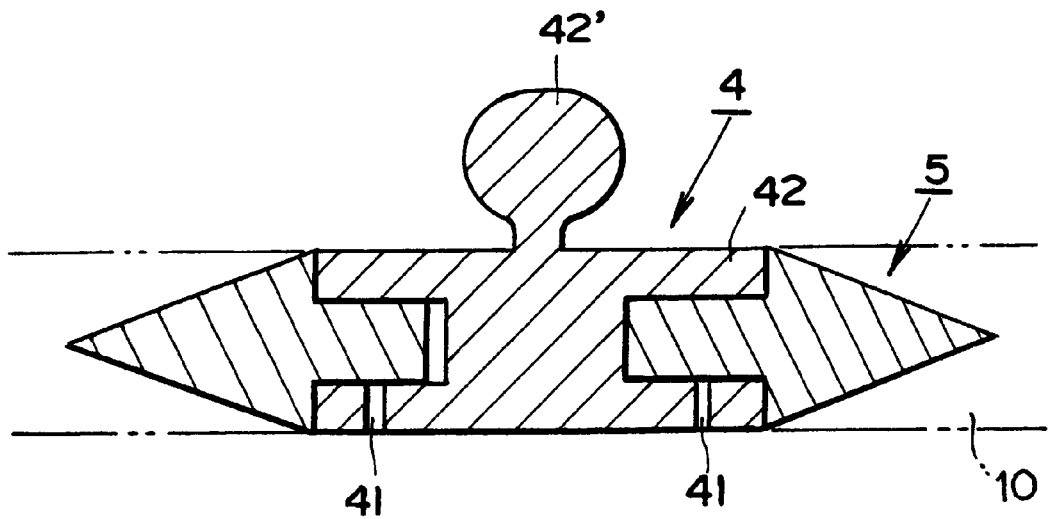
FIG. 18 is a sectional view showing an eighth embodiment of a valve of a physical protector according to this invention.
Figure 19:
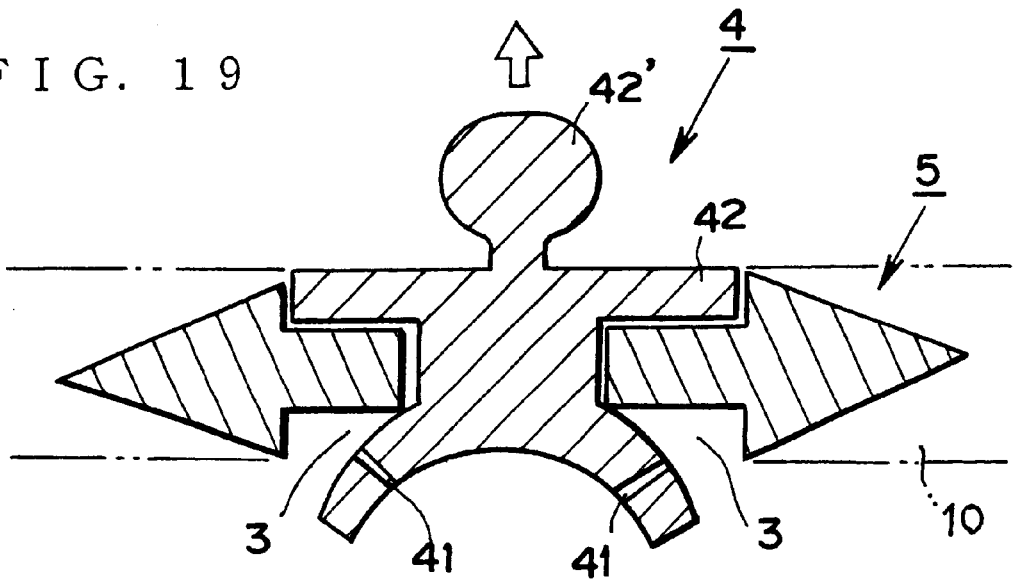
FIG. 19 is an operational view of FIG. 18.

FIG. 18 and FIG. 19 show an eighth embodiment of a valve for use in a physical protector of the invention in which relatively soft synthetic resin seal member 4 having a substantially H-shaped vertical cross section in the aforementioned sixth embodiment is provided on its upper surface with a projection 42'.

According to this embodiment, the depressing plate 42 in the sixth embodiment can be lifted up by using the projection 42', thereby deforming the seal member 4 upward inversely to the sixth embodiment, to open the air passage 3. Thus, the air passage 3 is reliably opened by the operation of the projection 42'. The valve can be steadily fixed onto the bag member 10 by sharpening the outer peripheral edge of the seal member 5 so as to have the seal member ingrown into the bag member.

Figure 20:
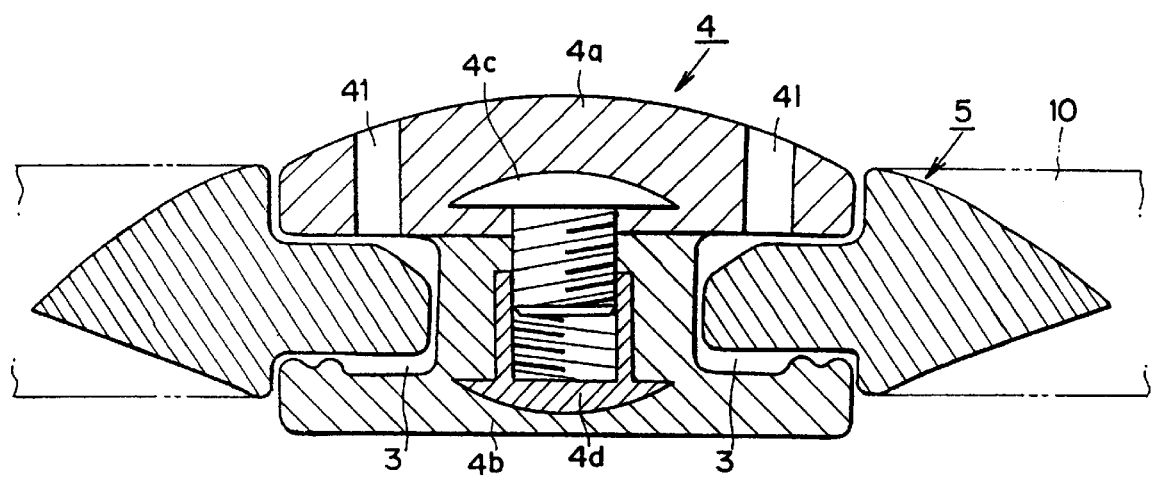
FIG. 20 is a sectional view showing a ninth embodiment of a valve of a physical protector according to this invention.
Figure 21:
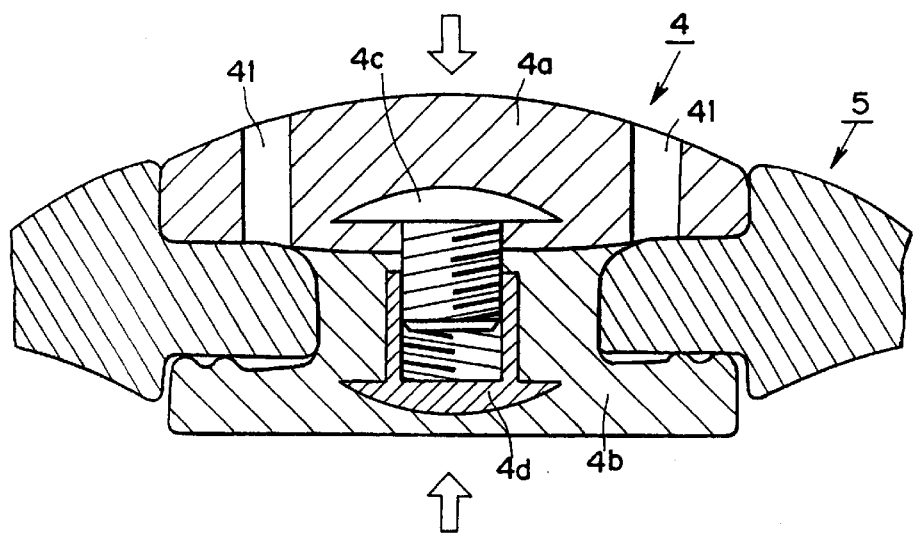
FIG. 21 is an enlarged operational view of a principal portion of FIG. 20.

FIG. 20 and FIG. 21 show a ninth embodiment of a valve for use in a physical protector of the invention, in which the relatively soft seal member 4 is divided into an upper part 4a and a lower part 4b. The upper part 4a incorporates a male screw 4c, and the lower part 4b incorporates a female screw 4d, so that the upper and lower parts rotate relatively to bring the seal members into press contact with each other. The other seal member 5 is made rigid and united with the bag member 10 similarly to the eighth embodiment.

By relatively rotating the upper part 4a and the lower part 4b to be tightened, the seal member 4 comes in press contact with the other seal member 5 while being deformed, thus closing the vent hole 41. By inversely rotating the upper part 4a and the lower part 4b to loosen, the seal member 4, shaped in the form of a valve body, elastically regains its original shape, releasing from the other seal member 5 shaped in the form of a valve seat, and consequently opening the vent hole 41. Thus, since this embodiment utilizes screwing pressure, the vent hole 41 can be securely closed.

Figure 22:
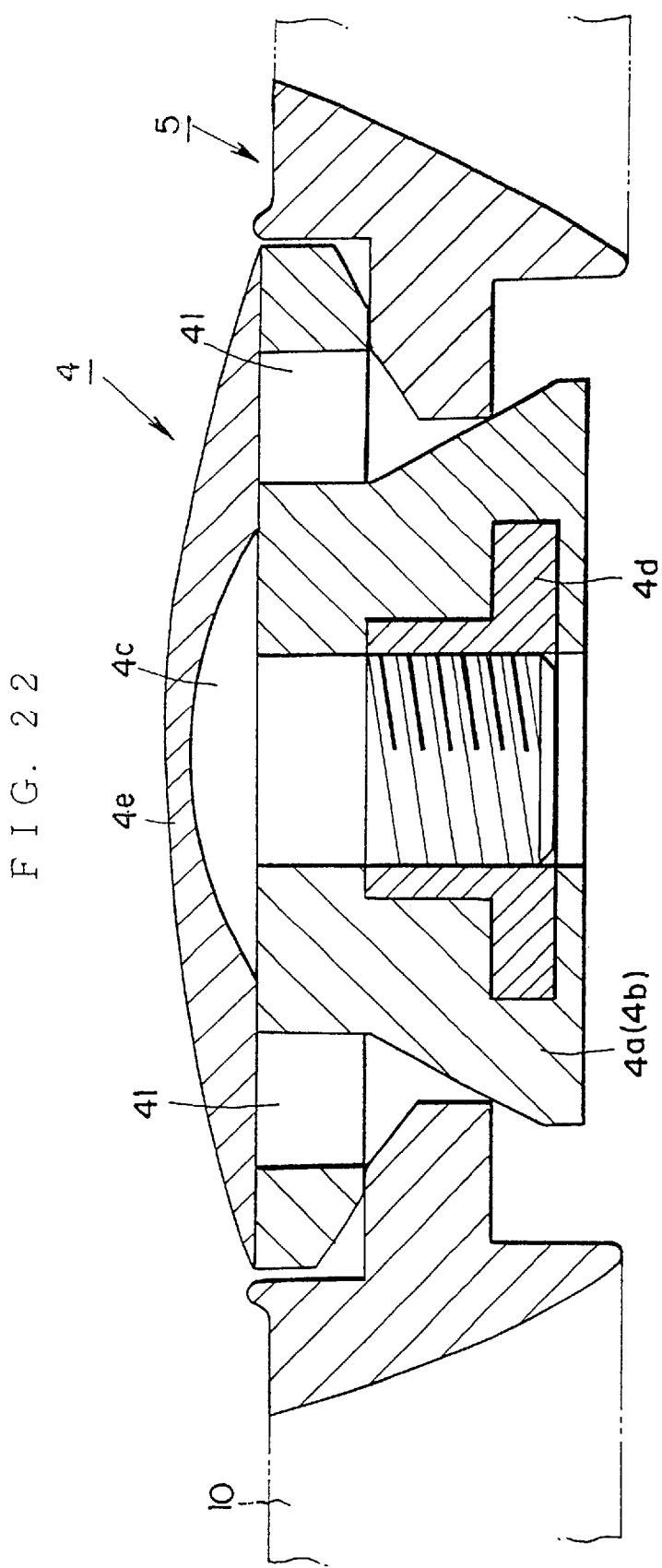
FIG. 22 is a sectional view showing a tenth embodiment of a valve of a physical protector according to this invention.
Figure 23:
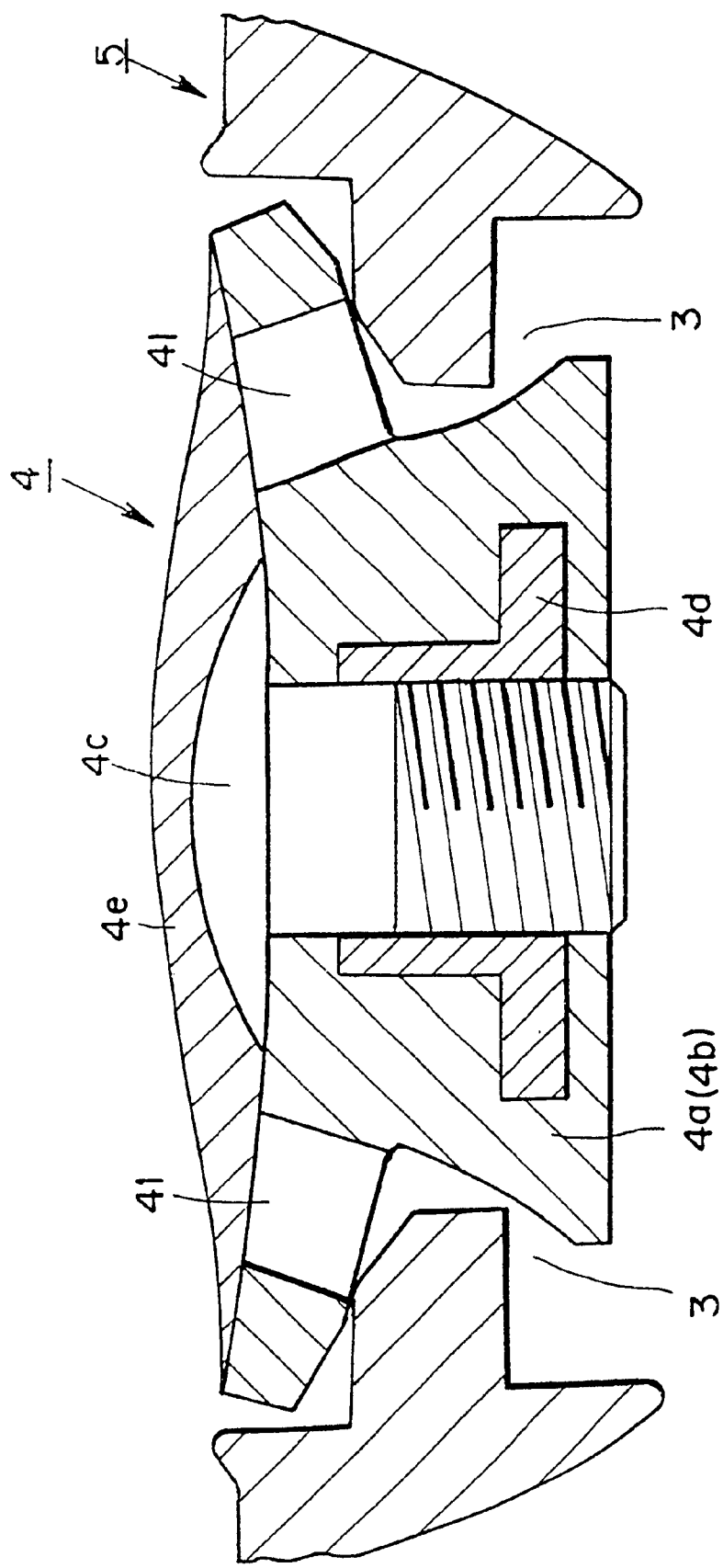
FIG. 23 is an operational view of FIG. 22.

FIG. 22 and FIG. 23 show a tenth embodiment of a valve for use in the physical protector of the invention, in which the upper part 4a and the lower part 4b of the seal member 4, which is made of relatively soft synthetic resin in the aforementioned ninth embodiment, are integrally united, and the male screw 4c is covered with a cover 4e made of thin and soft synthetic resin.

In this embodiment, the male screw 4c can be easily operated through the cover 4e with a fingertip. Therefore, this valve becomes easy to handle. By rotating the male screw 4c, the vent hole 41 and the air passage 3 are closed. Since the cover 4e excels in sealing property, this embodiment enjoys sufficient waterproof even if the male screw 4c and the female screw 4d are made of metal.

Figure 24:
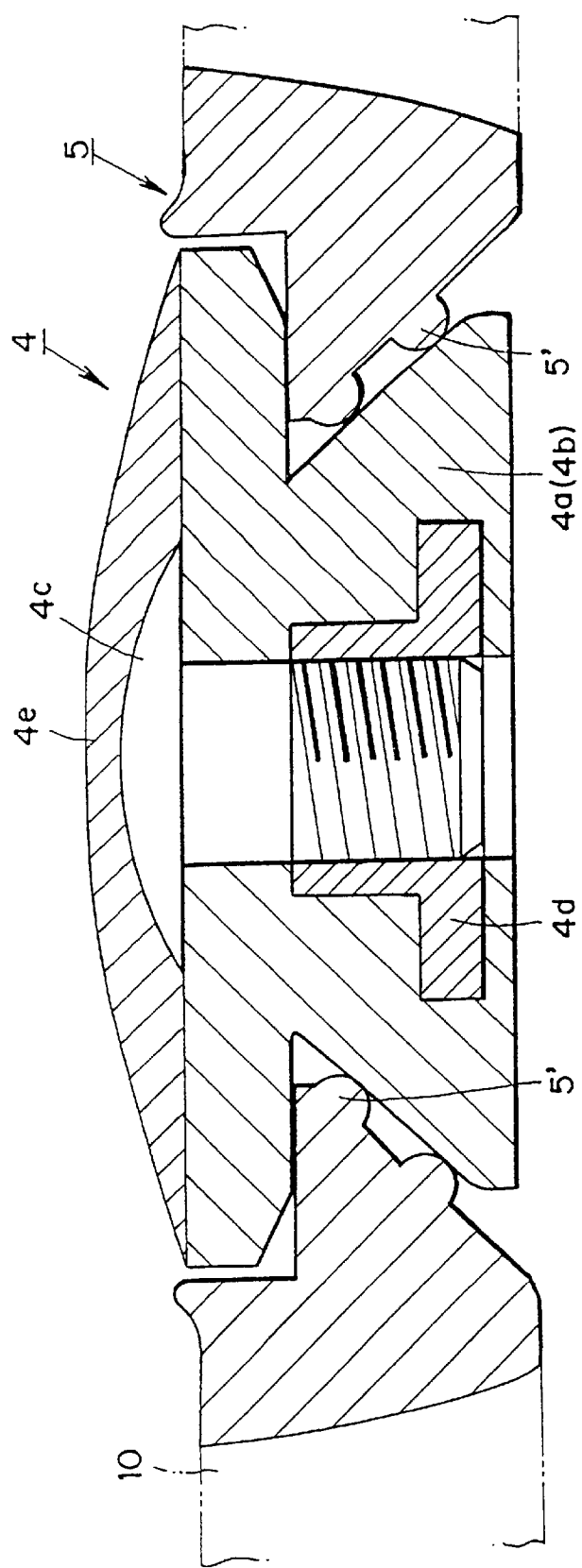
FIG. 24 is a sectional view showing an eleventh embodiment of a valve of a physical protector according to this invention.
Figure 25:
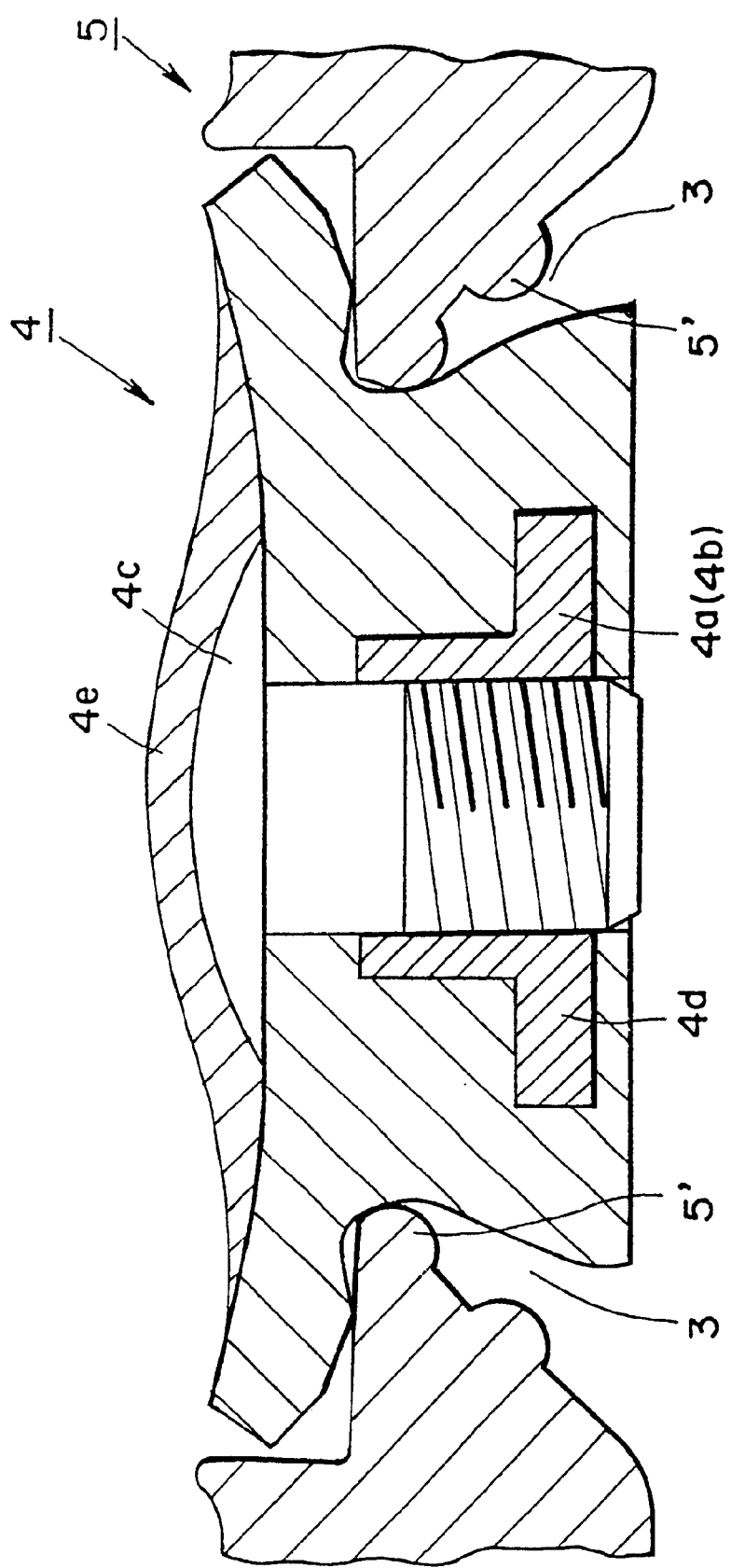
FIG. 25 is an operational view of FIG. 24.

FIG. 24 and FIG. 25 show an eleventh embodiment of a valve for use in a physical protector of the invention, in which the vent hole 41 is omitted from the aforesaid tenth embodiment, and instead the other seal member 5 is provided with rugged portion 5'.

This embodiment enjoys excellent responsiveness in opening and closing the air passage 3 due to engagement and disengagement of the rugged portion 5' with the other seal member 4. It is preferable to form a plurality of rugged portions 5'.

Figure 26:
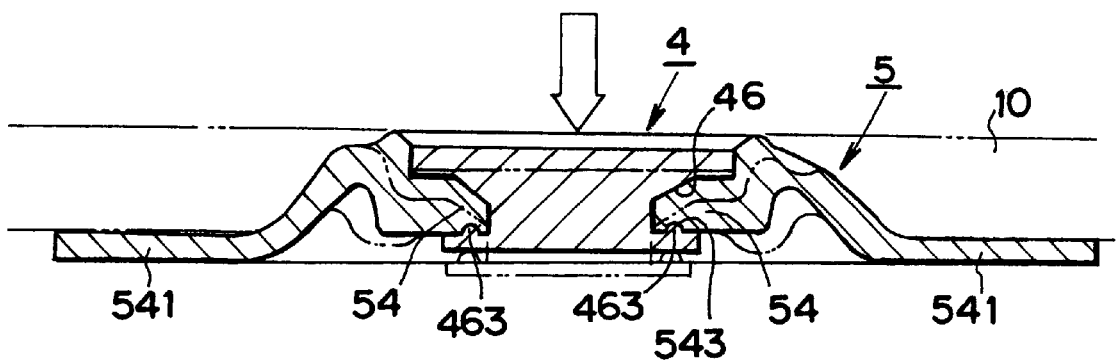
FIG. 26 is a sectional view showing a twelfth embodiment of a valve of a physical protector according to this invention.
Figure 27:
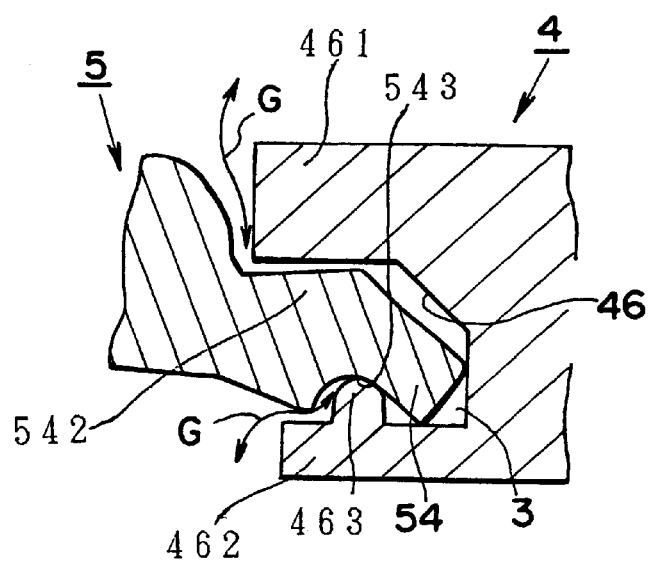
FIG. 27 is an operational view of FIG. 26.

FIG. 26 and FIG. 27 show a twelfth embodiment of a valve for use in a physical protector of the invention, which can be made thinner than those of the aforementioned sixth to eighth embodiments. That is, this embodiment comprises a seal member 4 formed of relatively rigid synthetic resin in the shape of a valve body, and another seal member 5 formed of relatively soft synthetic resin in the shape of a valve seat. The other seal member 5 is provided on its peripheral edge with a flange 541 to be engaged with the bag member 10.

The seal member 4 has a substantially H-shaped vertical cross section, which includes an upper plate 461 engaged with a shoulder 542 of the other seal member 5, and a lower plate 462 engaged with an annular protrusion 54 of the other seal member 5. To be more specific, a protrusion 463 of the seal member 4 is fitted into a groove 543 in the other seal member 5.

In this embodiment, an air passage is closed by engagement of the upper plate 461 and the shoulder 542 and engagement of the protrusion 463 and the groove 543. Subsequently, by depressing the seal member 4, the other seal member is elastically deformed to disengage the annular groove 46 and the annular protrusion 54, thus opening the air passage 3. The other operations and effects are fulfilled similarly to the aforesaid sixth embodiment. In this embodiment, the protrusion 463 may be formed on the other seal member 2, and the groove 543 may be formed in the seal member 1.

Figure 28:
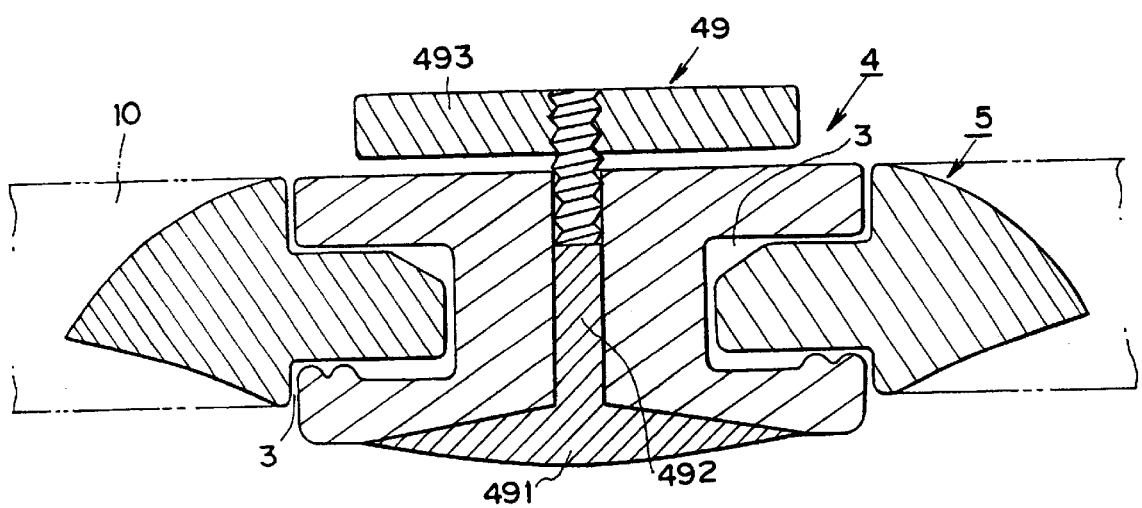
FIG. 28 is a sectional view showing a thirteenth embodiment of a valve of a physical protector according to this invention.
Figure 29:
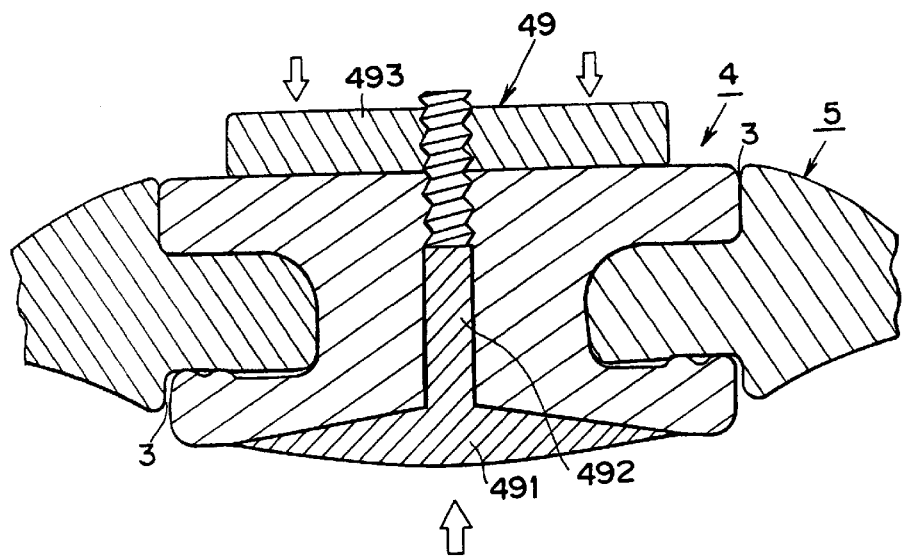
FIG. 29 is an operational view of FIG. 28.

FIG. 28 and FIG. 29 show a thirteenth embodiment of a valve for use in a physical protector of the invention, in which the seal member 4 having a shape such as a valve body is made soft, and the seal member 5 having a shape such as a valve seat is made rigid, similarly to the eighth embodiment described above.

The seal member 4 shaped like a valve body is provided with a rotary pressuring member 49 comprising a base plate 491 being in contact with the inner part of the seal member, a screwed shaft 492 piercing the center of the seal member 4, and a rotary plate 493 in which the screwed shaft is screwed.

In this embodiment, by rotating the rotary plate 493 of the rotary pressuring member 49 to tighten the screwed shaft, the seal member 4 is squeezed between the rotary plate and the base plate 491. As a result, the seal member 4 is compressed vertically and elastically deformed to close the vent hole 3 (FIG. 29).

By rotating the rotary plate 493 in the reverse direction, the seal member 4 is loosened between the rotary plate and the base plate 491, so that it elastically reassumes it own shape, to open the vent hole 3. Thus, opening and closing of the vent hole 3 can be reliably accomplished (FIG. 28).

Figure 30:
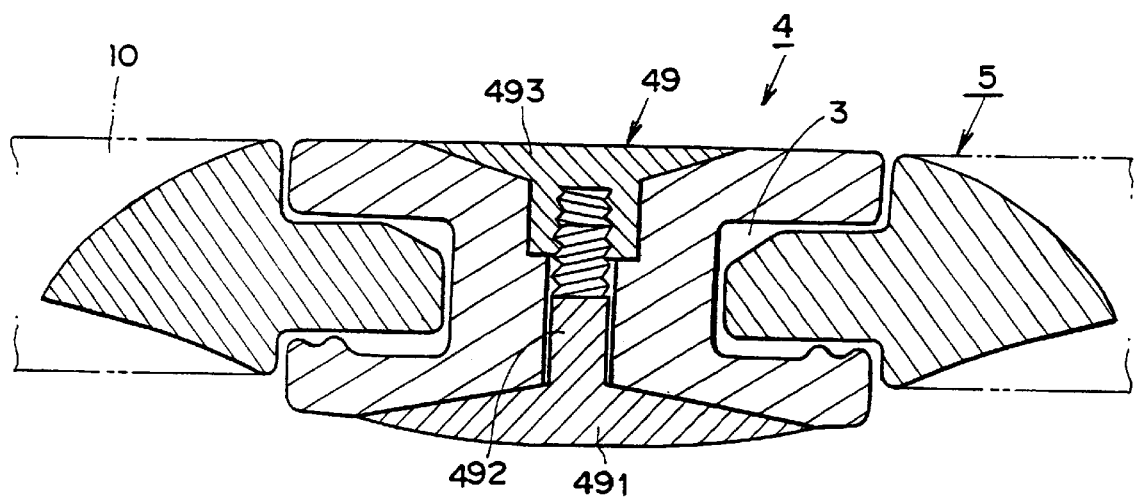
FIG. 30 is a sectional view showing a fourteenth embodiment of a valve of a physical protector according to this invention.
Figure 31:
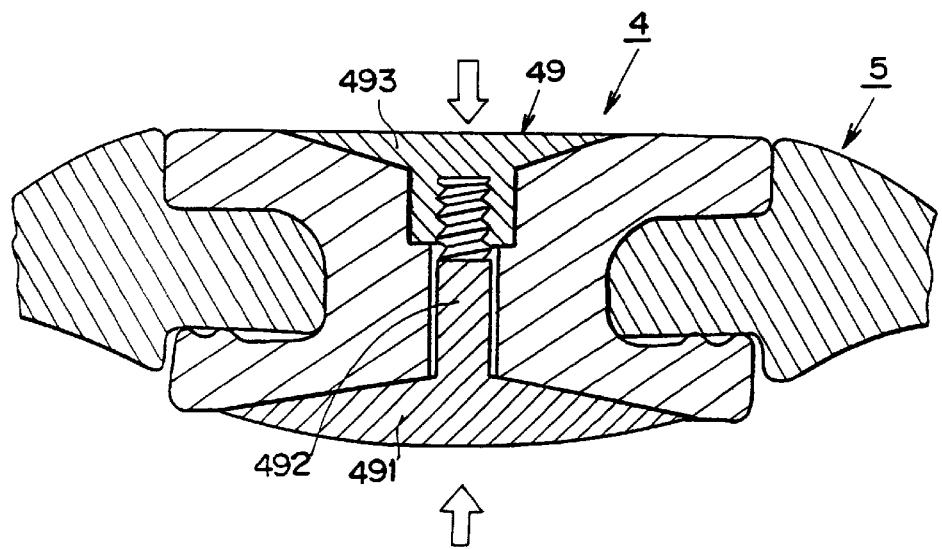
FIG. 31 is an operational view of FIG. 32.

FIGS. 30 and 31 show a fourteenth embodiment in which the rotary plate 493 of the rotary pressuring member 49 in the aforenoted tenth embodiment is embedded in the seal member 4.

According to this embodiment, the projection over the seal member due to the rotary plate can be omitted, so that the valve can be made simple in appearance. Besides, since the contact area of the rotary plate 493 of the rotary pressuring member 49 and the seal member 4 is increased, accidental slackening of the rotary plate 493 can be prevented.

Figure 32:
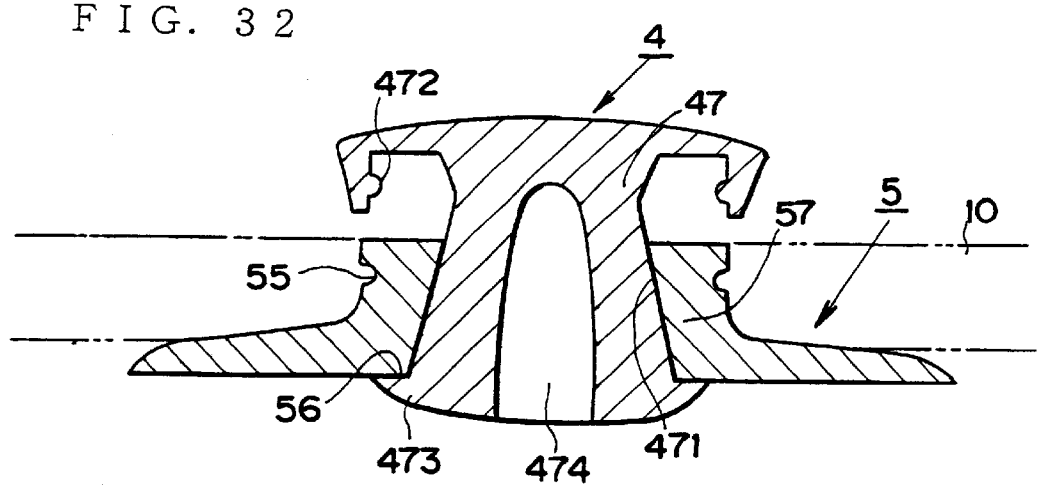
FIG. 32 is a sectional view showing a fifteenth embodiment of a valve of a physical protector according to this invention.
Figure 33:
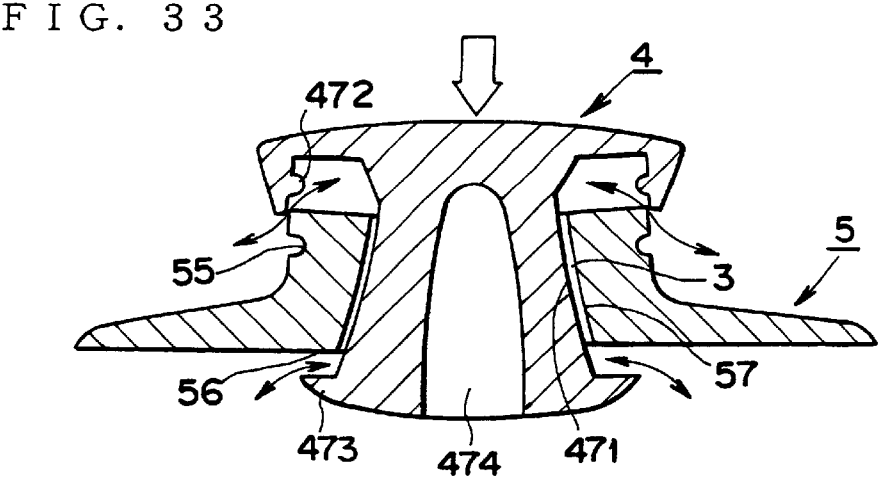
FIG. 33 is an operational view of FIG. 34.
Figure 34:
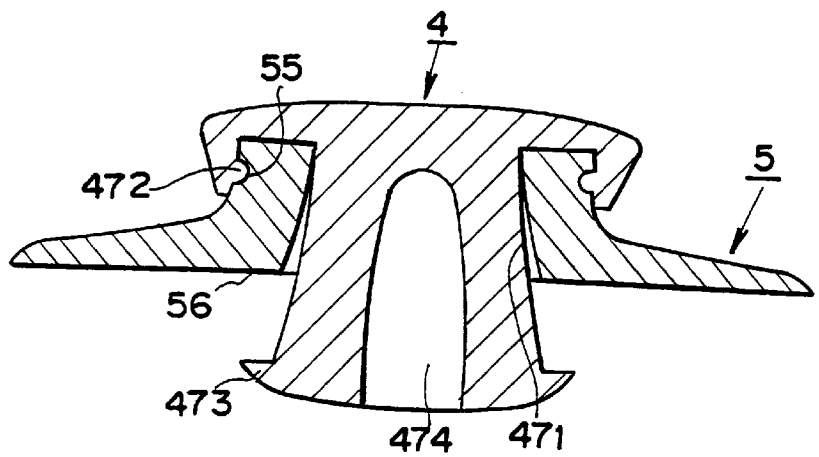
FIG. 34 is another operational view of FIG. 34.

FIG. 32 through FIG. 34 show a fifteenth embodiment of a valve for use in a physical protector of the present invention, which comprises a seal member 4 formed of relatively soft synthetic resin in the shape of a valve body, and another seal member 5 formed of relatively rigid synthetic resin in the shape of a valve seat. The seal member 4 has a conical leg portion 471 on the central portion thereof, which is provided at both its ends with engaging portions 472 and 473. One of the engaging portions, 473, has a pressure receiving hole 474. The other seal member 5 is provided with catch portions 55 and 56 for the engaging portions, which correspond to the engaging portions 472 and 473 of the seal member 4, and a sleeve-like vent hole 57 at its central portion.

In this embodiment, the seal member 4 is thrust in while being deformed by being depressed. As shown in FIG. 32 and FIG. 34, at the time that the engaging portions 472 and 473 are engaged with the catch portions 55 and 56, the air passage 3 is closed by the leg portion 471 fitted in the vent hole 57. As shown in FIG. 33, when the engaging portions 472 and 473 are disconnected from the catch portions 55 and 56, the leg portion 471 is separated from the vent hole 57 to thereby open the air passage 3. The pressure receiving hole 474 of the seal member 4 plays an auxiliary role in controlling internal pressure in a device to which the valve is attached, so that the seal member 4 assumes the position to close the vent hole. The other operations and effects are fulfilled similarly to the aforesaid ninth embodiment.

Figure 35:
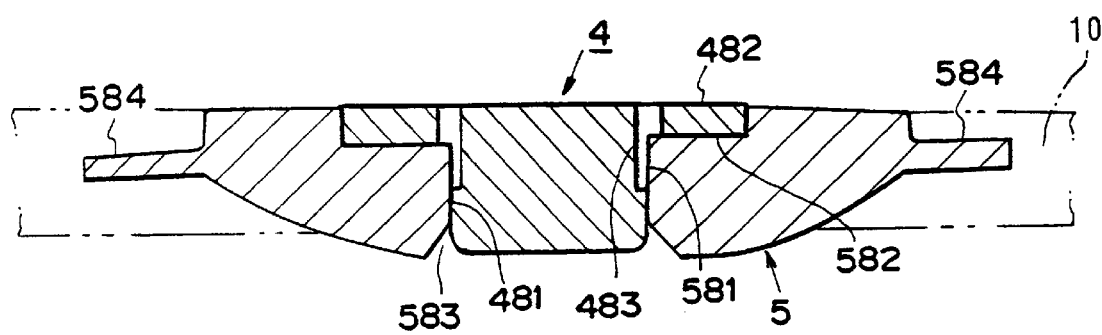
FIG. 35 is a sectional view showing a sixteenth embodiment of a valve of a physical protector according to this invention.
Figure 36:
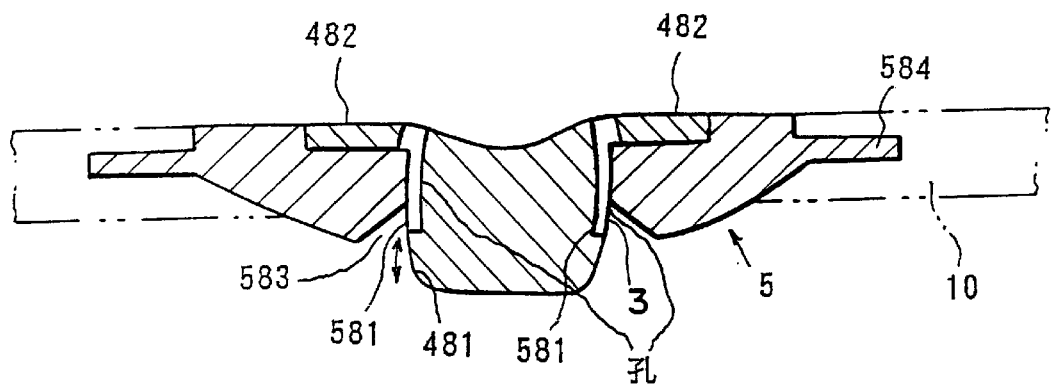
FIG. 36 is an operational section of FIG. 35.
Figure 37:
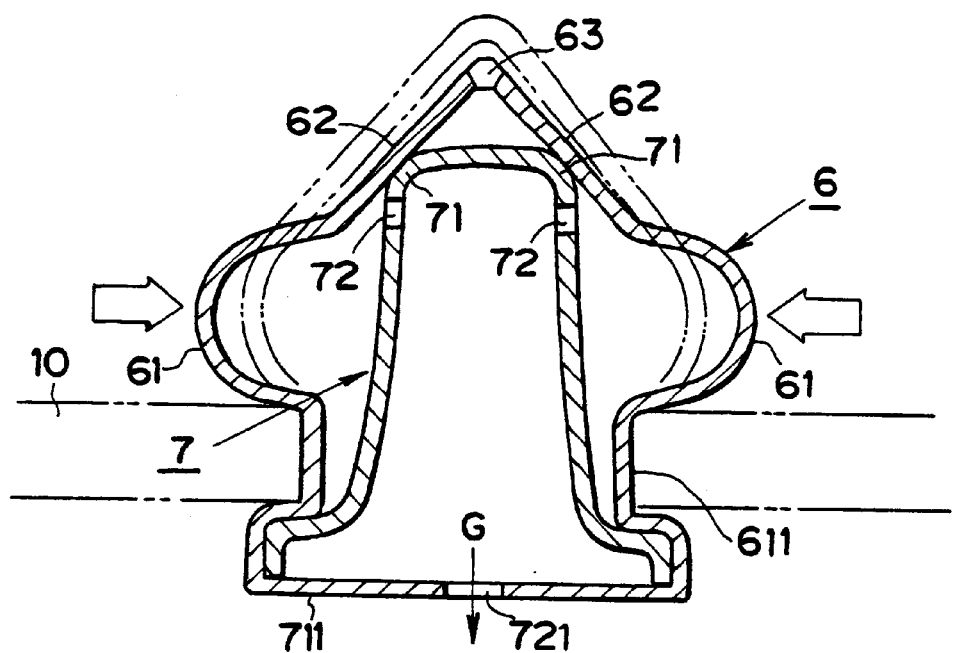
FIG. 37 is a sectional view showing a seventeenth embodiment of a valve of a physical protector according to this invention.

FIG. 35 and FIG. 36 show a sixteenth embodiment of a valve for use in a physical protector of the present invention, which comprises a seal member 4 formed of relatively soft synthetic resin in the shape of a valve body, and another seal member 5 formed of relatively rigid synthetic resin in the shape of a valve seat.

The seal member 4 has a substantially column-shaped leg portion 481 on a central portion thereof, which is provided on its upper portion with a flange 482 spreading outward. The aforementioned leg portion 481 is provided in its peripheral surface with a plurality of groove holes 483 each extending to the middle of the leg portion in the axial direction through the flange. The other seal member 5 has a substantially columnar vent hole 581 into which the leg portion 481 is fitted, and is provided in its upper portion with a step portion 582 for receiving the flange 482 so as to close the vent hole. The other seal member 5 is provided in its lower portion with a cut 583 to shorten the vertical length of the vent hole 581 and on its outer periphery with a fitting portion 584 to be connected to the bag member 10.

In this embodiment, the flange 482 of the leg portion 481 is fitted in the step portion 582, thus closing the groove holes 483. As illustrated in FIG. 36, by pushing down the seal member 4, the leg portion 481 moves downward, so that the groove holes 483 partially deviate downward from the vent hole 581 and confront the cut 583, thus opening the air passage 3. The other operations and effects are the same as those of the fifteenth embodiment as mentioned above.

FIG. 37 through FIG. 40 show a seventeenth embodiment of a valve for use in a physical protector of the invention, which comprises a hollow seal member 6 with a bulge, made of relatively soft synthetic resin, and another hollow seal member 7 made of relatively rigid synthetic resin. The seal member 6 has a pump portion 61 largely expanding outward, a taper portion 62 tapered off upward from the pump portion 61, and a vent hole 63 formed in the upper central portion of the seal member. Under the pump portion 61, a contracted portion 611 is formed for retaining the bag member 10.

The other seal member 7, which is accommodated in the seal member 6, has a head portion 71 to be placed inside the taper portion 62, vent holes 72 bored near the head portion 71, and a bottom portion 711 with a vent hole 721. In an ordinary state, the taper portion 62 and the head portion 71 are in contact with each other, thus closing the air passage.

Figure 38:
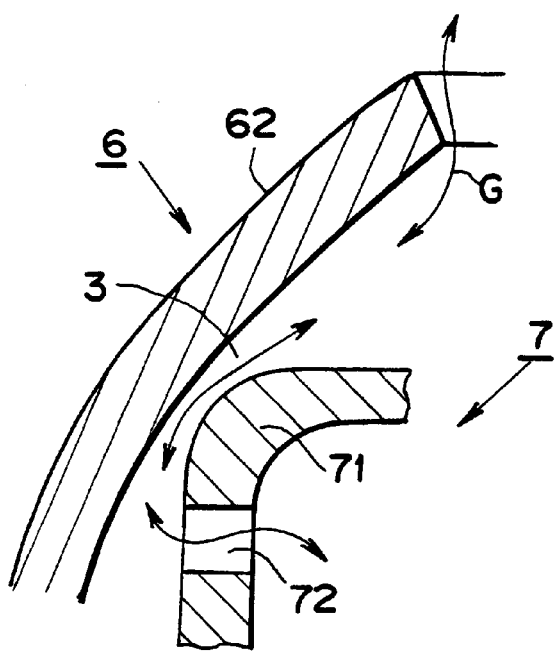
FIG. 38 is an operational view of the principal portion of FIG. 37.

In this embodiment, as shown in FIG. 38, by pressing the pump portion 61 of the seal member 6, fluid G inside the pump portion 61 is forced out from the inside of the seal member 7 through the vent hole 721. At the same time, the seal member 6 is deformed so that the taper portion 62 is separated from the head portion 71 to open the air passage 3, thus allowing fluid G to flow in.

Figure 39:
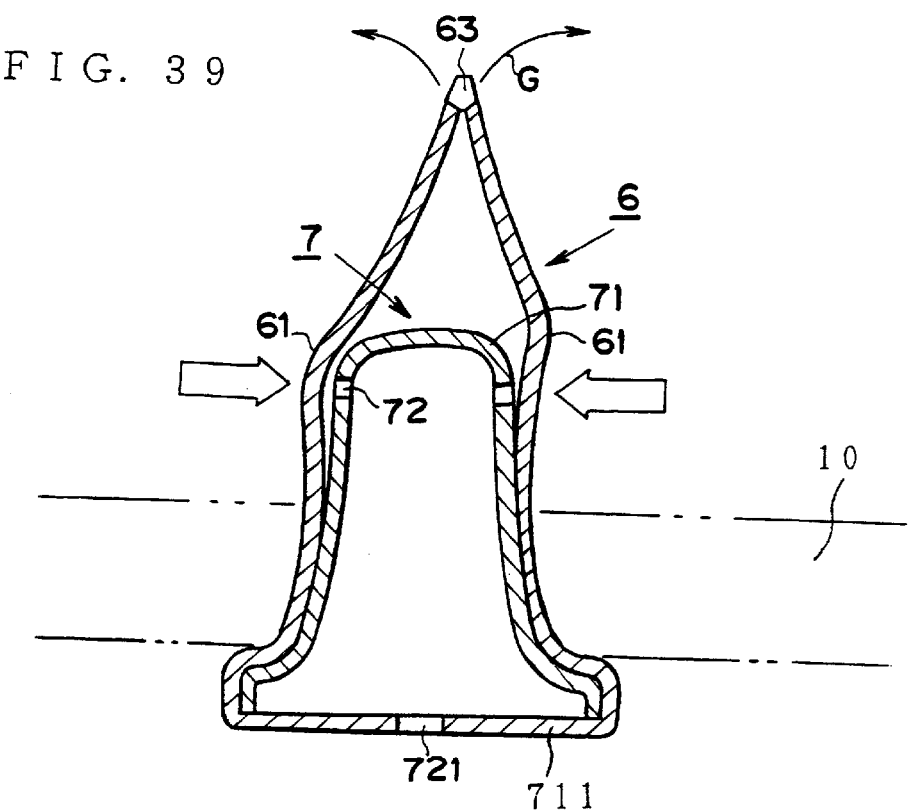
FIG. 39 is another operational view of FIG. 37.
Figure 40:
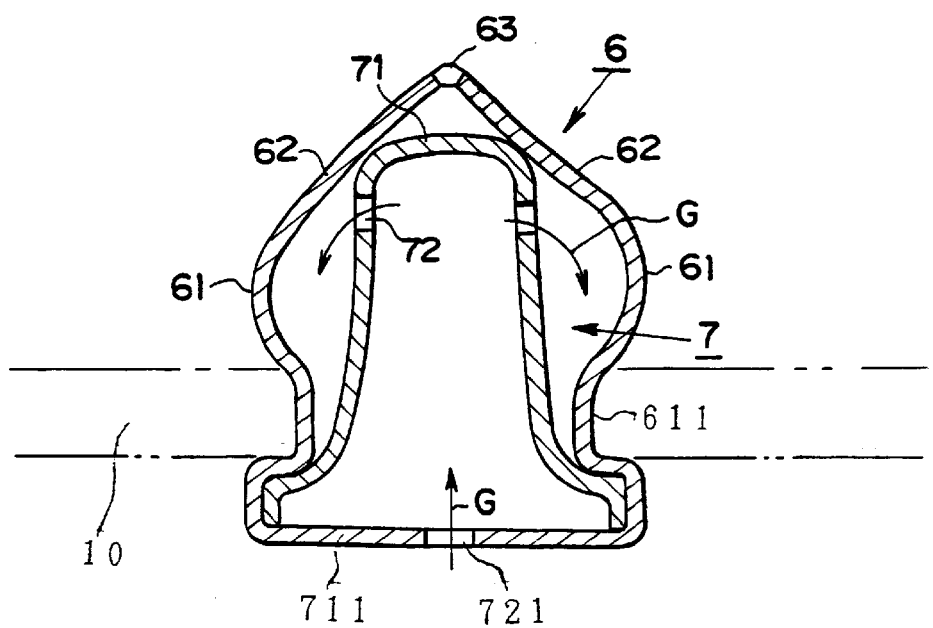
FIG. 40 is still another operational view of FIG. 37.

By forcibly pressing the pump portion of the seal member 6 as shown in FIG. 39, the fluid G can be discharged outward. Thereafter, by releasing the pressing force exerted on the pump portion, the pump portion 61 expands while bringing the taper portion 62 into contact with the head portion 71 as shown in FIG. 40, as a result of which the fluid G inside the other seal member 7 is drawn out. The other operations and effects are the same as those of the first embodiment as mentioned above.

Figure 41:
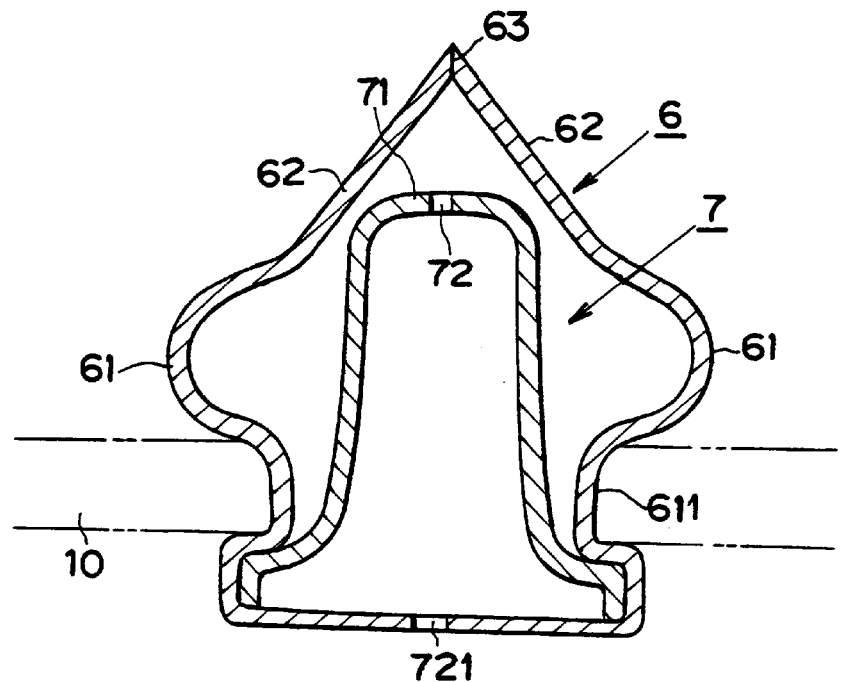
FIG. 41 is a sectional view showing an eighteenth embodiment of a valve of a physical protector according to this invention.
Figure 42:
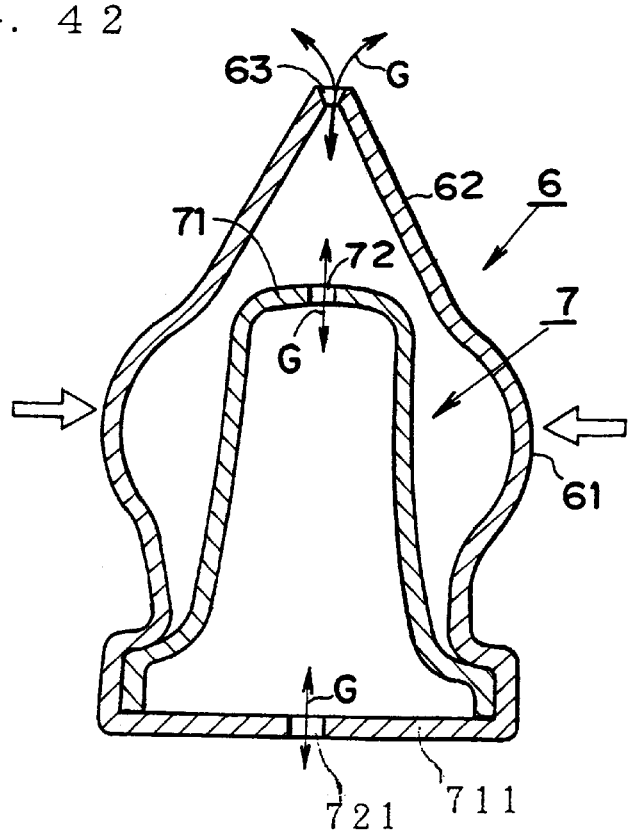
FIG. 42 is an operational view of FIG. 41.

FIG. 41 and FIG. 42 show an eighteenth embodiment of a valve for use in a physical protector of the invention, wherein the vent hole 63 of the seal member 6 in the aforementioned sixteenth embodiment is formed in a slit so as to be closed in an ordinary state. The taper portion 62 of the seal member 6 in this embodiment is kept apart from the head portion 71 of the seal member 7. Thus, the vent hole 63 is ordinarily closed.

In this embodiment, by pressing the pump portion 61 of the seal member 6, the vent hole 63 is forcibly opened to open the air passage 3. The other operations and effects are the same as those of the seventeenth embodiment as mentioned above.

Figure 43:
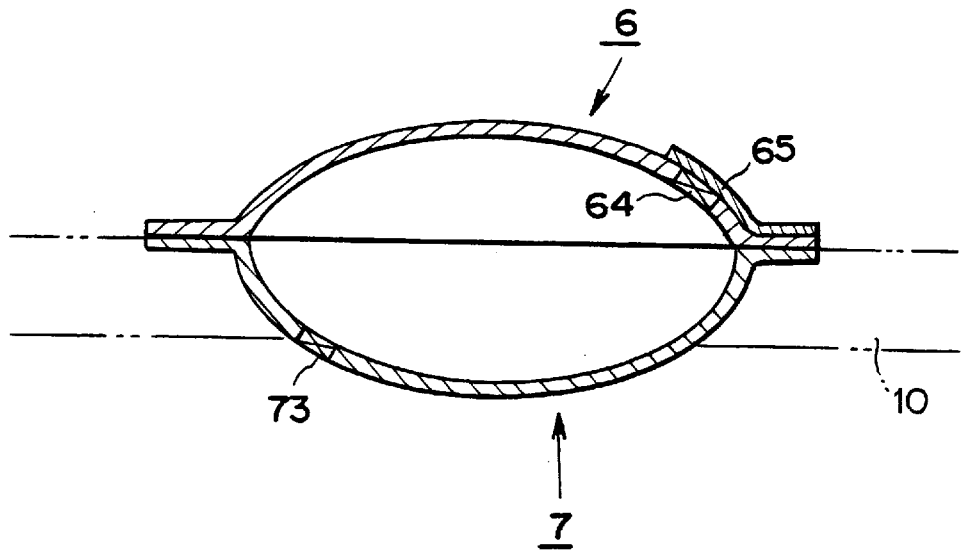
FIG. 43 is a sectional view showing a nineteenth embodiment of a valve of a physical protector according to this invention.
Figure 44:
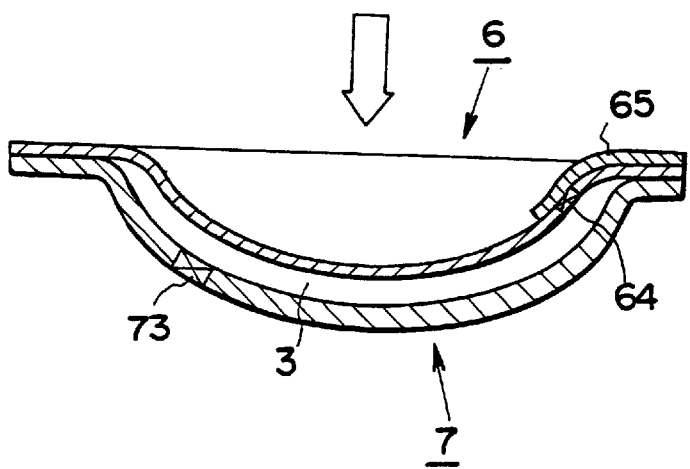
FIG. 44 is an operational view of FIG. 43.

FIG. 43 and FIG. 44 show a nineteenth embodiment of a valve for use in a physical protector of the invention, which is formed by joining a spherical seal member 6 of soft synthetic resin to another spherical seal member 7 of rigid synthetic resin. The seal members have one-way valves 64 and 73, respectively. The one-way valve 64 of the seal member 6 is provided with a stopper 65.

In this embodiment, by deforming the seal member 6 with a pressing force, inner pressure between the seal members 6 and 7 is increased to forcibly open the one-way valves 64 and 73, thus opening the air passage 3. The other operations and effects are the same as those of the first embodiment as mentioned above.

Figure 45:
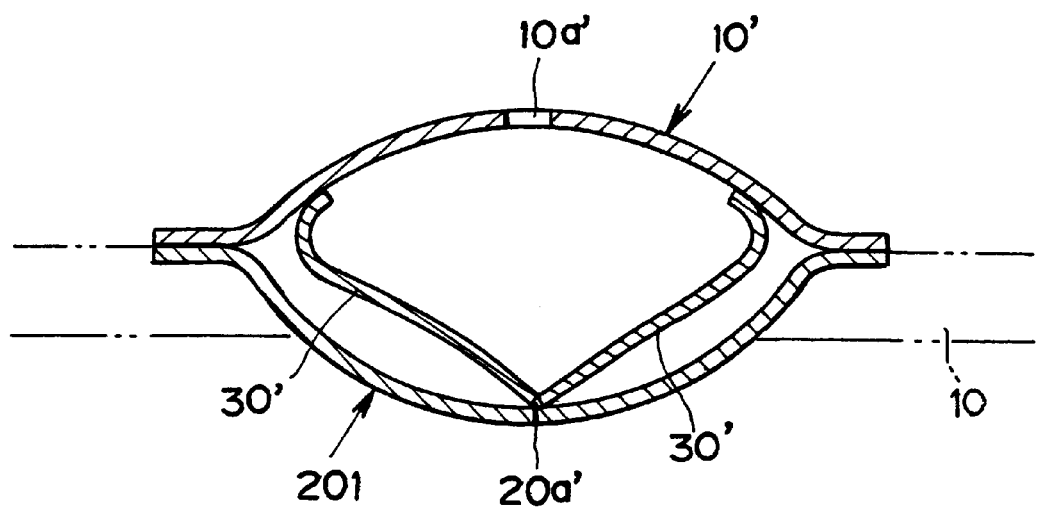
FIG. 45 is a sectional view showing a twentieth embodiment of a valve of a physical protector according to this invention.
Figure 46:
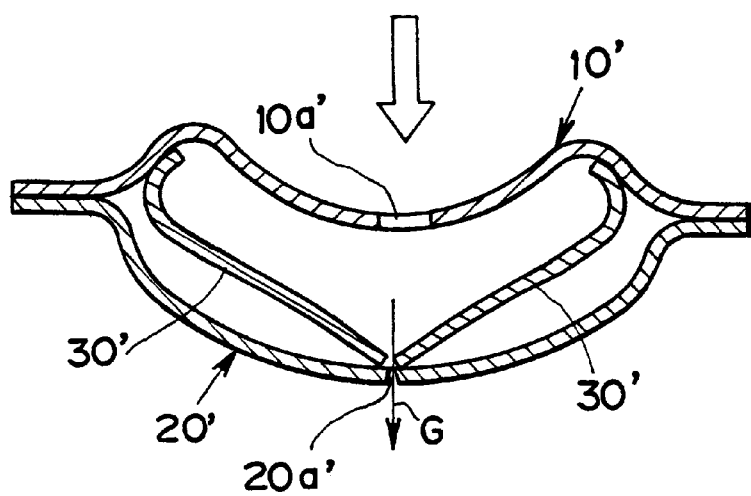
FIG. 46 is an operational view of FIG. 45.
Figure 47:
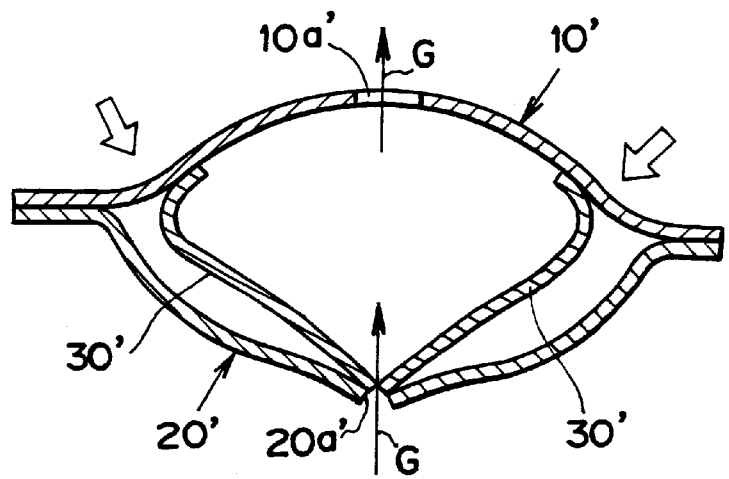
FIG. 47 is still another operational view of FIG. 45.

FIG. 45 through FIG. 47 show a twentieth embodiment of a valve for use in a physical protector of the invention, which is formed by joining relatively soft dome-shaped seal members 10' and 20' and contains a relatively rigid support member 30' extending from the inner side periphery of the seal member 10' to the central portion of the other seal member. The seal member 10' is provided at its central portion with a vent hole 10a' of a normally-open type. The other seal member 20' is provided at its central portion with a vent slit 20a' of a normally-closed type.

In this embodiment, by pressing seal member 10' while closing the vent hole 10a' as shown in FIG. 46, the inner pressure in the space between the seal members 10' and 20' is increased to force the vent slit 20a' to open, thus allowing the fluid G to pass therethrough. By pressing laterally the seal member 10' to depress the support member 30' as shown in FIG. 47, the vent slit 20a' formed in the other seal member 20' is opened by the peak of the support member 30', thus allowing the fluid G to be discharged.

Figure 48:
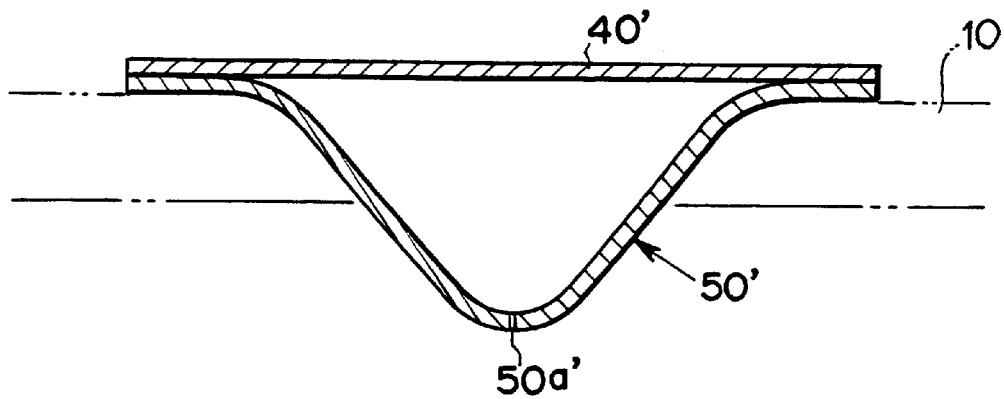
FIG. 48 is a sectional view showing a twenty-first embodiment of a valve of a physical protector according to this invention.
Figure 49:
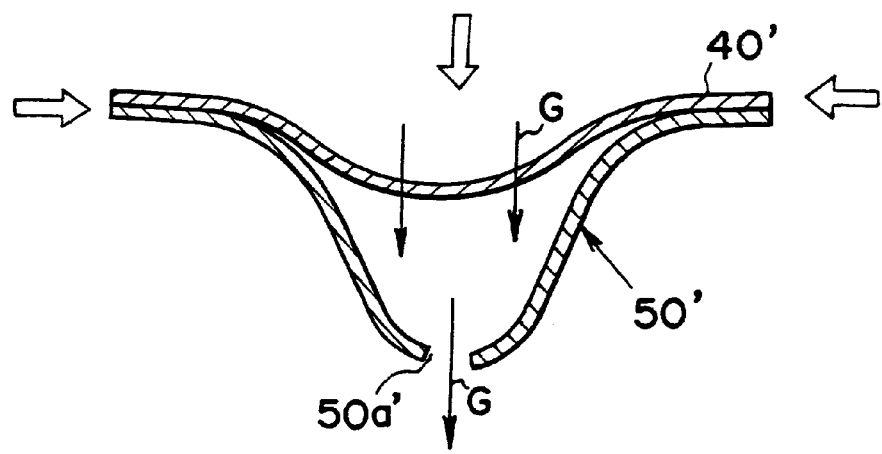
FIG. 49 is an operational view of FIG. 48.
Figure 50:
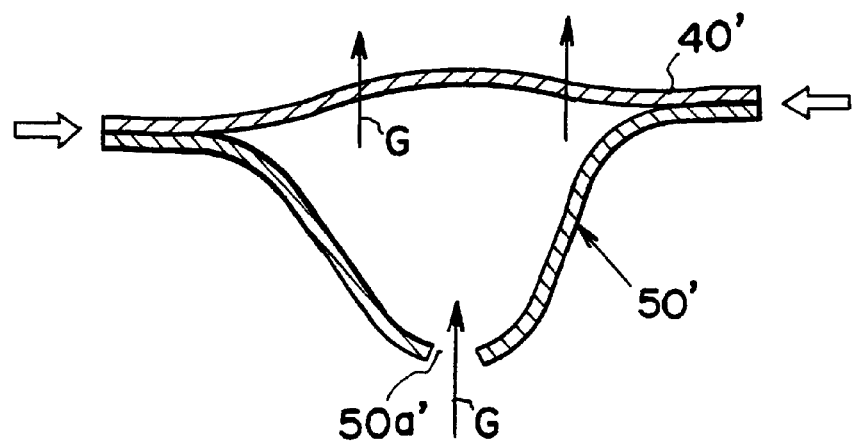
FIG. 50 is still another operational view of FIG. 48.

FIG. 48 through FIG. 50 show a twenty-first embodiment of a valve for use in a physical protector of the invention, which is formed by joining a relatively soft seal member 40' having gas permeability to another relatively rigid dome-shaped seal member 50'. The other seal member 50' is provided in its central portion with a vent slit 50a' of a normally-closed type.

In this embodiment, by pressing the seal member 40' while pressing laterally the other seal member 50' as shown in FIG. 49, the fluid G in the space between the both seal members 40' and 50' is allowed to flow out. As shown in FIG. 50, only by pressing laterally the other seal member 50' to open the vent slit 50a', the fluid G is released through the vent slit in the seal member 50' and allowed to pass through the seal member 40'.

Figure 51:
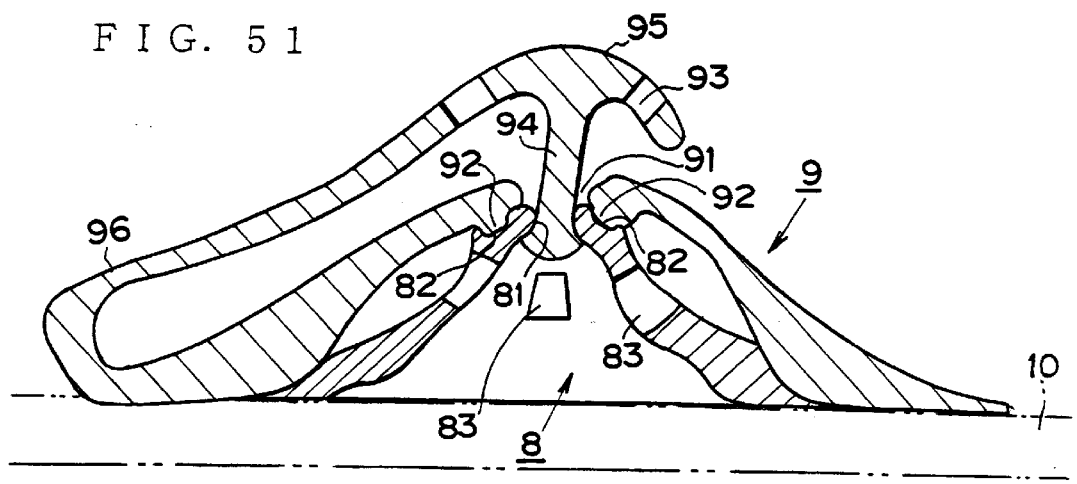
FIG. 51 is a sectional view showing a twenty-second embodiment of a valve of a physical protector according to this invention.
Figure 52:
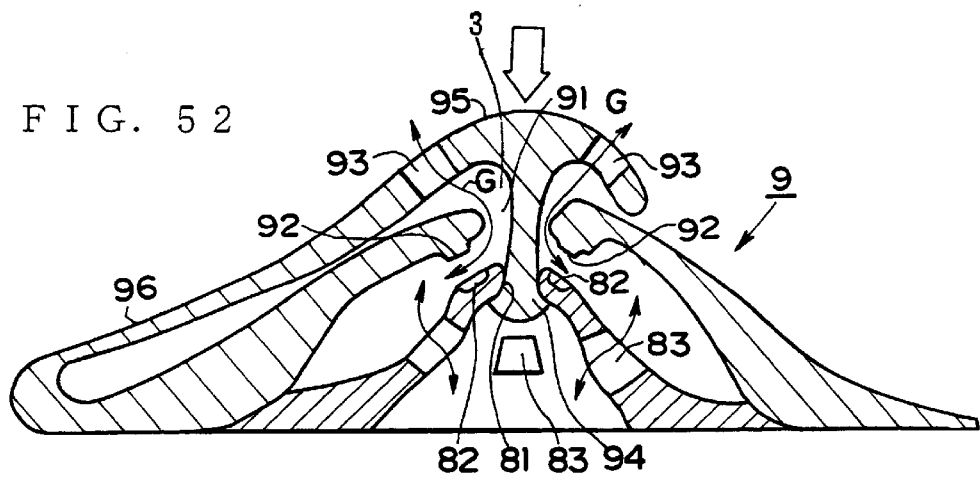
FIG. 52 is an operational view of FIG. 51.
Figure 53:
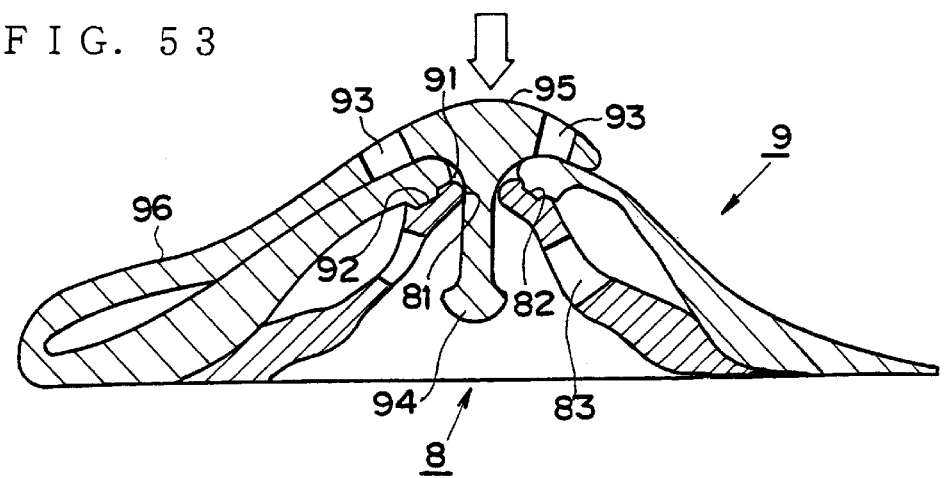
FIG. 53 is still another operational view of FIG. 51.

FIG. 51 through FIG. 53 show a twenty-second embodiment of a valve for use in a physical protector of the invention, which comprises a hollow bulged seal member 8 of relatively soft synthetic resin, and another hollow bulged seal member 9 of relatively rigid synthetic resin.

The seal member 8 is provided in its central peak portion with a connection hole 81 around which an engaging groove 82 is formed, and in its peripheral portion with vent holes 83. The other seal member 9 to be assembled so as to cover the seal member 8 has a central peak portion with a connection hole 91 and a lower surface with an engaging projection 92, and is connected to a cap 95 through a connection piece 96. The cap 95 has vent holes 93 and a projected shaft 94 to be fitted in the vent hole 91 and the aforesaid connection hole 81.

In this embodiment, by depressing the cap 95 of the seal member 9 as shown in FIG. 52, the seal member 8 and the other seal member 9 are deformed to form an air passage 3. By further depressing the cap 95 of the seal member 9 as shown in FIG. 53, the air passage 3 is closed, while closing the connection hole 91 of the seal member 9. Thus, the sealing performance of the valve can be heightened and is suitable for use in the places requiring waterproofness. The other operations and effects are the same as those of the first embodiment as mentioned above.

Figure 54:
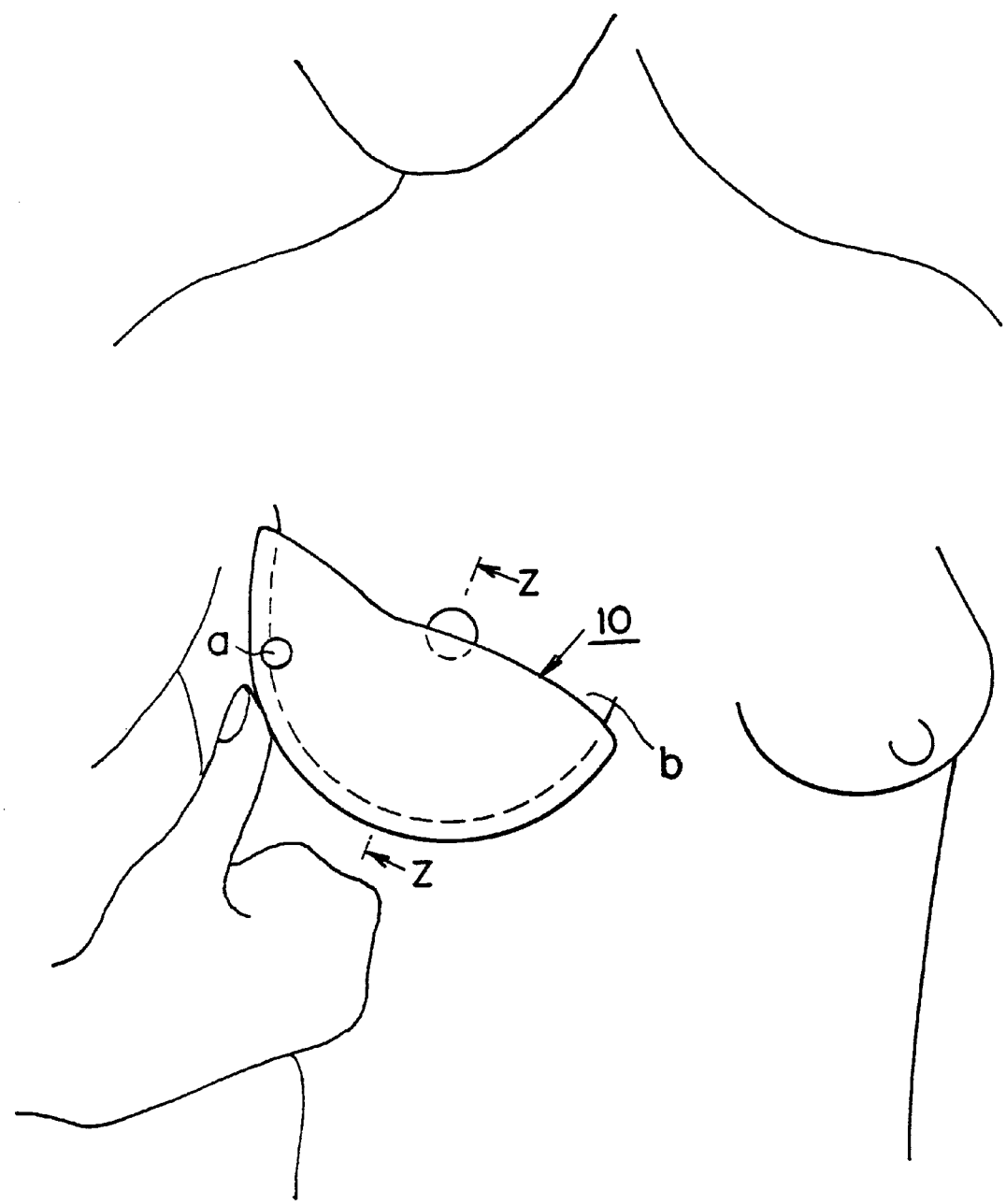
FIG. 54 is a sectional view showing a first embodiment of a physical protector according to this invention in use.
Figure 55:
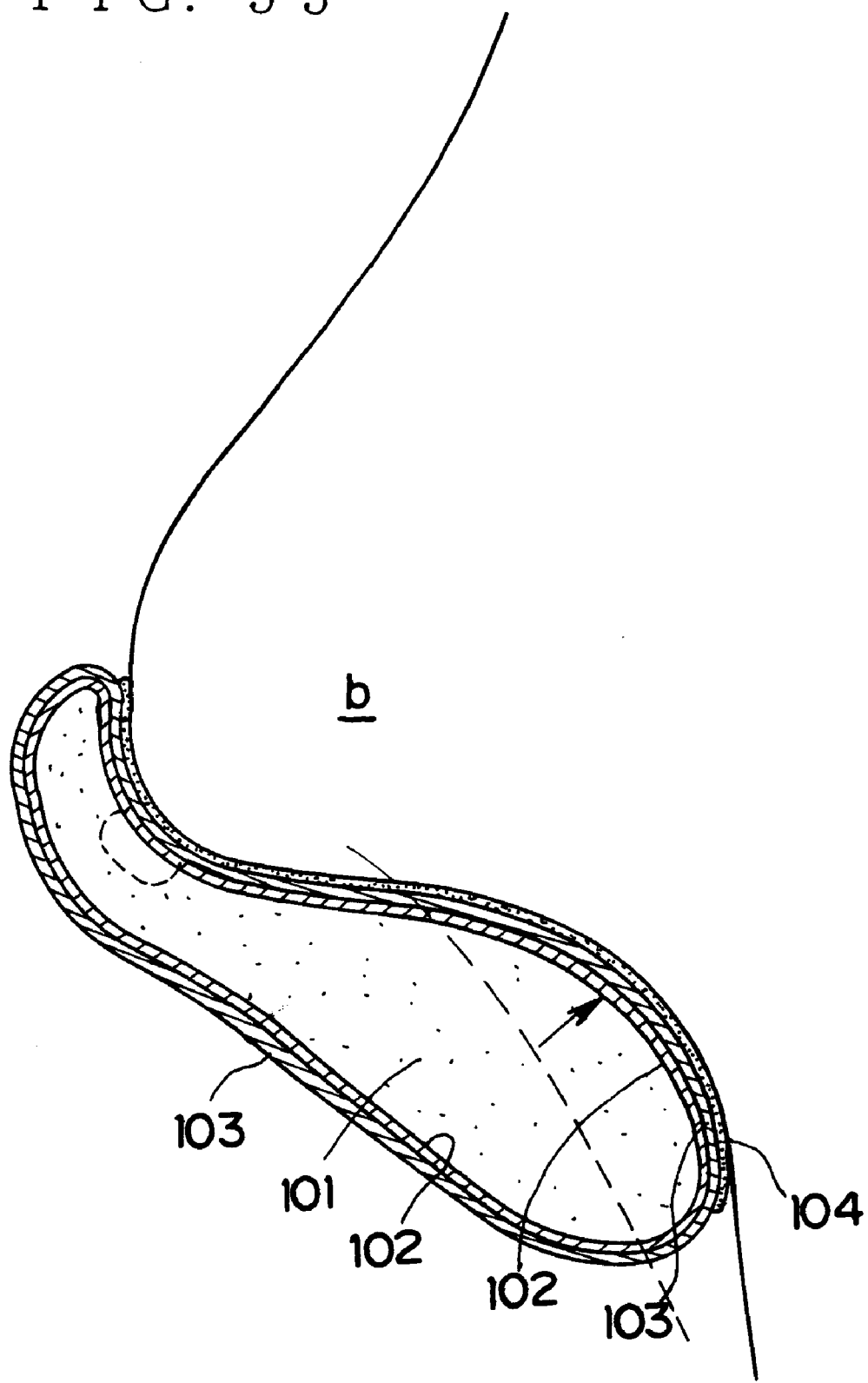
FIG. 55 is a section taken on line 55—55 in FIG. 54.

FIG. 54 and FIG. 55 show a first embodiment of a physical protector of the invention in use.

In this embodiment, any of the valves a in the aforementioned first to nineteenth embodiments is attached to the bag member 10 to open and close the bag member 10, so that the protector can be used as a breast pad. The valve a is fixed onto the bag member 10 as shown in FIG. 1 to FIG. 51. Although the valve a is placed on the one end portion of the breast pad in the illustrated embodiment, it may be disposed on any position at which it can be depressed easily.

In this embodiment, as shown in FIG. 55, a foamed expandable material 101 such as of polyurethane is accommodated in a gas-barrier synthetic resin film bag 102 in the compressed state. The breast pad is covered with a flexible cover member 103, and one side surface thereof is further covered with an adhesive layer 104. The laminated synthetic resin film 102 and cover member 103 is provided with an opening 105 as shown in FIG. 1. Over the opening 105, the valve a is disposed.

In this embodiment, by opening the valve a, the material 101 expandable with air expands spontaneously as shown in FIG. 55. The expanded bag member 10 inserted between the breast b and a brassiere has a cushion effect to keep the woman's breast b in the well-shape. The expansion of the bag member 10 can be adjusted by controlling the valve a to expand the foamed expandable material 101. That is, the bag member 10 may be formed to various shapes so as to be put onto the breast b at desirable angles in accordance with the state in which the valve opens. Thus, various forms of the bag member can be selected. Particularly, the bag member provided with the valve a of the fourth embodiment can be adjusted in thickness by depressing the valve a in the state of the bag member attached to the breast b.

As shown in FIG. 54, the bag member 10, when not used, is pressed while pushing the valve a to discharge the air out of the bag member 10. This discharge of the air can be utilized to adjust the cushion of the expanded bag member 10.

The bag member of this embodiment can be detachably attached to or inserted into a brassiere or other clothes including swimsuits and sports suits. In the illustrated embodiment, the adhesive layer 104 is attached to the breast's side of the bag member, but it may be attached to the other brassiere's side to be permitted to adhere to the brassiere. The bag member 10 has not only the shape keeping function, but also cushioning and heat-retaining functions. This bag member can be used integrally with a brassiere or underwear, though not illustrated.

Figure 56:
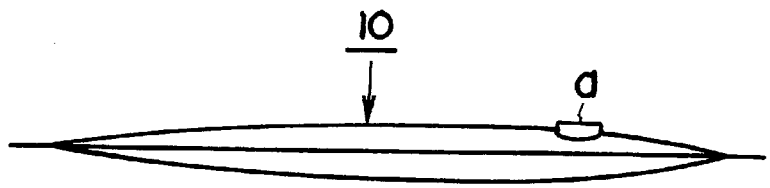
FIG. 56 is a developed view of a second embodiment of a physical protector according to this invention.
Figure 57:
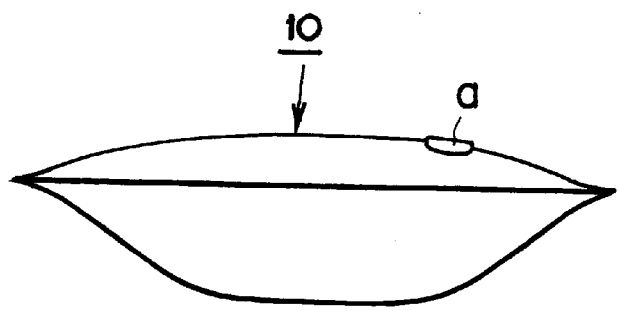
FIG. 57 is a view showing the protector of FIG. 56 in use.
Figure 58:
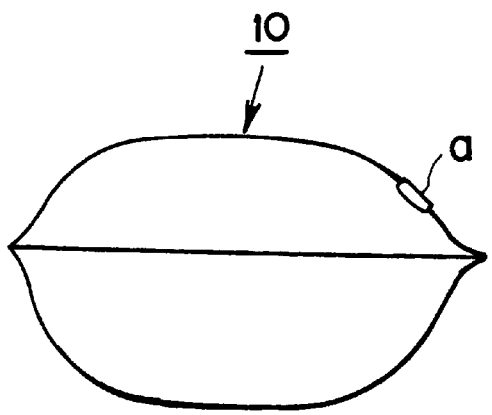
FIG. 58 is a side view of FIG. 56.

FIG. 56 through FIG. 58 show a second embodiment of a physical protector of the invention, in which the bag member 10 of the aforesaid first embodiment is more expansible on its back side (side to touch the breast b) than on its front side. FIG. 56 shows the contracted state, FIG. 57 shows the state in which the bag member is expanding, and FIG. 58 shows the fully inflated state.

Figure 59:
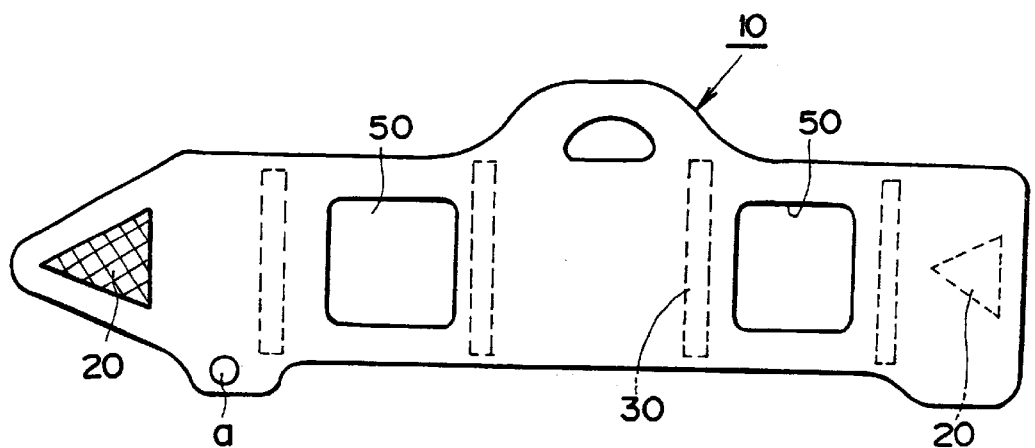
FIG. 59 is a developed view of a third embodiment of a physical protector according to this invention.
Figure 60:
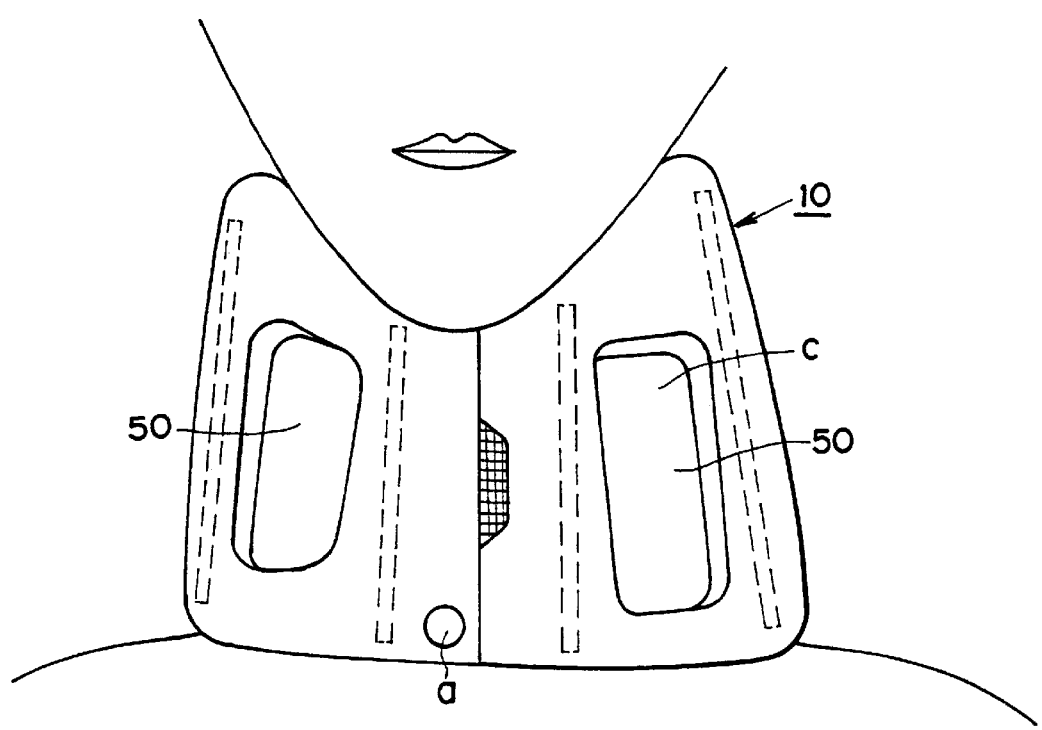
FIG. 60 is a view showing the protector of FIG. 59 in use.
Figure 61:
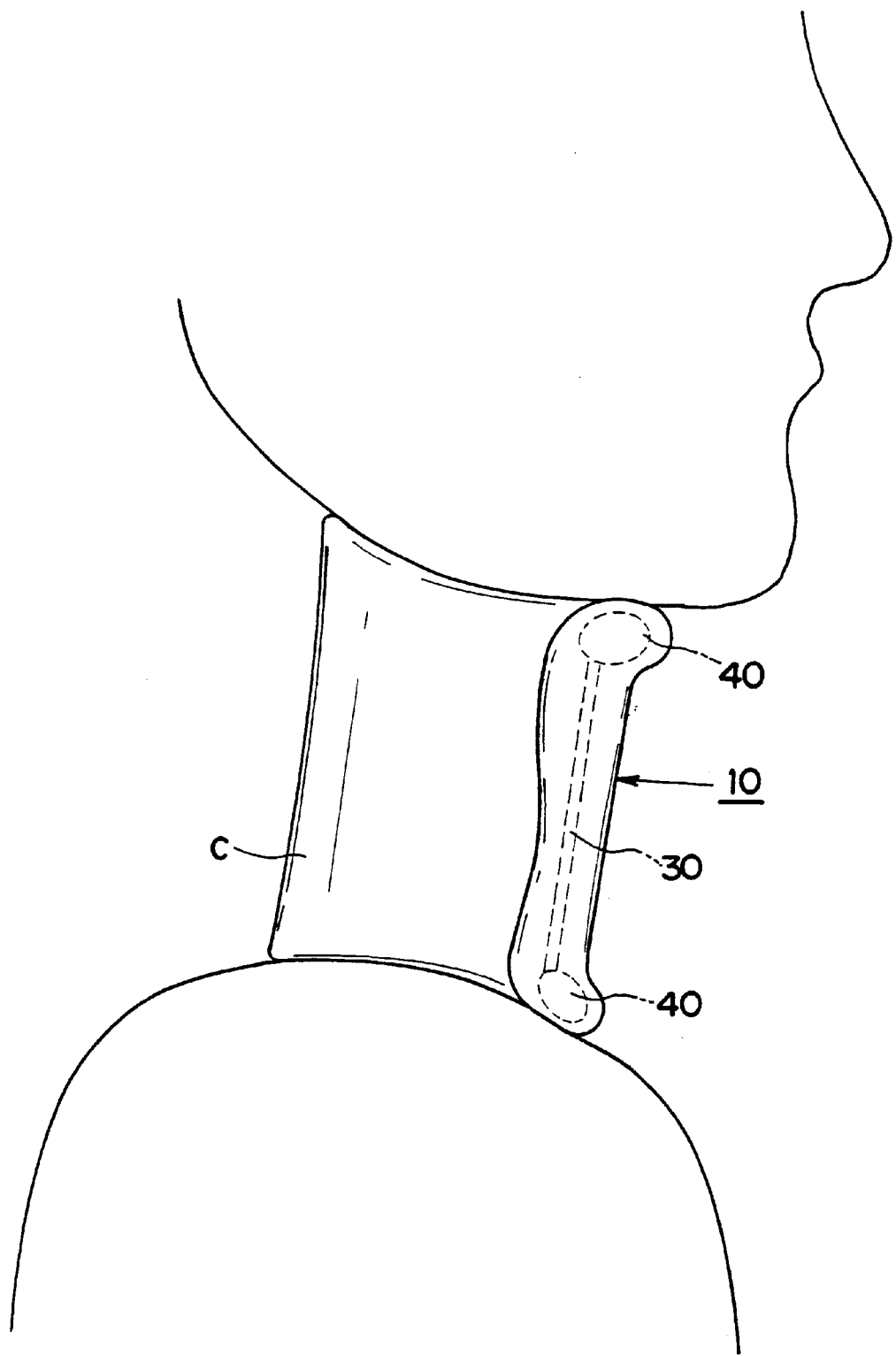
FIG. 61 is a side view of FIG. 59.

FIG. 59 through FIG. 61 show a third embodiment of the physical protector of the invention, in which the bag member 10 can be suitably used as a plaster cast for a neck c. The bag member 10 serving as the plaster cast is formed in a slender belt so as to be wound around the neck c and provided on both its ends with surface fasteners such as Velcro's Magic Tape. The valve a is disposed on the lower portion of the front surface of the bag member so as to be easily operated. To retain the shape of the bag member 10 serving as the plaster cast, a plurality of reinforcing members 30 are disposed in the width direction of the bag member. The reinforcing member itself has a shape-retaining effect. At both end portions of the reinforcing member, pads 40 may be provided so as to softly support the chin or other portions. The bag member 10 serving as the plaster cast may have ventilation openings 50.

According to this embodiment, the bag member can be desirably inflated by operating the valve a to expand the foamed expandable material in the state wound around the neck. The inflated bag member can be retained in vertical shape by means of the reinforcing members 30.

Figure 62:
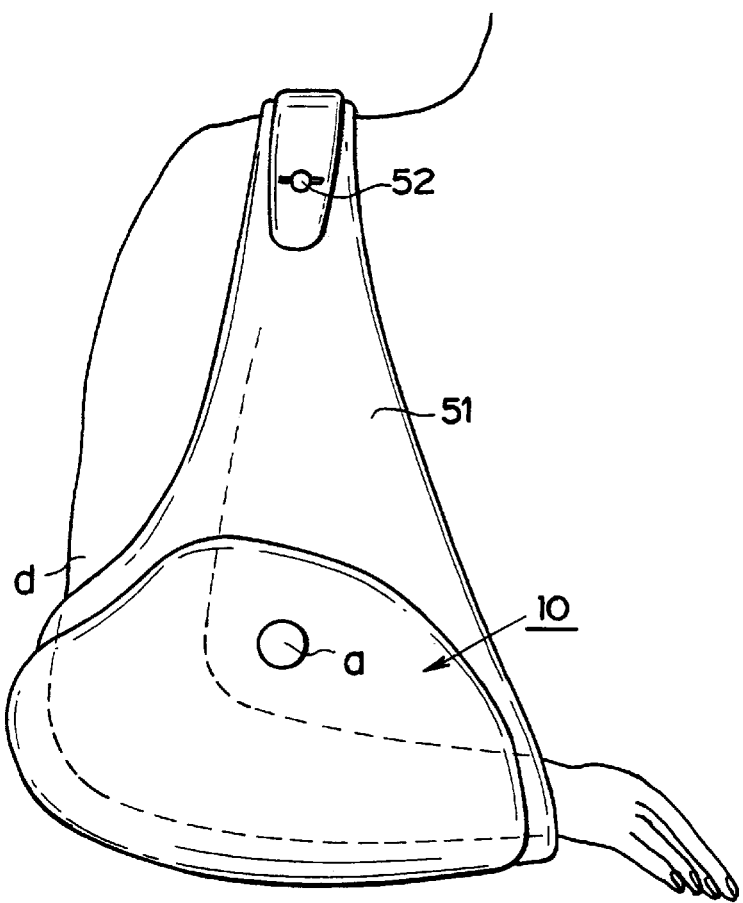
FIG. 62 is a developed view of a fourth embodiment of a physical protector according to this invention.
Figure 63:
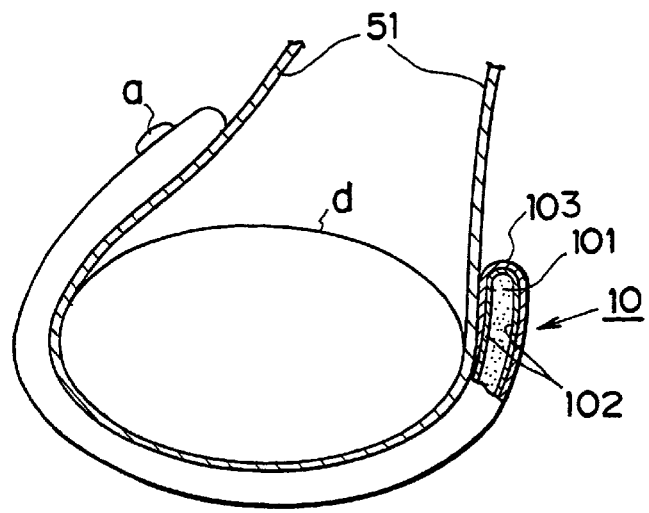
FIG. 63 is a sectional view of FIG. 62.

FIG. 62 and FIG. 63 show a fourth embodiment of a physical protector of the invention, which comprises a bag member 10 serving as a sling for an arm d. The sling comprises a band 50 having a shape and length capable of suspending the arm d and the bag member 10 attached to the wider portion of the band 50 and having the shape capable of enclosing the arm. Both ends of the band 50 can be fastened together by fastener 52. The bag member 10 can be inflated to protect the arm as required.

Figure 64:
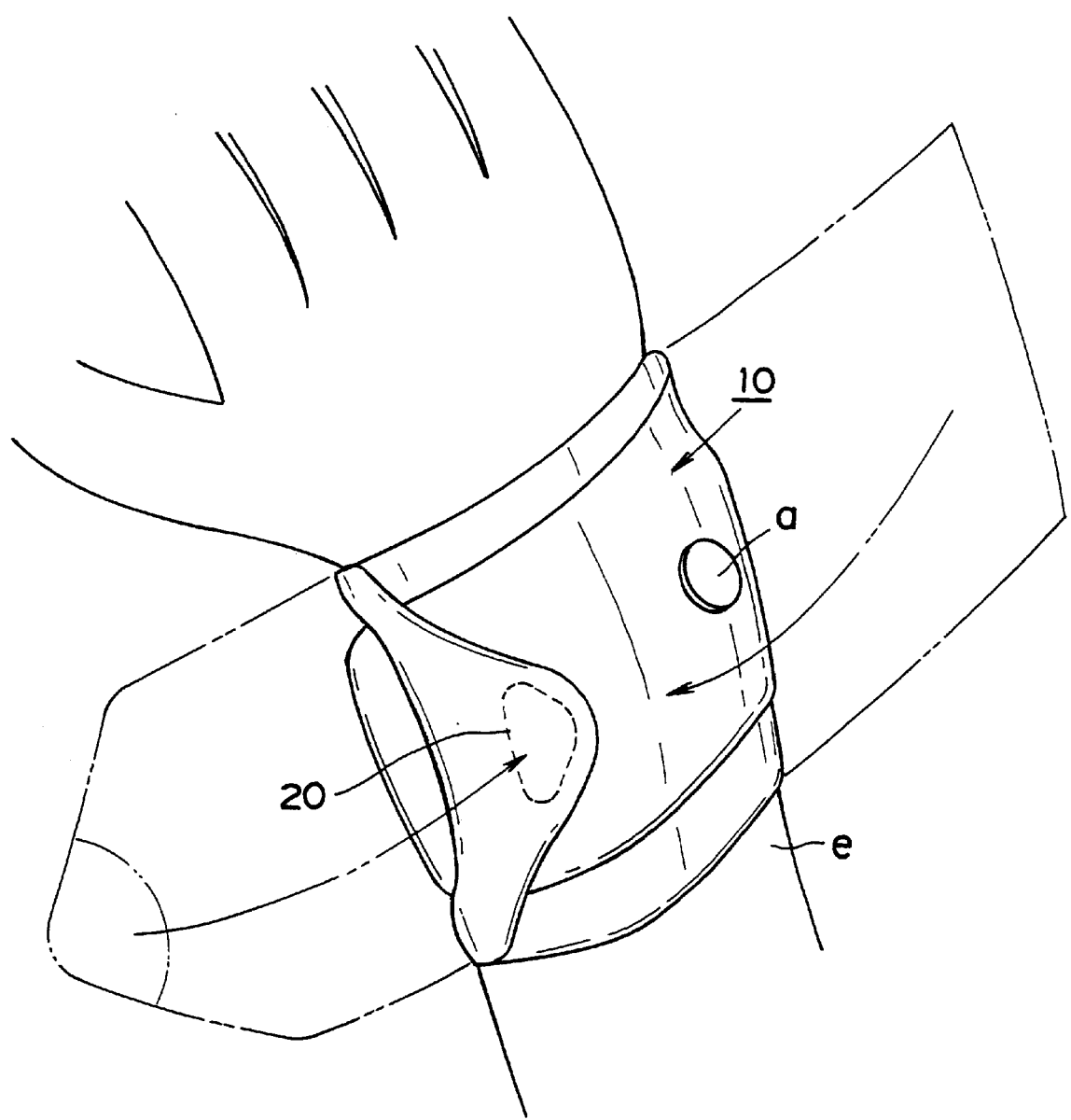
FIG. 64 is a view showing a fifth embodiment of a physical protector according to this invention in use.

FIG. 64 shows a fifth embodiment of a physical protector of the invention, which comprises a bag member 10 serving as a supporter for a wrist e. That is, the bag member 10 serving as the supporter is formed of a slender belt which is wound around the knee and retained by surface fasteners such as Velcro's Magic Tape. The wrist e can be protected by operating the valve a mounted on the front of the bag member to inflate the bag member.

Figure 65:
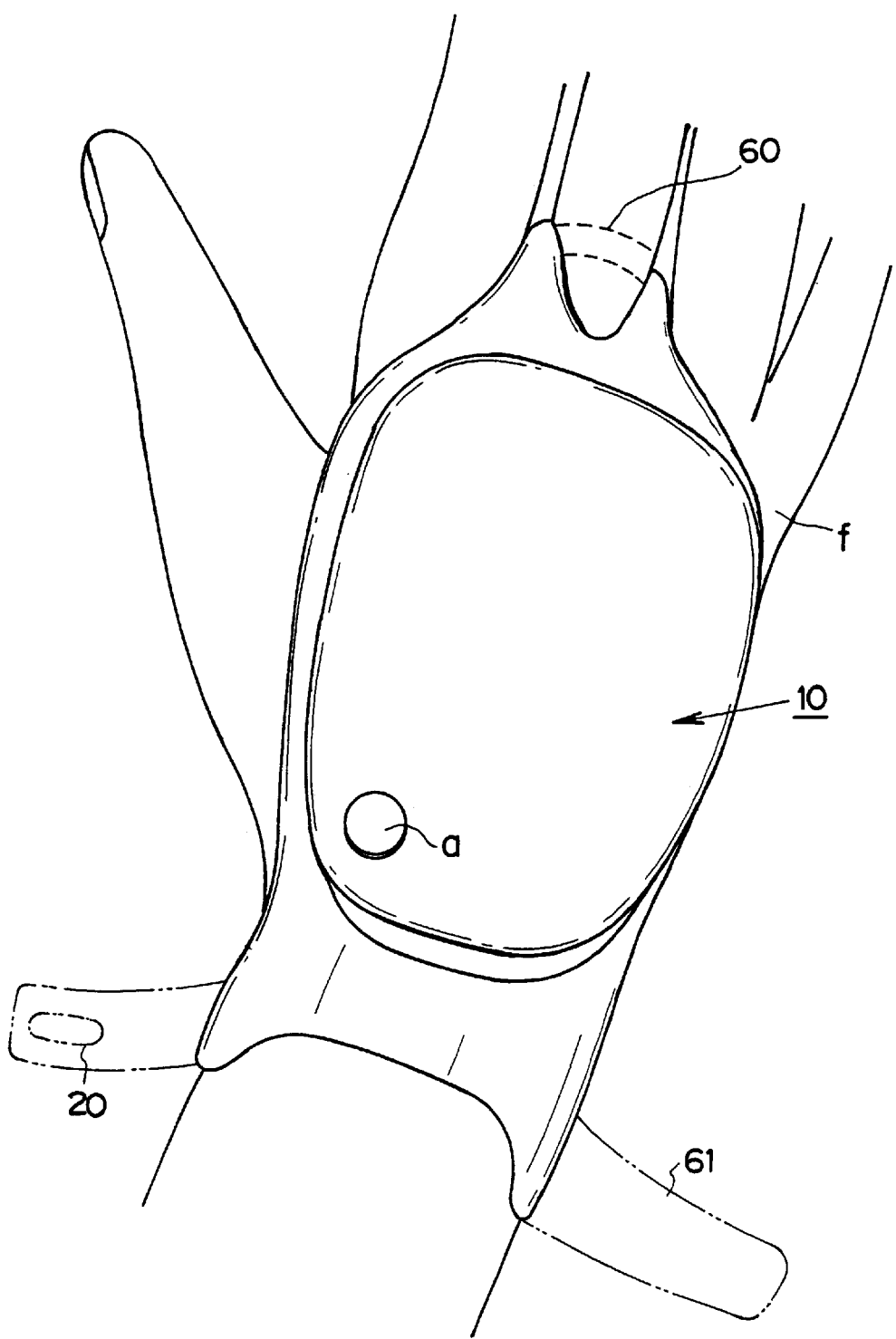
FIG. 65 is a view showing a sixth embodiment of a physical protector according to this invention in use.

FIG. 65 shows a sixth embodiment of a physical protector of the invention, which is suitable as a supporter for the hand's back f. The supporter of this embodiment has a valve a on the side portion of the bag member 10. The supporter is provided with a finger ring 60 and fastening belts 61 which may be formed of surface fasteners 20 such as Velcro's Magic Tape. According to this embodiment, the hand's back f can be protected and serve as a warmer for the hand's back.

Figure 66:
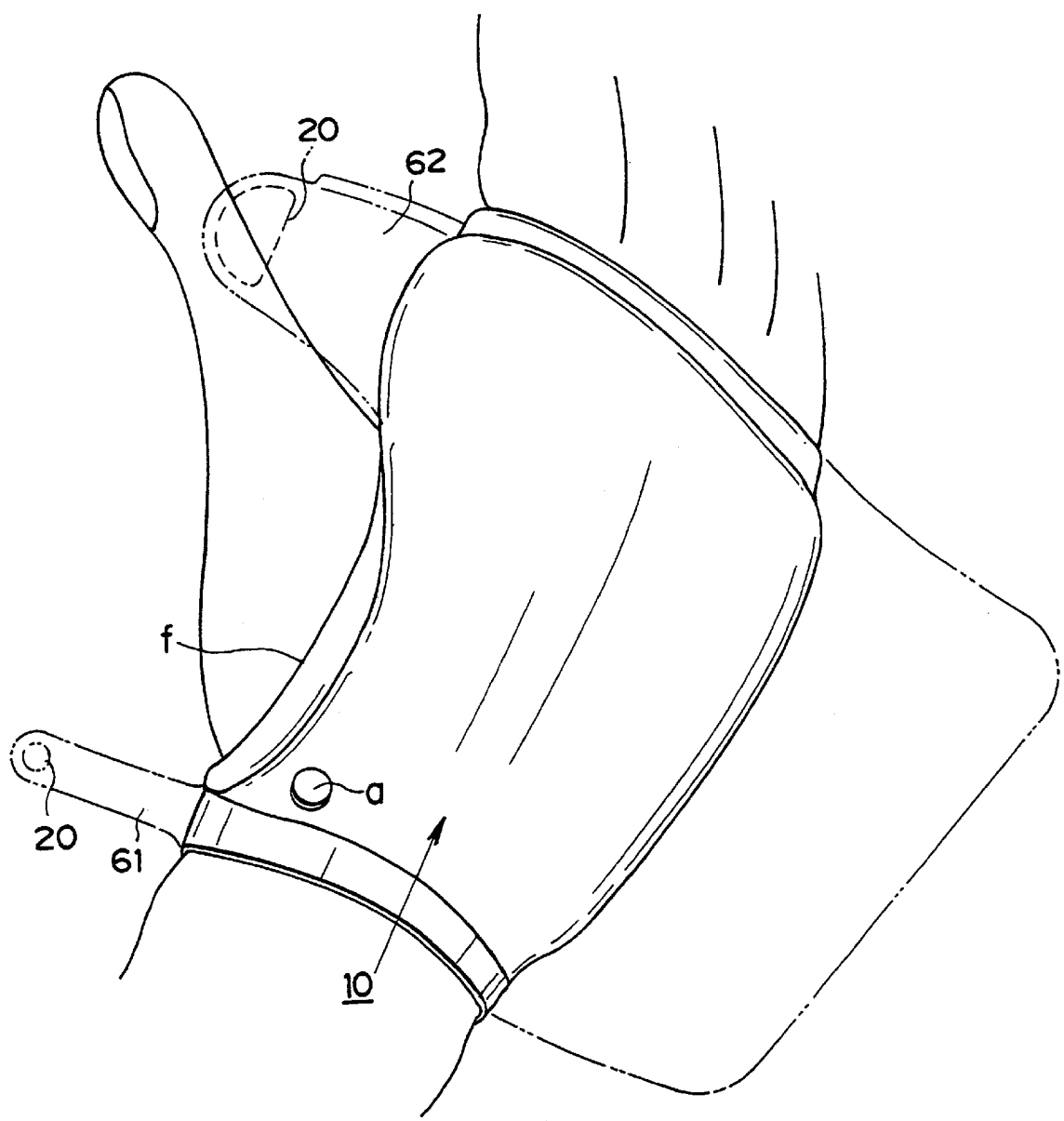
FIG. 66 is a view showing a seventh embodiment of a physical protector according to this invention in use.

FIG. 66 shows a seventh embodiment of a physical protector of the invention, as a modified form of the aforesaid sixth embodiment, wherein the finger ring 60 is omitted. That is, this embodiment employs upper and lower fastening belts 62 and 61 each having surface fasteners 20 such as Velcro's Magic Tape to be fastened. The bag member 10 of this embodiment has sufficient size to envelop the hand's back f to the palm. Thus, this embodiment can protect to a large extent.

Figure 67:
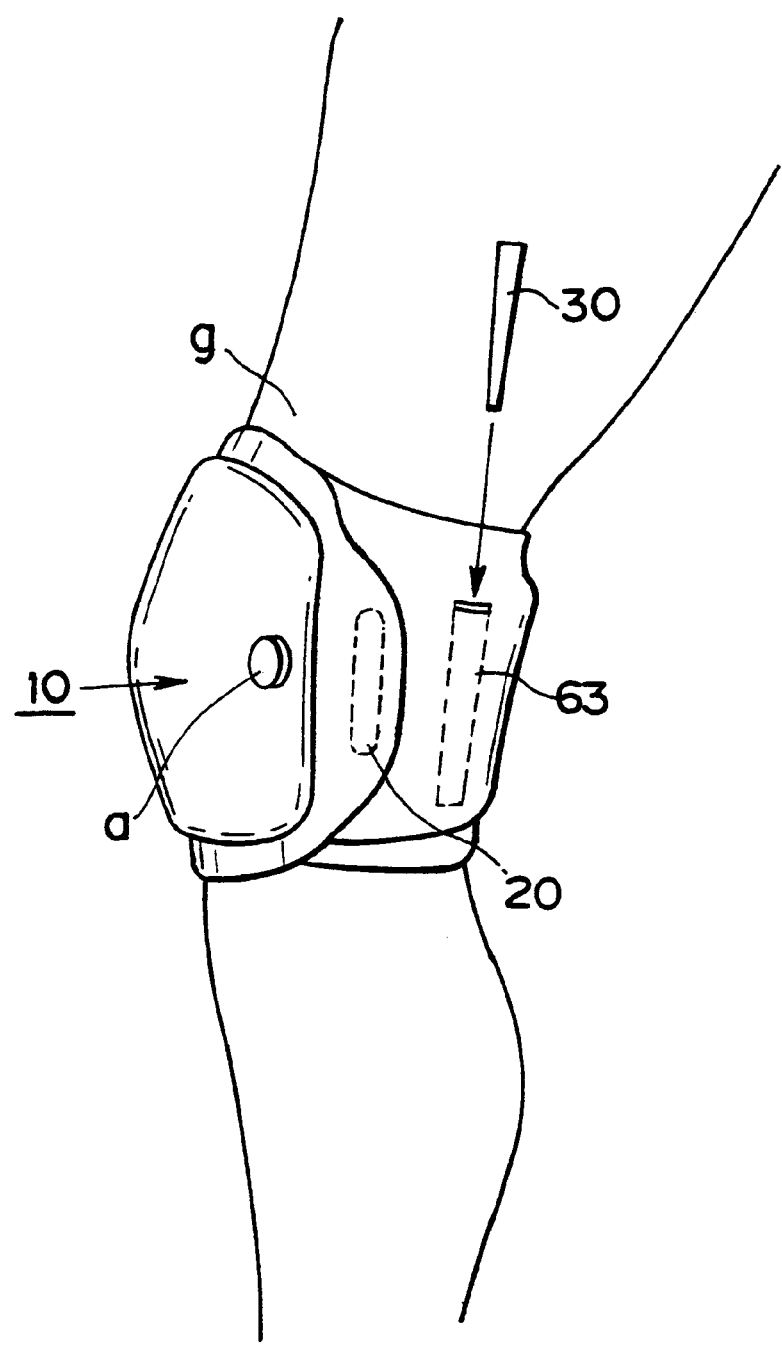
FIG. 67 is a view showing an eighth embodiment of a physical protector according to this invention in use.

FIG. 67 shows an eighth embodiment of a physical protector of the invention, which comprises a bag member 10 used as a supporter for the knee g. This embodiment has a pocket 63 for removably accommodating a reinforcing member 30. It is preferable to form a plurality of the pockets 63 around the supporter, so that the reinforcing members 30 can be selectively inserted in the desired pockets.

Figure 68:
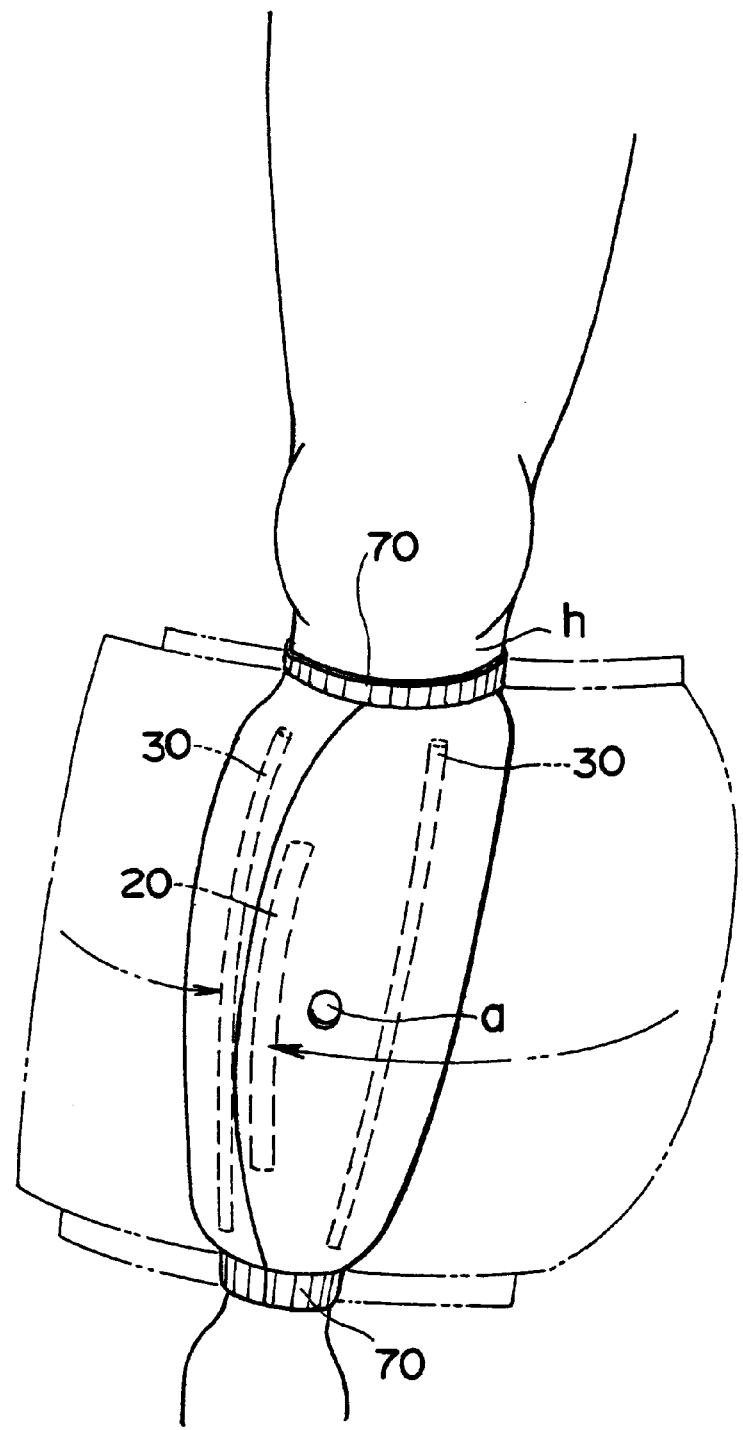
FIG. 68 is a view showing a ninth embodiment of a physical protector according to this invention in use.

FIG. 68 shows a ninth embodiment of a physical protector of the invention, which comprises a bag member 10 used as a supporter for the calf h. The bag member 10 in this embodiment is shaped in a substantially square and has upper and lower tightening bands 70 having good stretchability so as not to slip off.

Figure 69:
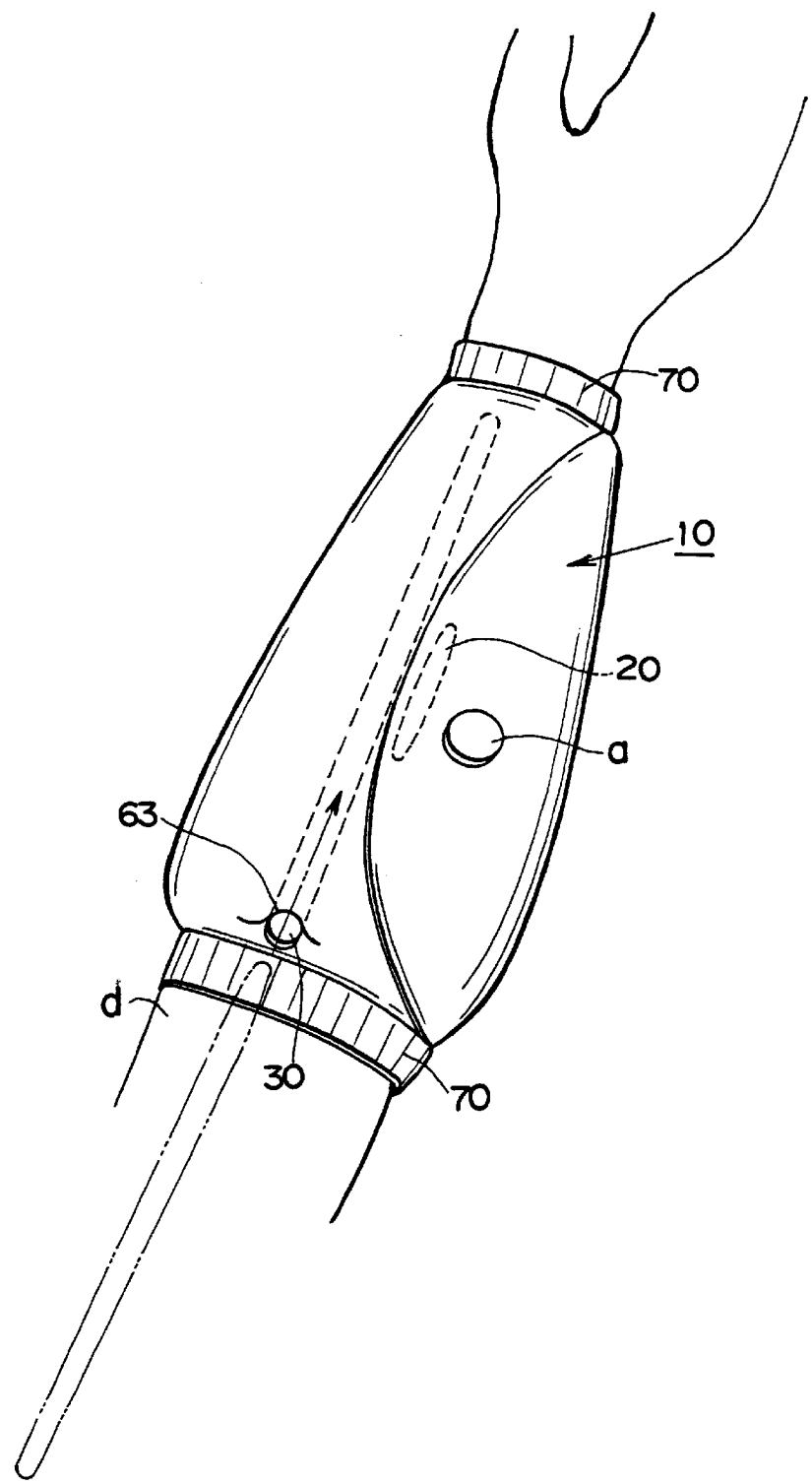
FIG. 69 is a view showing a tenth embodiment of a physical protector according to this invention in use.

FIG. 69 shows a tenth embodiment of a physical protector of the invention, which can be suitably used as a supporter for an arm d. In this embodiment, a reinforcing member 30 can be removably inserted into a pocket 63. Also, this embodiment has tightening bands 70.

Figure 70:
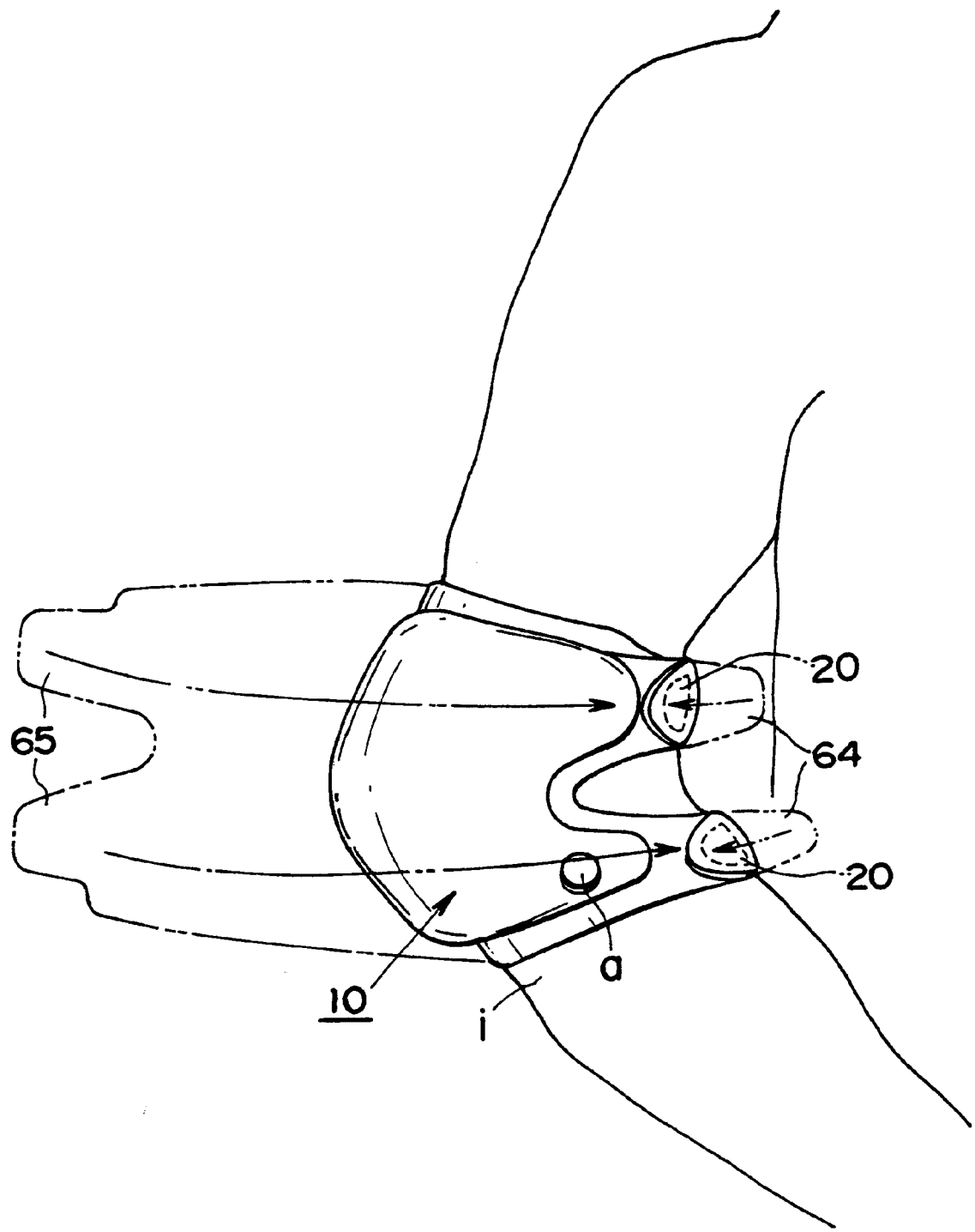
FIG. 70 is a view showing an eleventh embodiment of a physical protector according to this invention in use.

FIG. 70 shows an eleventh embodiment of a physical protector of the invention, which can be suitably used as a supporter for an elbow i. The bag member 10 serving as the supporter has fork-like bands 64 and 65 for extending to the inside of the elbow i, so that the bag member is fixed onto the outside of the elbow. According to this embodiment, the elbow i whose outside is widely protected by the bag member, can be easily bent due to the fork-like bands 64 and 65.

Figure 71:
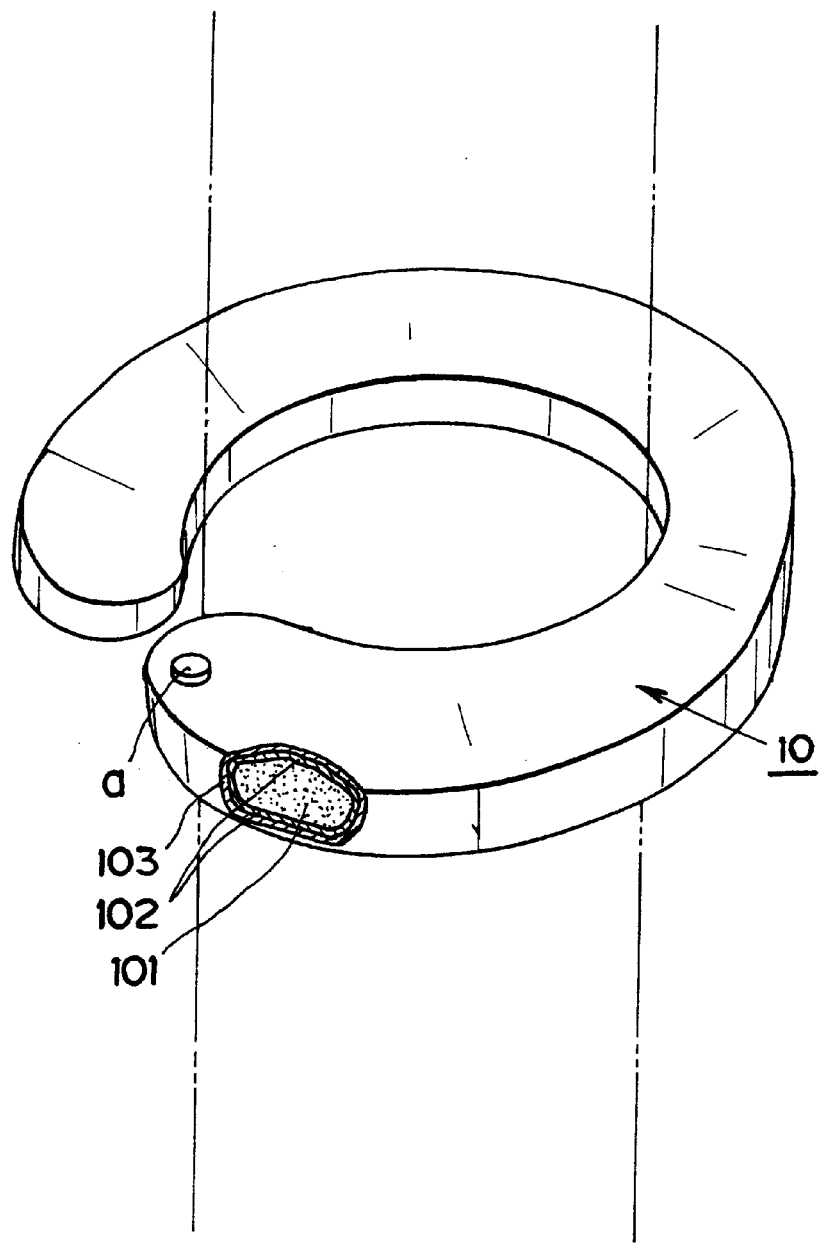
FIG. 71 is a view showing a twelfth embodiment of a physical protector according to this invention in use.

FIG. 71 shows a twelfth embodiment of a physical protector of the invention, which can be suitably used for various purposes. The bag member 10 in this embodiment is formed in a ring, so that various physical parts can be inserted therethrough or various mechanical articles can be fitted thereinto. It is preferable to inflate the bag member by operating the valve a upon placing an object to be protected in the bag member before inflation. Also, the bag member may be formed in a full circle so as to be used as a swimming ring. Thus, the use of the protector of the invention can be widened.

Figure 72:
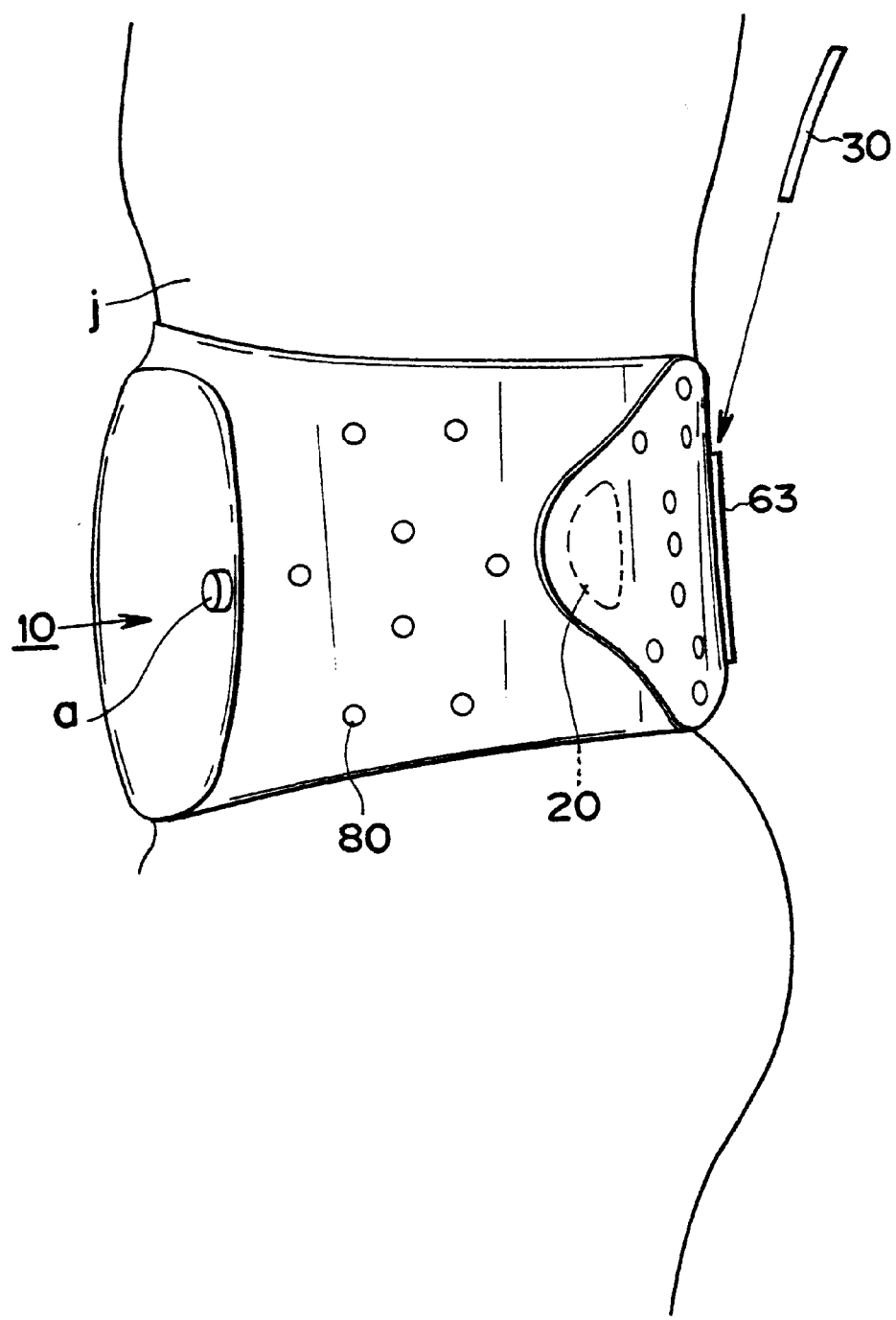
FIG. 72 is a view showing a thirteenth embodiment of a physical protector according to this invention in use.

FIG. 72 shows a thirteenth embodiment of a physical protector of the invention, which can be suitably used as a supporter for the trunk j. The bag member 10 serving as the supporter is formed in a belt and has a pocket 63 into which a reinforcing member 30 can be removably inserted in the width direction of the bag member. Also, the bag member has fastening means 20. The bag member further has lots of ventilation holes 80 for preventing eczema caused by perspiration.

Figure 73:
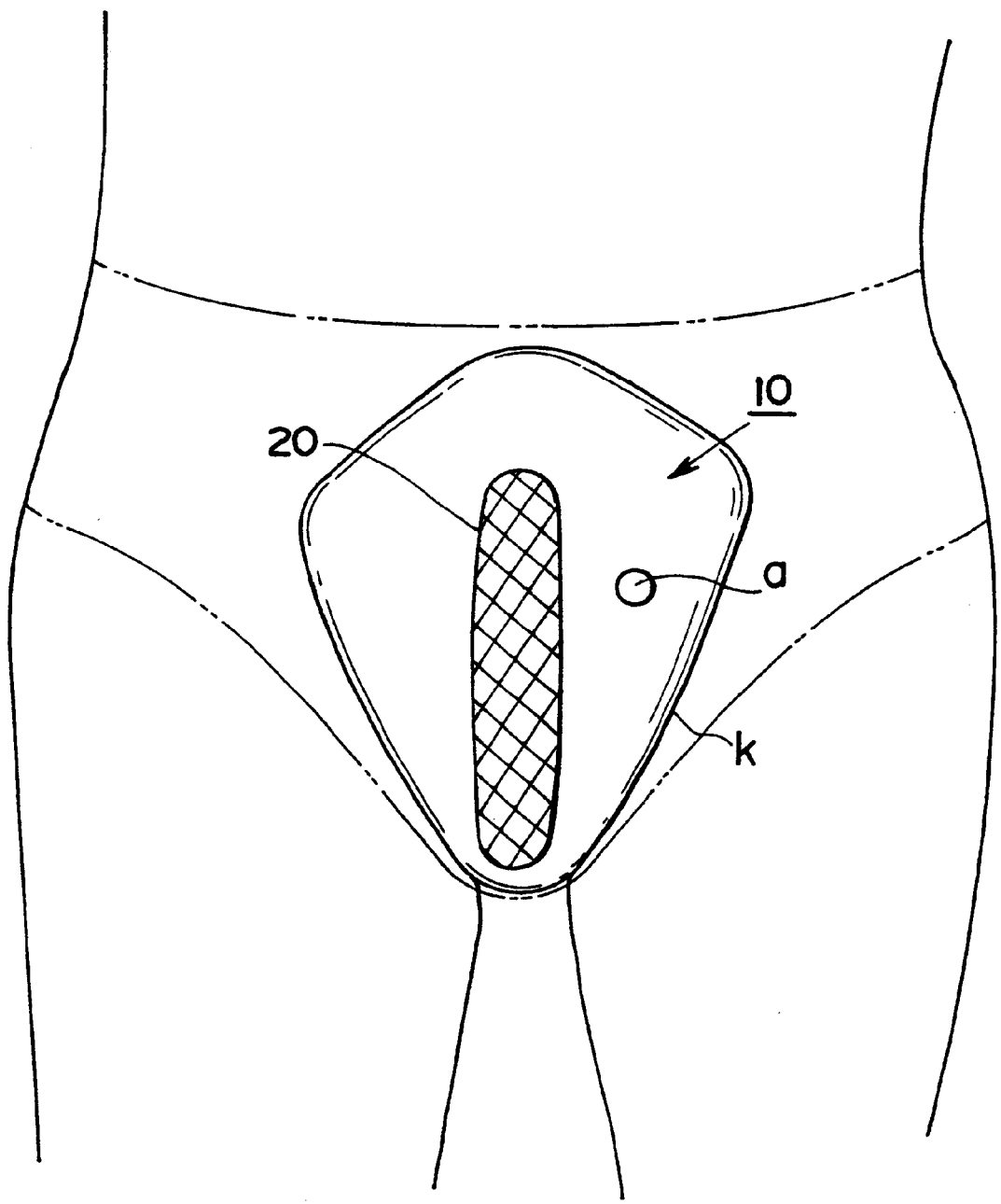
FIG. 73 is a view showing a fourteenth embodiment of a physical protector according to this invention in use.

FIG. 73 shows a fourteenth embodiment of a physical protector of the invention, which can be suitably used as a supporter for a crotch k. This embodiment is provided on it's outside with a surface fastener 20 such as Velcro's Magic Tape so as to be secured in position to underwear or the like. Instead of the surface fastener 20, an adhesive layer may be attached thereto, though not shown. The bag member 10 serving as the supporter can be used as various protectors for sports.

Figure 74:
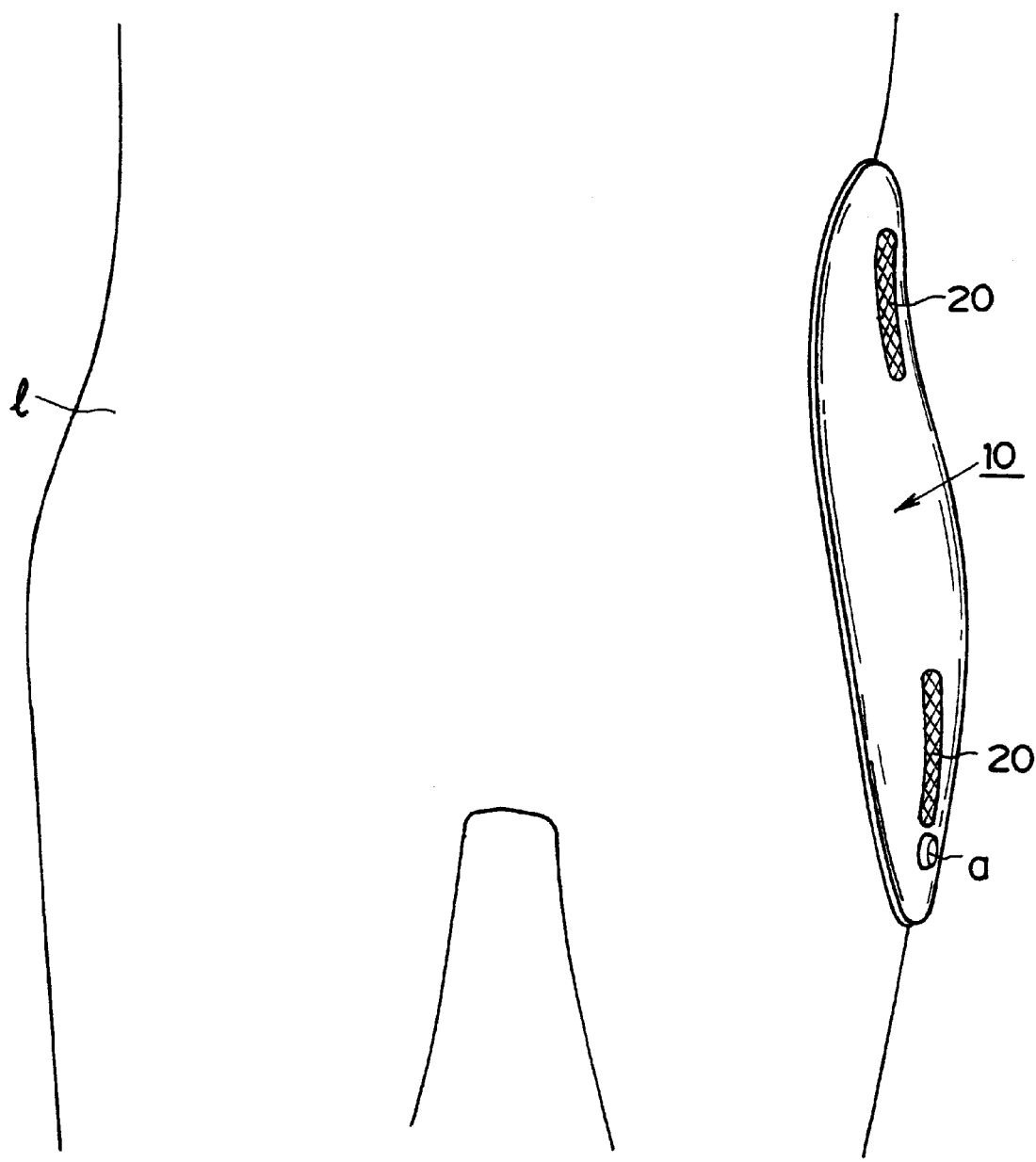
FIG. 74 is a view showing a fifteenth embodiment of a physical protector according to this invention in use.

FIG. 74 shows fifteenth embodiment of this invention, which can be suitably used as a supporter for the waist 1. The bag member 10 used as the supporter is formed in a slender oval shape and is provided on its outside with a surface fastener 20. The protector of this embodiment can be used as protectors of various types.

Figure 75:
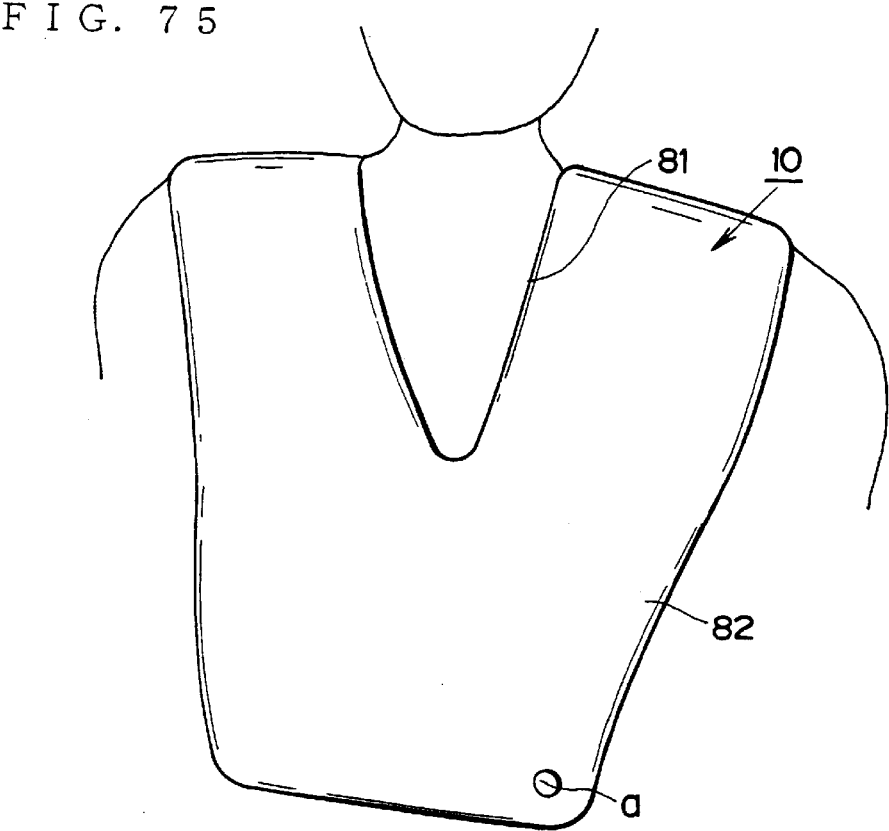
FIG. 75 is a view showing a sixteenth embodiment of a physical protector according to this invention in use.

FIG. 75 shows a sixteenth embodiment of this invention, which can be suitably used as a life jacket for use in airplanes and ships. The bag member serving as the life jacket has a V-shaped opening 81 through which the neck c is inserted and covers members 82 to be attached to the chest and back. The expansion of this bag member can be controlled in accordance with the purposes for which this embodiment is used.

Figure 76:
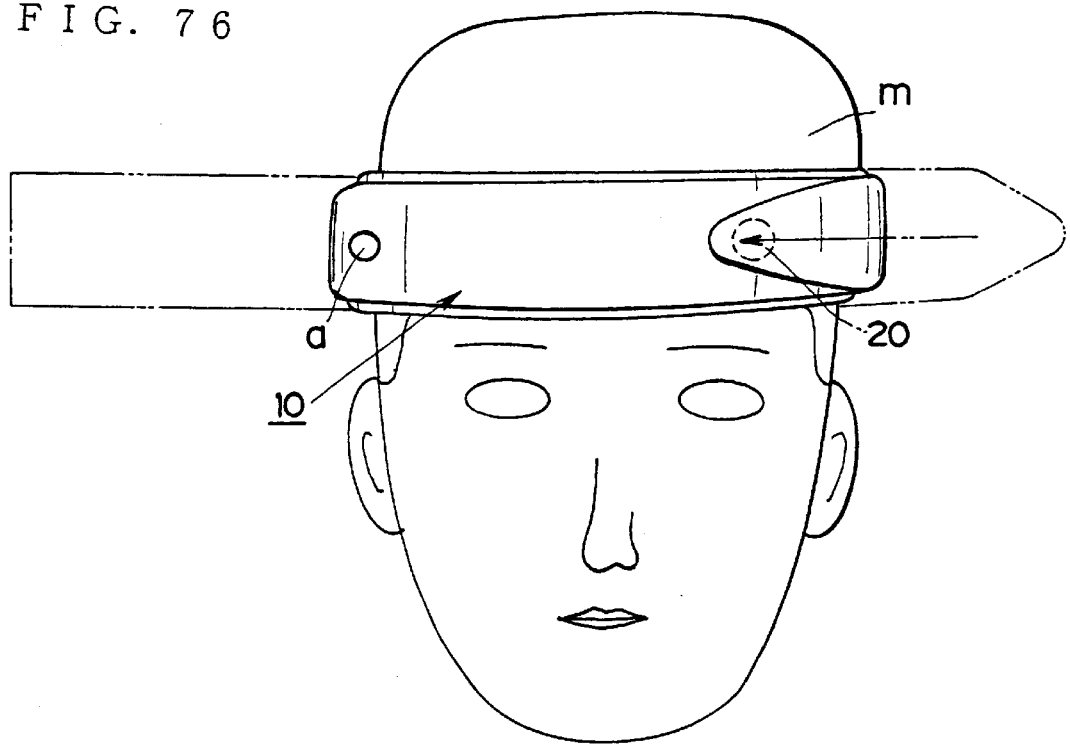
FIG. 76 is a view showing a seventeenth embodiment of a physical protector according to this invention in use.

FIG. 76 shows a seventeenth embodiment of this invention, which can be suitably used as a supporter for the head m. The bag member 10 of this embodiment is formed in a slender headband. By inflating the bag member 10 fastened with surface fasteners 20, the fastening strength of the headband can be adjusted.

Figure 77:
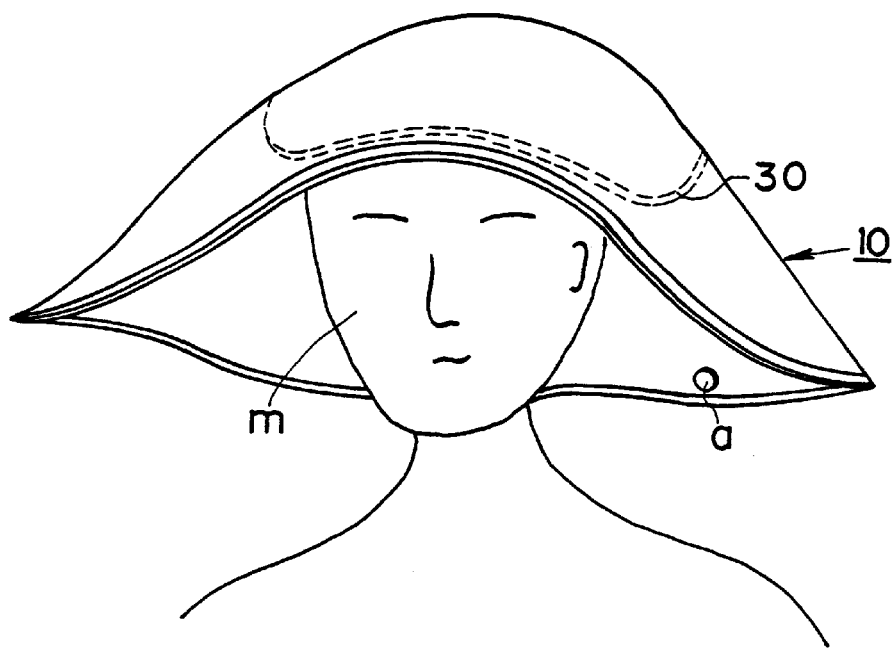
FIG. 77 is a view showing an eighteenth embodiment of a physical protector according to this invention in use.

FIG. 77 shows an eighteenth embodiment of this invention, which can be suitably used as a disaster hood. In the bag member 10 of this embodiment, a reinforcing member 30 of a curved plate is accommodated to improve the impact resistance thereof.

Figure 78:
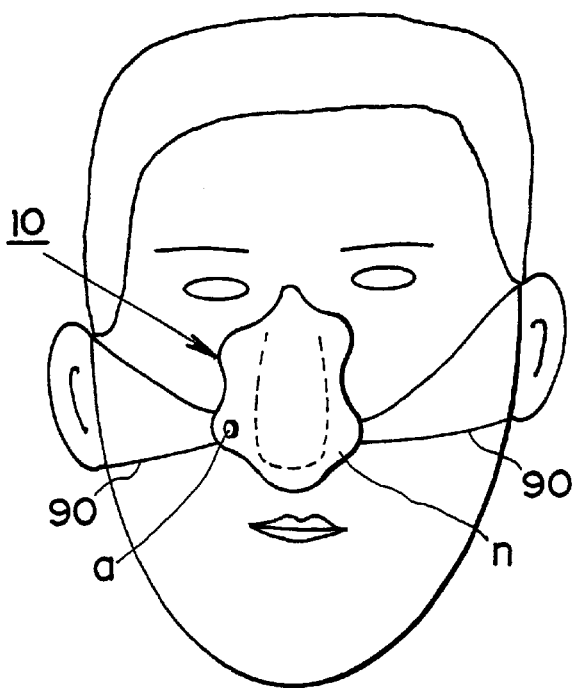
FIG. 78 is a view showing a nineteenth embodiment of a physical protector according to this invention in use.

FIG. 78 shows a nineteenth embodiment of this invention, which can be suitably used as a supporter for a nose n. The bag member 10 of this embodiment has ear straps 90.

Figure 79:
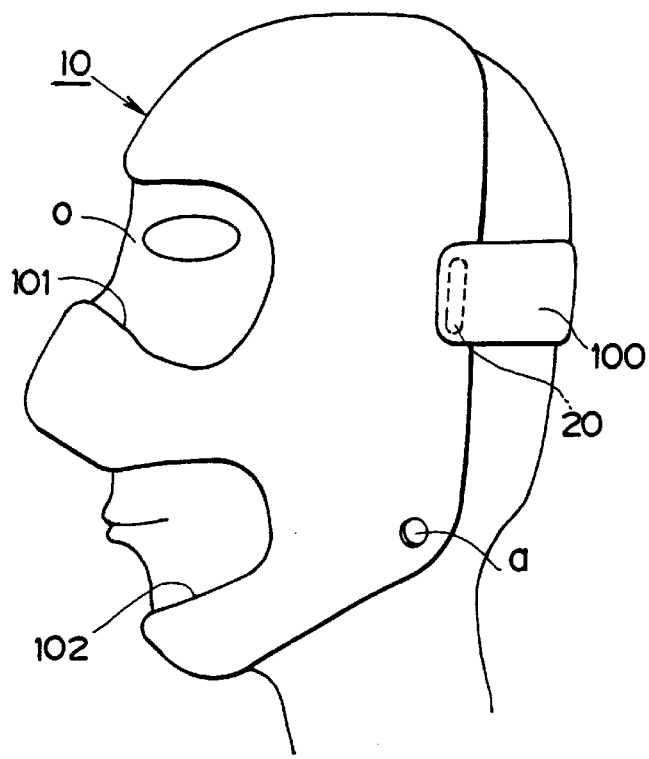
FIG. 79 is a view showing a twentieth embodiment of a physical protector according to this invention in use.

FIG. 79 shows a twentieth embodiment of this invention, which can be suitably used as a supporter for protecting substantially all of the area of a face o. The bag member of this embodiment is provided with a string-like fixing belt 100, and has an eye opening 101 and a mouth opening 102.

Figure 80:
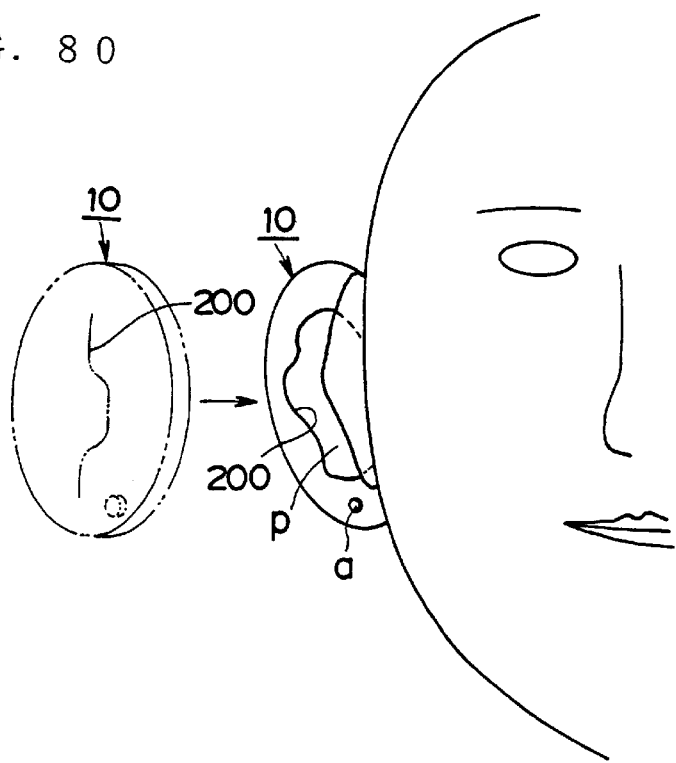
FIG. 80 is a view showing a twenty-first embodiment of a physical protector according to this invention in use.

FIG. 80 shows a twenty-first embodiment of this invention, which can be suitably used as a supporter for an ear p. The elliptic bag member 10 is formed in a spherical shape and has a cut 200 for accommodating the ear p. This embodiment has the functions of an earplug and an ear warmer.

Figure 81:
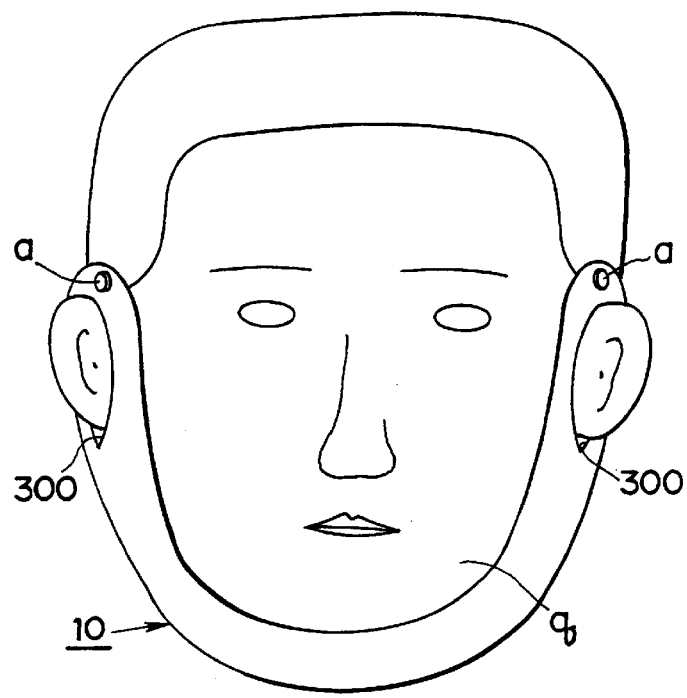
FIG. 81 is a perspective view showing a twenty-second embodiment of a physical protector according to this invention.

FIG. 81 shows a twenty-second embodiment of this invention, which can be suitably used as a supporter for the chin g. The bag member 10 of this embodiment is made slender like a belt and has ear holes 300 for catching the ears p. According to this embodiment, the chin can be cushioned.

Figure 82:
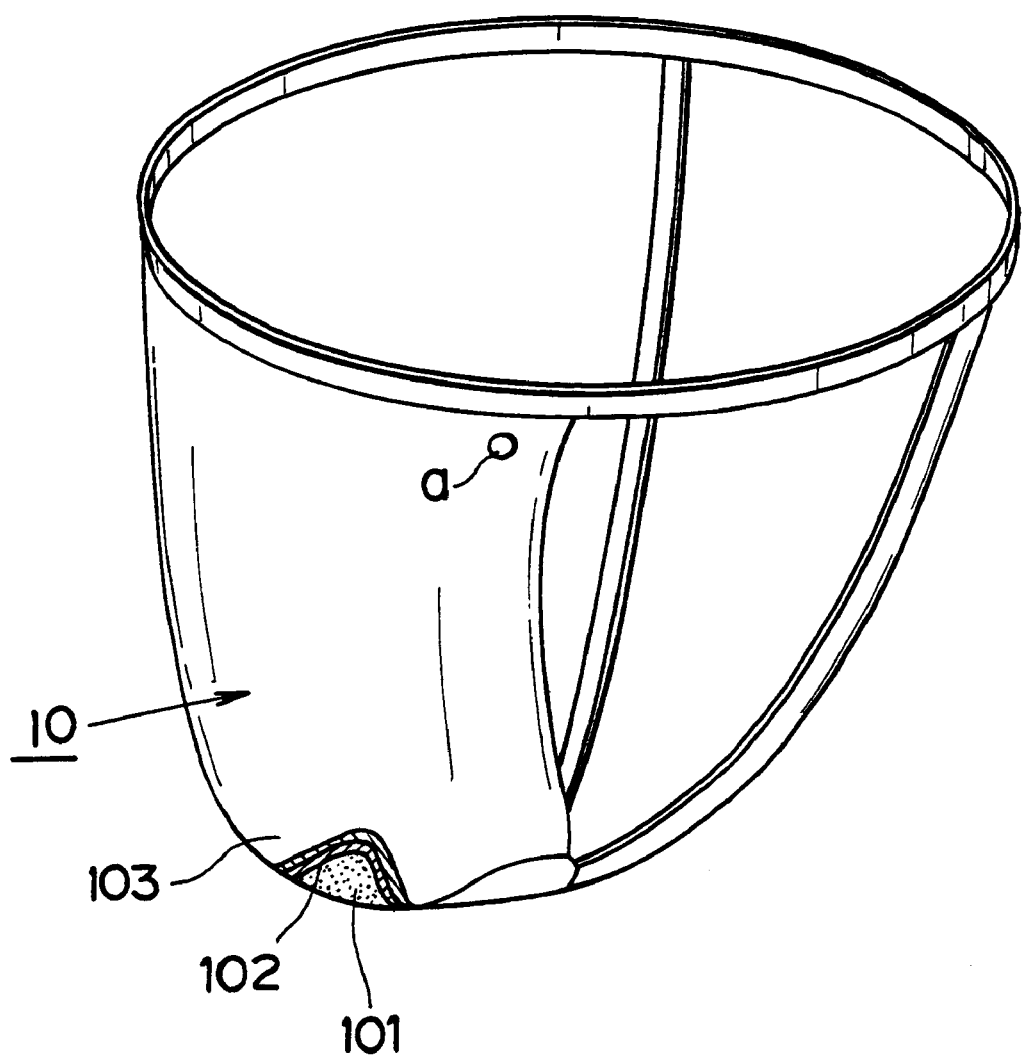
FIG. 82 is a front view showing a twenty-third embodiment of a physical protector according to this invention in use.

FIG. 82 shows a twenty-third embodiment of this invention, which can be suitably used as a supporter for the buttocks. This supporter can be detachably attached to a pair of garters with ease. This embodiment has not only a function of protecting the buttocks, but also functions of a warmer and a shape retainer.

Figure 83:
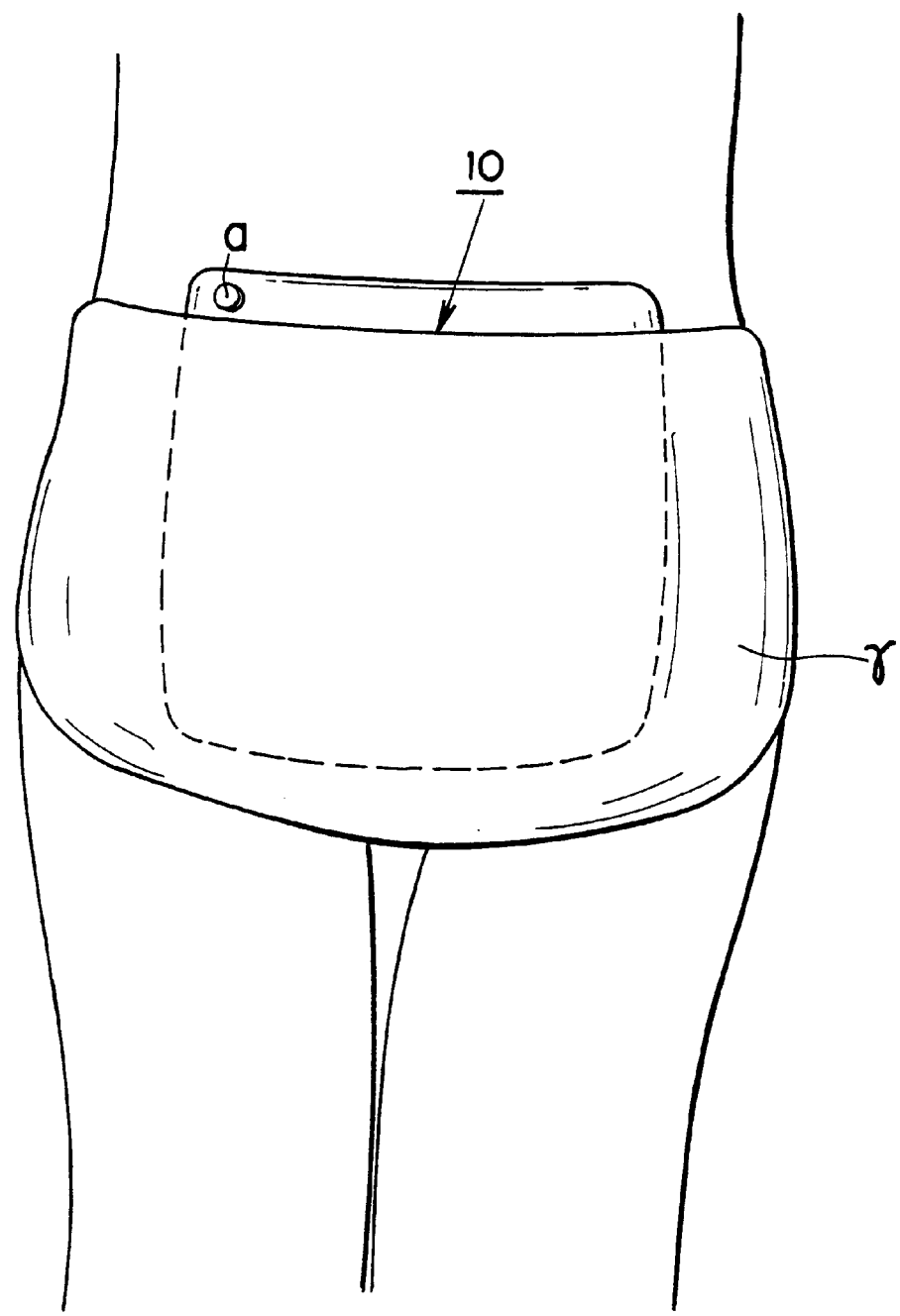
FIG. 83 is a view showing a twenty-fourth embodiment of a physical protector according to this invention in use.

FIG. 83 shows a twenty-fourth embodiment of this invention, in which the bag member 10 which can be suitably used as a supporter for the buttocks is shaped in a mat so as to be inserted in the underwear r. This embodiment can be used for other clothes and various purposes.

Figure 84:
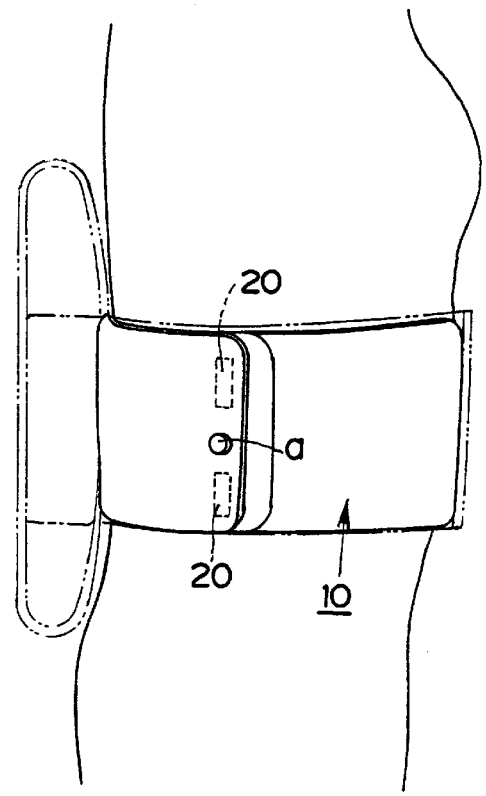
FIG. 84 is a view showing a twenty-fifth embodiment of a physical protector according to this invention in use.

FIG. 84 shows a twenty-fifth embodiment of this invention, comprising a bag member 10 suitably used as an under belt for dressing a Japanese cloth. The under belt 10 is used like a girdle to be wound around the belly and can be adjusted in expansion by controlling the valve a according to the physique.

Figure 85:
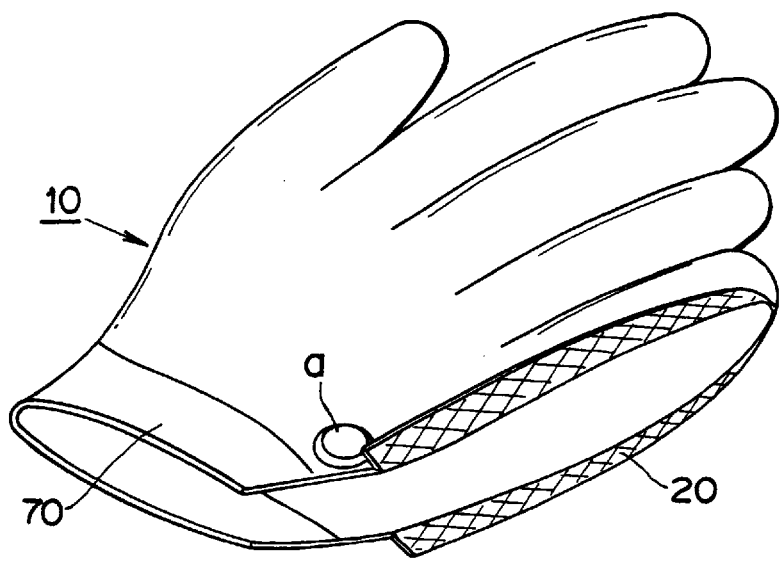
FIG. 85 is a view showing a twenty-sixth embodiment of a physical protector according to this invention in use.

FIG. 85 shows a twenty-sixth embodiment of this invention, which comprises a bag member 10 shaped like a glove. The bag member has wrist tightening means 70 and a surface fastener 20 disposed on the little finger side thereof The wrist tightening means 70 may be made more wide, though not shown, so as to dispose another surface fastener 20 such as Velcro's Magic Tape.

Figure 86:
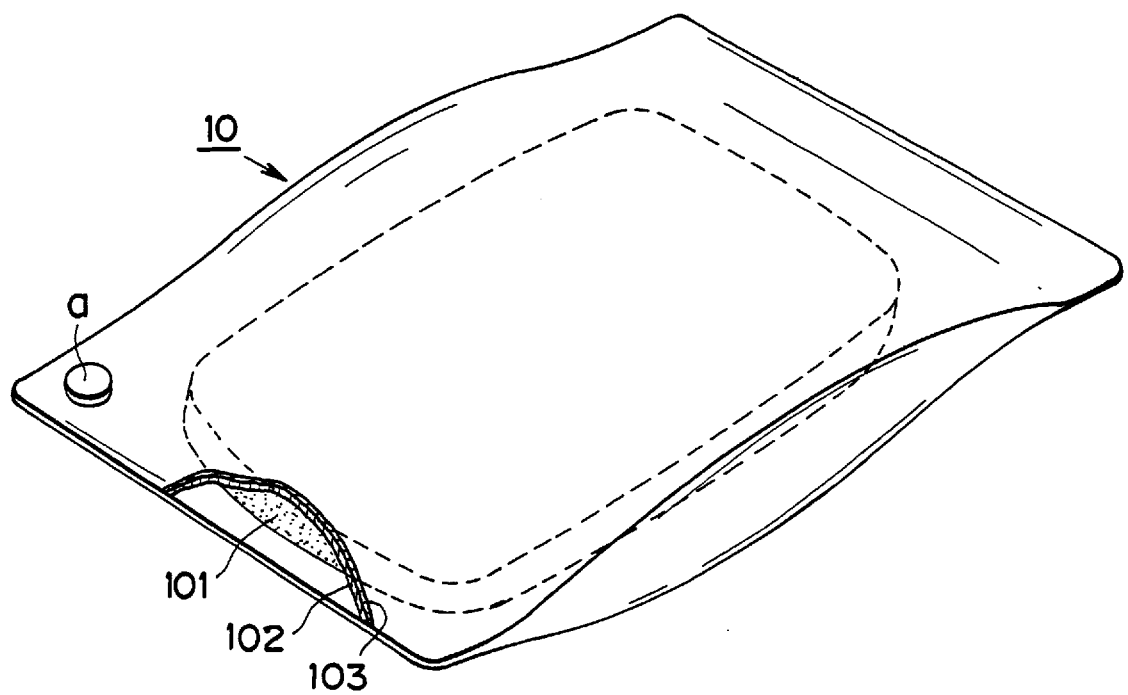
FIG. 86 is a view showing a twenty-seventh embodiment of a physical protector according to this invention in use.

FIG. 86 shows a twenty-seventh embodiment of this invention, in which the bag member 10 is formed into a cushion like a Japanese floor cushion. By depressing the valve a, a desired thickness can be obtained.

This embodiment has the function of a chair cushion capable of being adjusted in thickness, and therefore can be suitably used in a beauty parlor or the like.

Figure 87:
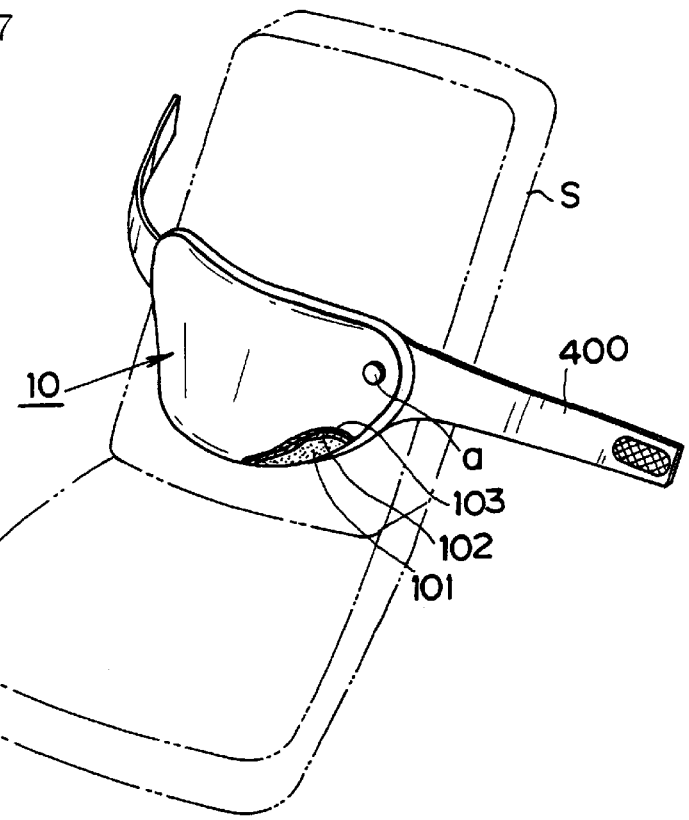
FIG. 87 is a view showing a twenty-eighth embodiment of a physical protector according to this invention in use.

FIG. 87 shows a twenty-eighth embodiment of this invention, which comprises a bag member 10 suitably used as a waist pad to be put on a car seat S. This embodiment has belts 400 for fixing the bag member 10 to the seat S. Since the bag member 10 is formed in an inverted trapezoidal shape, it can support the whole waist and be adjusted in thickness according to physical fatigue.

Figure 88:
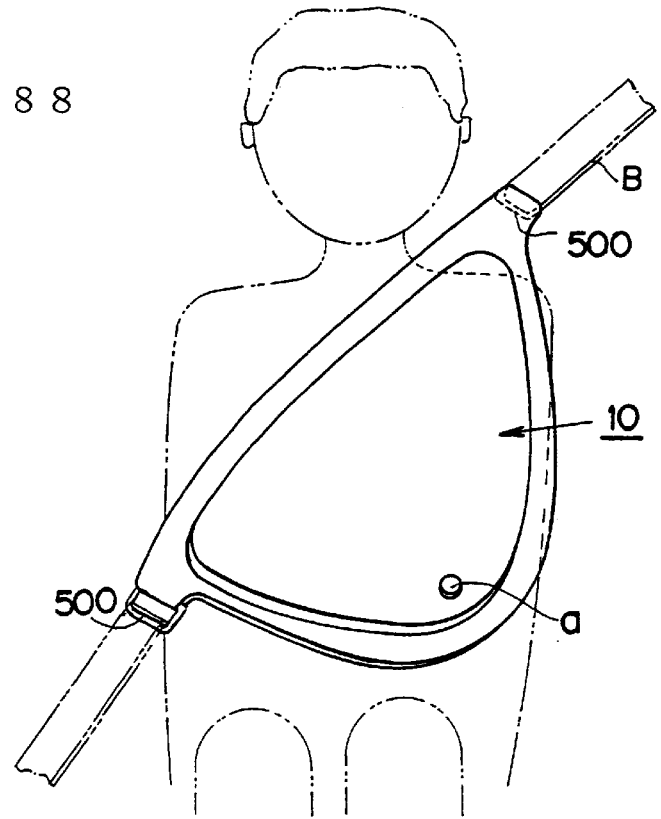
FIG. 88 is a view showing a twenty-ninth embodiment of a physical protector according to this invention in use.

FIG. 88 shows a twenty-ninth embodiment of this invention, which comprises a bag member 10 capable of being connected to a seat belt B. This embodiment has fastening bands 500 for connecting the bag member 10 to the seat belts B. The bag member 10 widely covers the chest and belly, and the function of an air bag for protecting such physical parts can be expected.

The bag member 10 of this embodiment may be attached to the seat belt B or itself used as a seat belt B. In either case, the shock-absorbing function of the seat belt B can be heightened.

Figure 89:
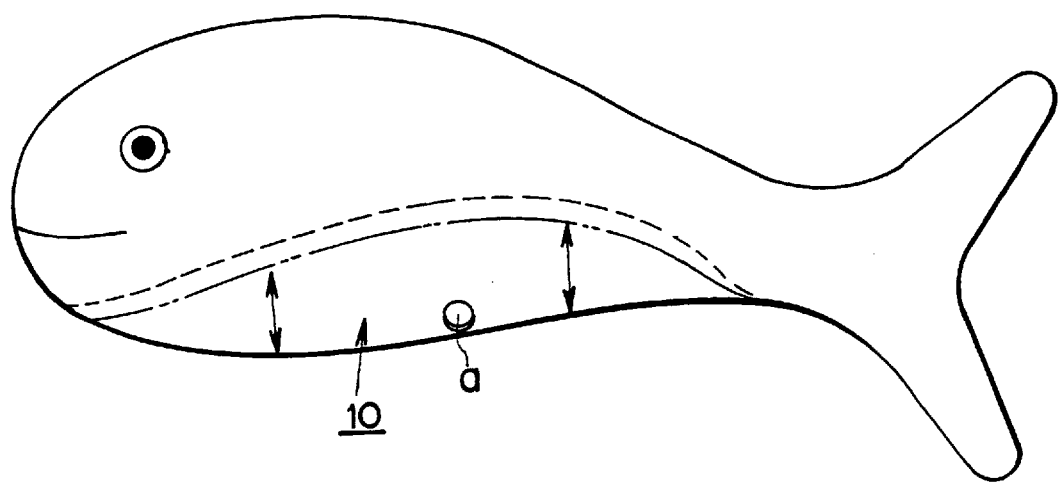
FIG. 89 is a front view showing a thirtieth embodiment of a physical protector according to this invention.

FIG. 89 shows a thirtieth embodiment of this invention, in which the bag member 10 is used as a part of a doll or toy. As one example, the bag member 10 is shaped as a fish. According to this embodiment, since the doll or toy can be changed in size and contracted when not used, it becomes easy to carry and store.

Figure 90:
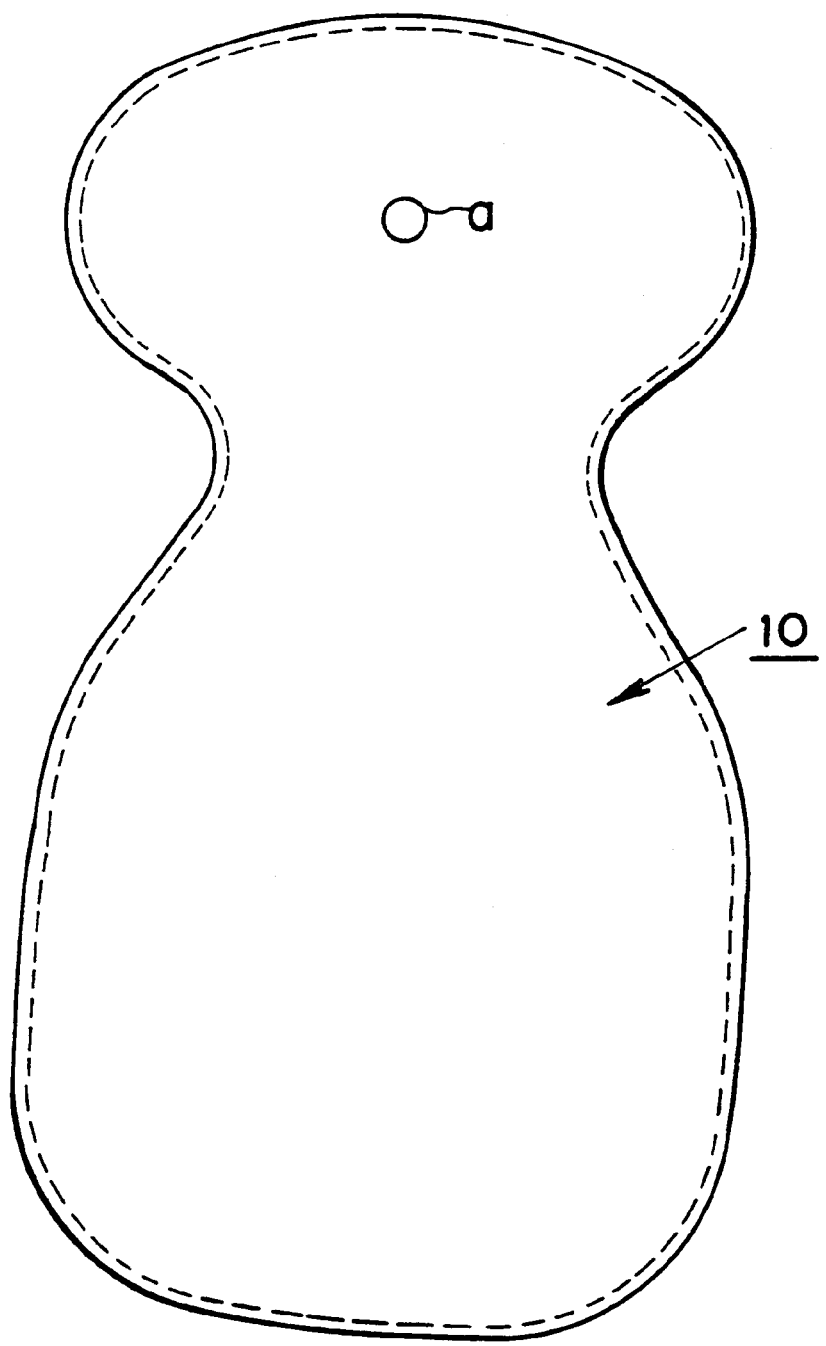
FIG. 90 is a view showing a thirty-first embodiment of a physical protector according to this invention in use.
Figure 91:
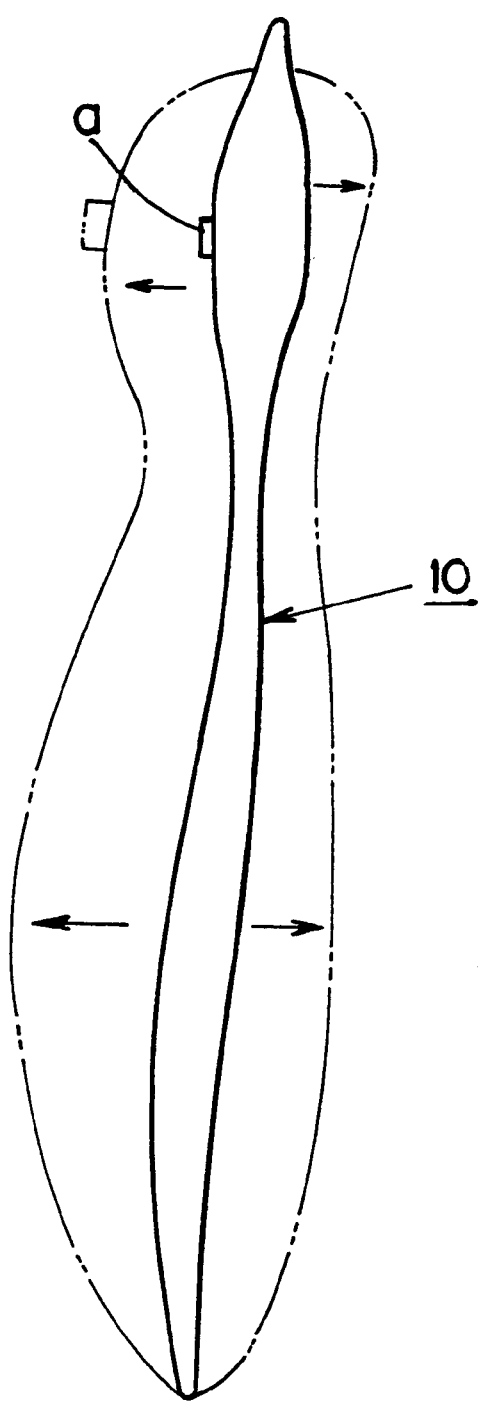
FIG. 91 is an operational side view of FIG. 90.

FIG. 90 and FIG. 91 show a thirty-first embodiment of the present invention, in which the bag member 10 is formed into a stuffed toy. According to this embodiment, stuffing to be stuffed into the stuffed toy can be omitted. The bag member 10 can be inflated into a desired shape.

Figure 92:
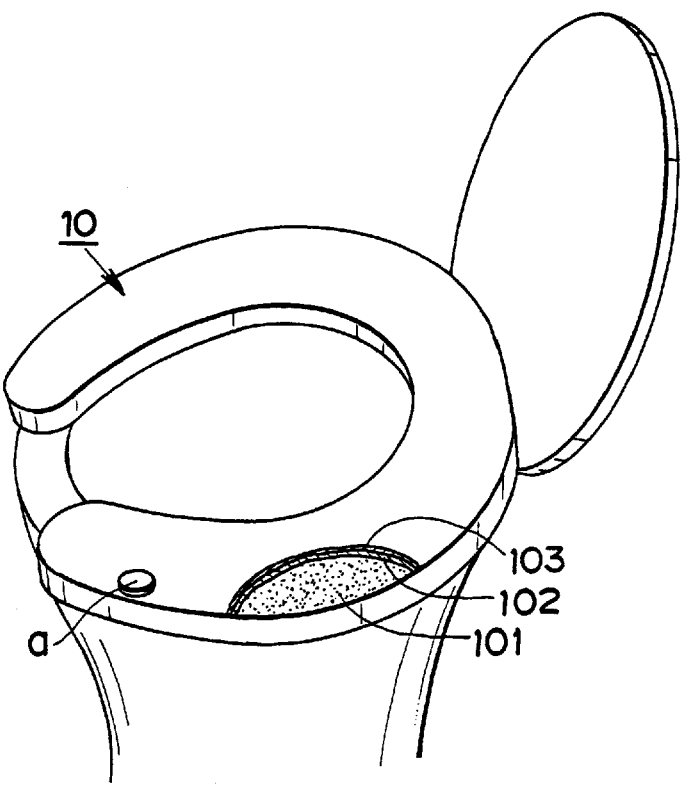
FIG. 92 is a view showing a thirty-second embodiment of a physical protector according to this invention in use.

FIG. 92 shows a thirty-second embodiment of this invention, which comprises the bag member 10 shaped in a horseshoe so as to be used as a toilet seat cover.

Figure 93:
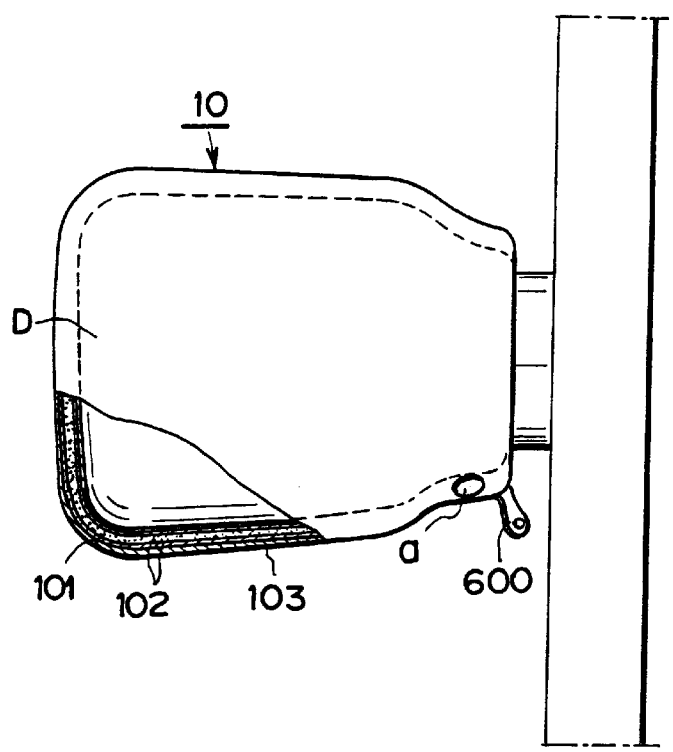
FIG. 93 is a view showing a thirty-third embodiment of a physical protector according to this invention in use.

FIG. 93 shows a thirty-third embodiment of this invention, which comprises the bag member capable of being used as a cover for a door knob D. This embodiment has a fastener 600 for removably attaching the bag member 10 to the door knob D.

Figure 94:
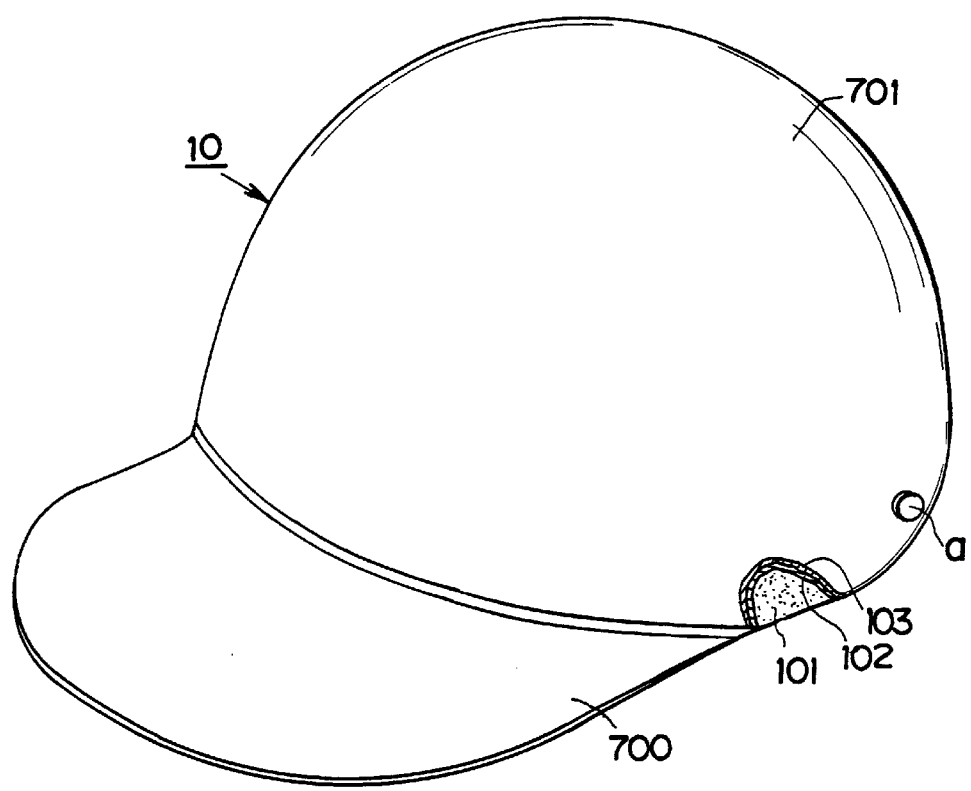
FIG. 94 is a view showing a thirty-fourth embodiment of a physical protector according to this invention in use.

FIG. 94 shows a thirty-fourth embodiment of this invention, in which the bag member 10 is formed in a semispherical shape to form a hat 701 other than a brim. The bag member may be shaped like a cap, though not shown. In this case, it may be provided with a fastening string so as to be used as a hard helmet, or otherwise attached into the inside of a helmet to improve the shock-absorbing function.

Figure 95:
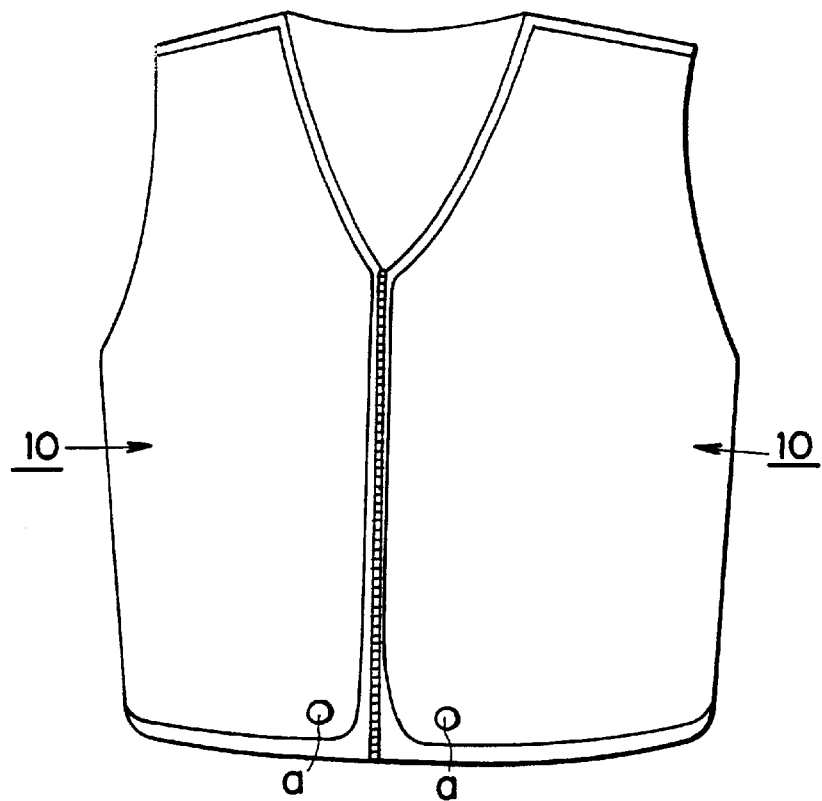
FIG. 95 is a view showing a thirty-fifth embodiment of a physical protector according to this invention in use.

FIG. 95 shows a thirty-fifth embodiment of this invention, in which the bag members 10 are attached to the front right and left panels of a vest, respectively. The bag members 10 attached to the right and left panels can be arbitrarily inflated. By further attaching another bag member 10 to the back of the vest, the front and back of the human body can be cushioned. The valves a may be disposed on the respective front panels so as to be easily handled.

Figure 96:
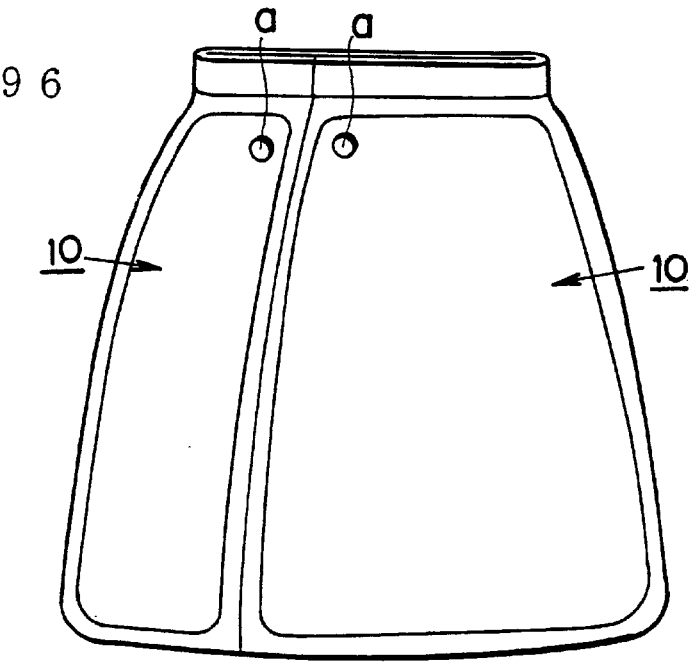
FIG. 96 is a view showing a thirty-sixth embodiment of a physical protector according to this invention in use.

FIG. 96 shows a thirty-sixth embodiment of this invention, in which the bag members 10 are attached to the front right and left sides of a skirt, respectively. According to this embodiment, the legs and waist can be cushioned. Such a skirt may be formed like long pants and integrally connected to the vest of the aforesaid thirty-fifth embodiment, though not shown, so that the protector can be used as a wet suit.

Figure 98:
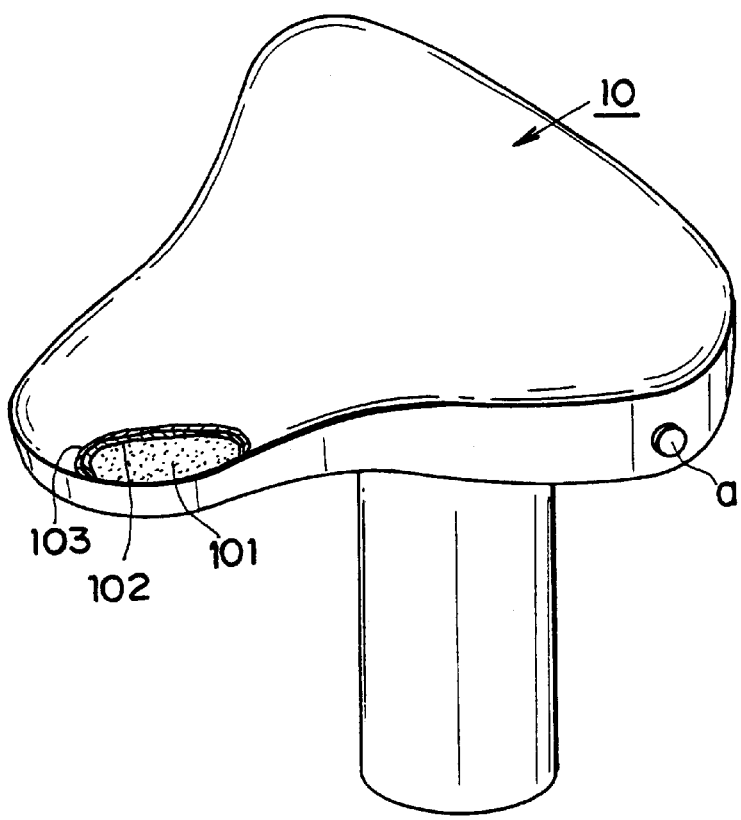
FIG. 98 is a view showing a thirty-eighth embodiment of a physical protector according to this invention in use.

FIG. 98 shows a thirty-seventh embodiment of this invention, in which a bicycle saddle is formed of the bag member 10. As a modified form, a cover for a bicycle saddle may be formed of the bag member 10.

Figure 97:
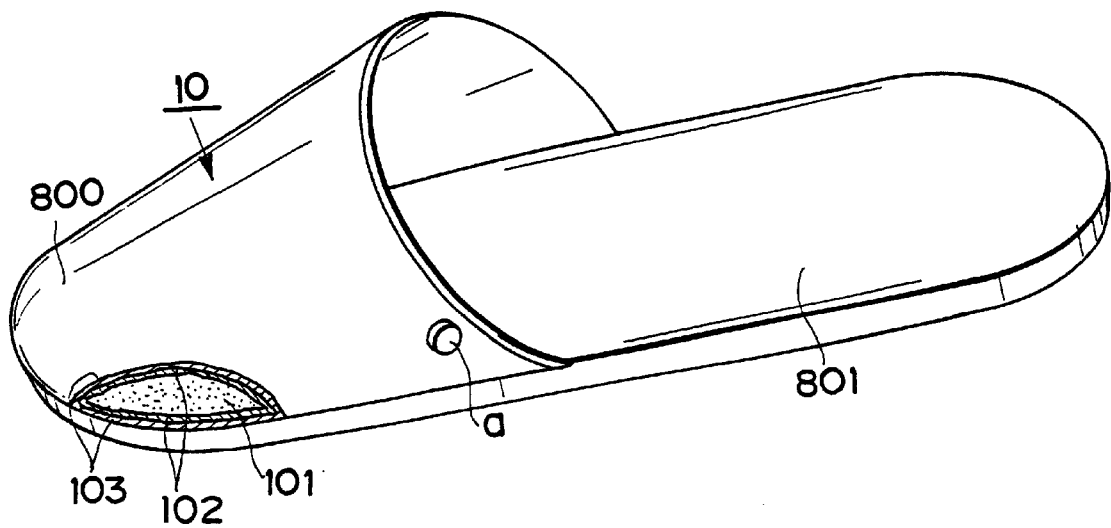
FIG. 97 is a view showing a thirty-seventh embodiment of a physical protector according to this invention in use.

FIG. 97 shows a thirty-eighth embodiment of this invention, in which the bag member 10 is used as a cover 800 for the toe of footwear or slippers. Of course, the bag member 10 may be formed like a heel cover.

Figure 99:
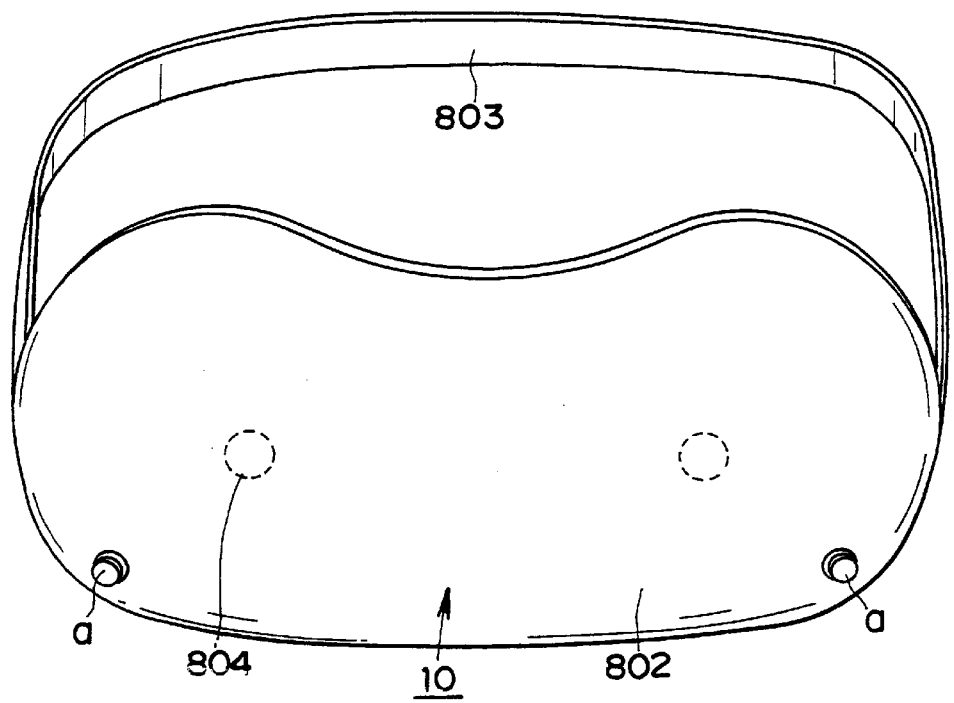
FIG. 99 is a view showing a thirty-ninth embodiment of a physical protector according to this invention in use.

FIG. 99 shows a thirty-ninth embodiment of this invention, in which the bag member 10 is used as a mask member 802 of an eye mask and provided with hooking strings 803. The mask member 802 may be provided in the portions confronting the eyeballs with small holes which vary in diameter and axial length according to the degree in which the bag member is inflated, so as to be used for curing the eyeballs.

Figure 100:
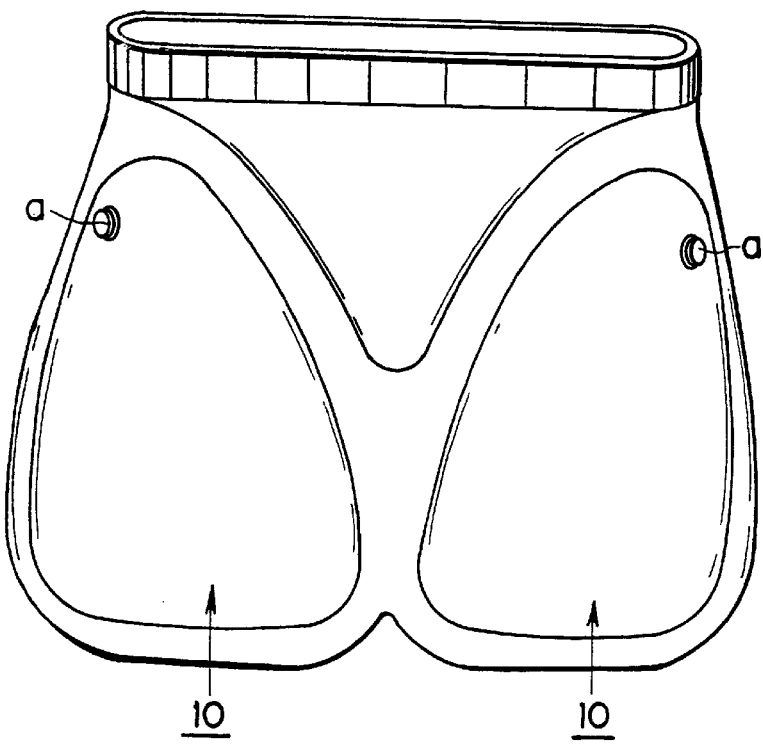
FIG. 100 is a view showing a fortieth embodiment of a physical protector according to this invention in use.

FIG. 100 shows a fortieth embodiment of this invention, in which the bag member 10 constitutes a part of trunks. This embodiment can be used as protective pants for combative sports or ball games and adjusted as required.

Figure 101:
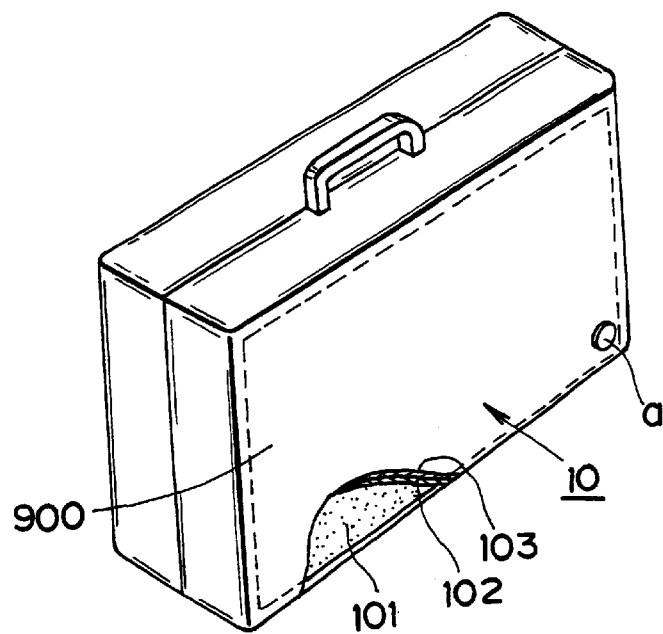
FIG. 101 is a view showing a forty-first embodiment of a physical protector according to this invention in use.

FIG. 101 shows a forty-first embodiment of this invention, in which the bag member 10 constitutes a bag. It is preferable to form reinforcing members 900 in a frame shape to which the bag should be maintained. This bag may be used for carrying fragile articles such as glasswork.

Figure 102:
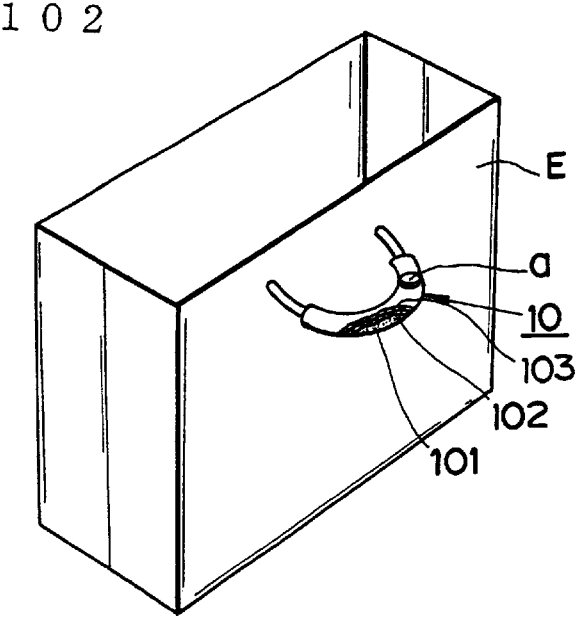
FIG. 102 is a view showing a forty-second embodiment of a physical protector according to this invention in use.

FIG. 102 shows a forty-second embodiment of this invention, in which the bag member 10 constitutes carrying strings of a paper bag E. Since the carrying strings are expandable, this embodiment provides advantageous carrying of goods.

Figure 103:
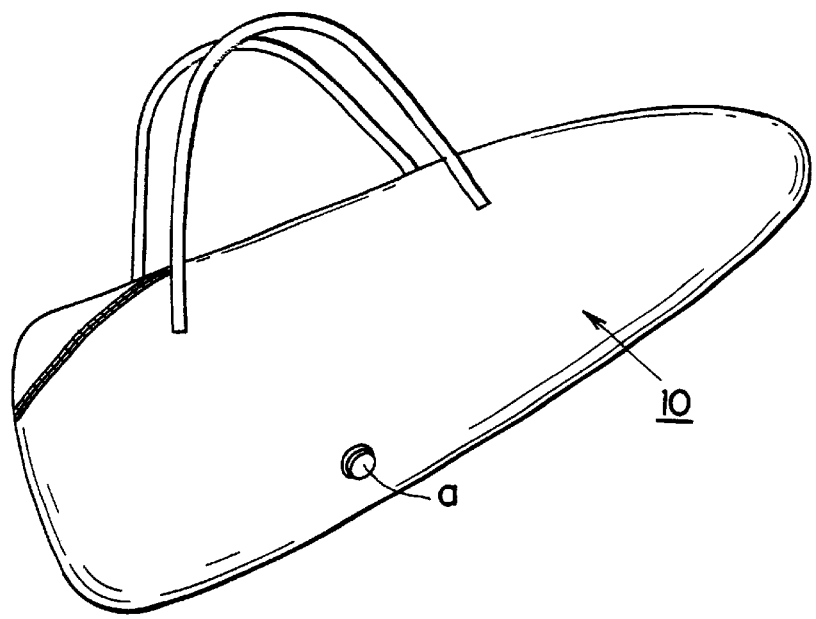
FIG. 103 is a view showing a forty-third embodiment of a physical protector according to this invention in use.

FIG. 103 shows a forty-third embodiment of this invention, in which the bag member 10 constitutes a bag for carrying a snowboard, a surfboard or the like. This embodiment can fulfill a sufficient cushioning function in carrying without using a specific package.

Figure 104:
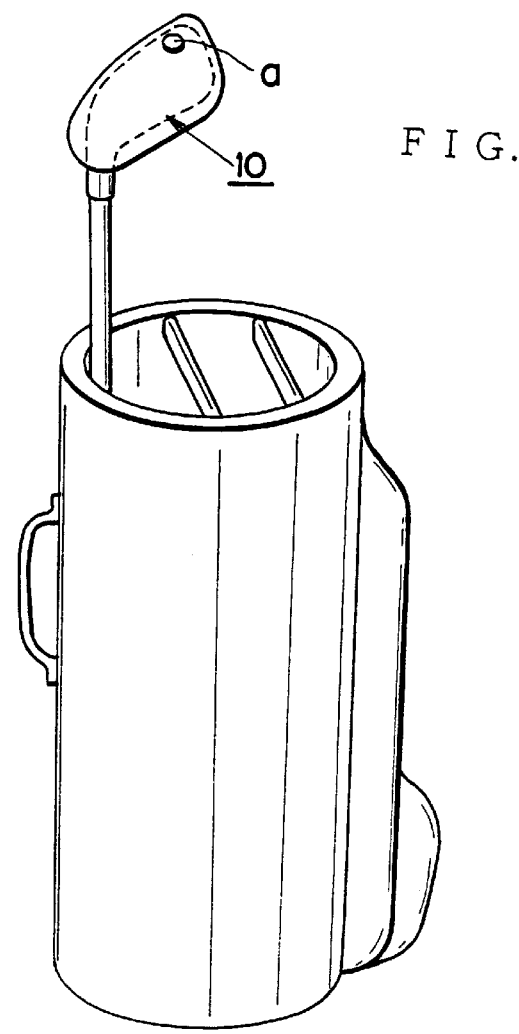
FIG. 104 is a view showing a forty-fourth embodiment of a physical protector according to this invention in use.

FIG. 104 shows a forty-fourth embodiment of this invention, in which the bag member 10 constitutes a head cover for a golf club.

Figure 105:
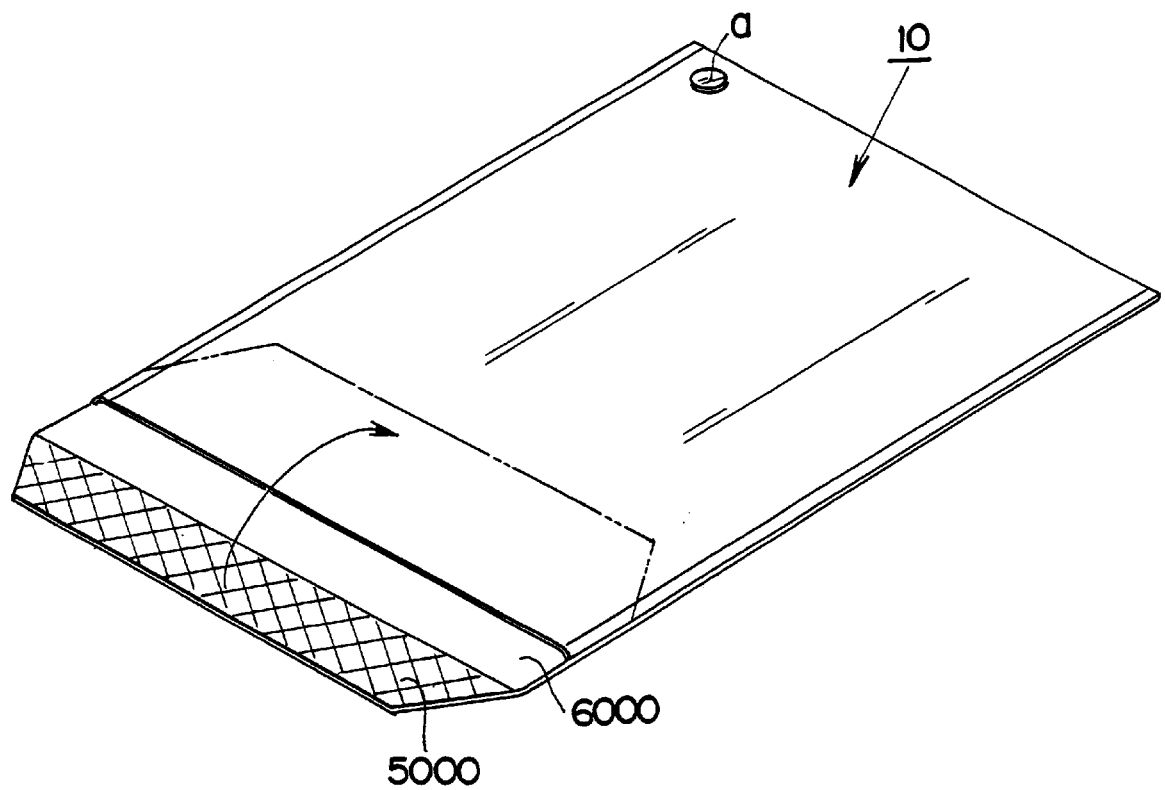
FIG. 105 is a view showing a forty-fifth embodiment of a physical protector according to this invention in use.

FIG. 105 shows a forty-fifth embodiment of this invention, in which the bag member 10 can be suitably used as an envelope for documents or the like. The bag member 10 is provided with sealing means 6000 applied with adhesive 5000.

Figure 106:
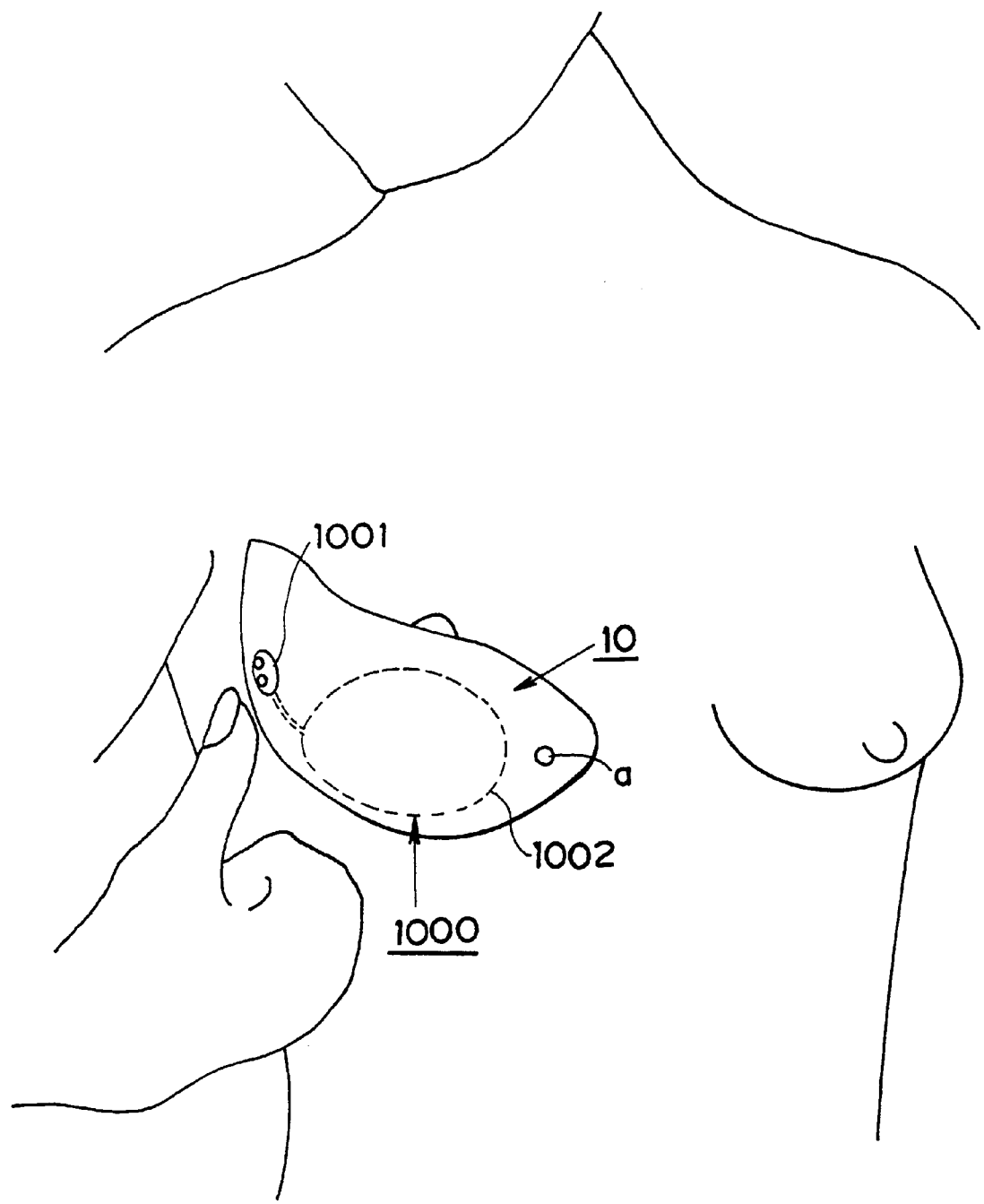
FIG. 106 is a view showing a forty-sixth embodiment of a physical protector according to this invention in use.

FIG. 106 shows a forty-sixth embodiment of this invention, in which the bag member 10 is provided with a low-frequency oscillator 1000. This oscillator 1000 comprises a controlling unit 1001 including a battery, a switch and a controller, and an oscillating at electrode 1002 for oscillating a low frequency.

According to this embodiment, the oscillated low frequency imparts stimulation to the body or the like, consequently to improve the circulation of the blood and hormone secretion. The valve a in this embodiment is disposed on the inside end portion of the bag member.

Figure 107:
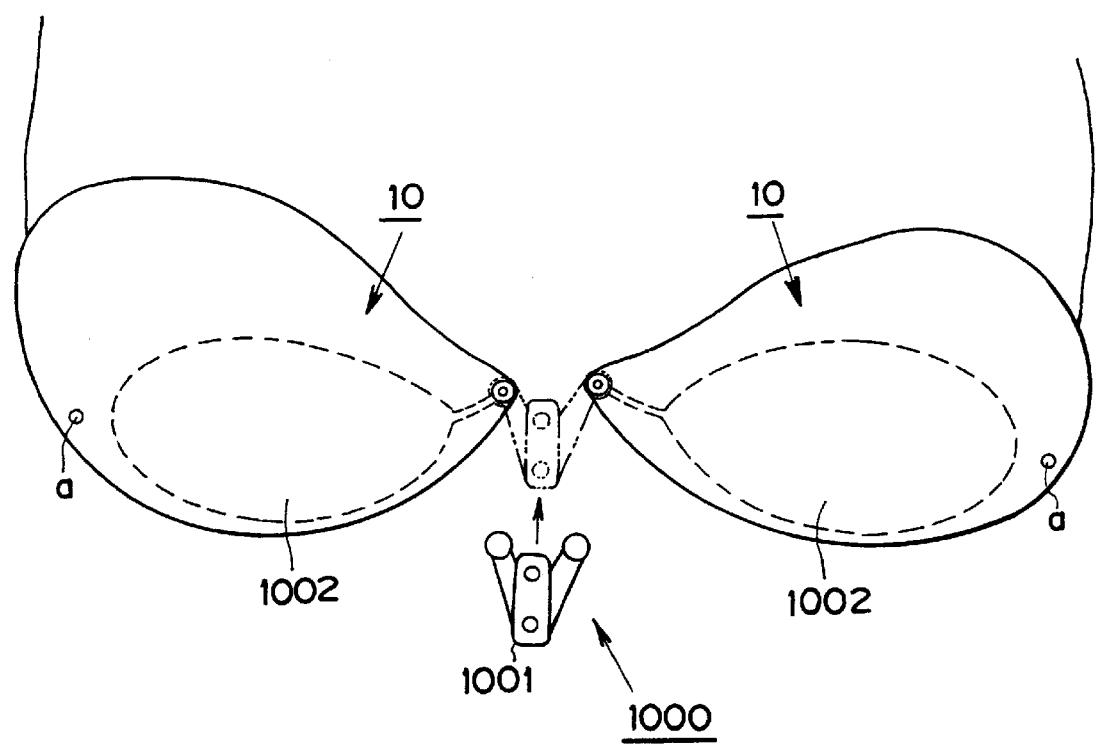
FIG. 107 is a view showing a forty-seventh embodiment of a physical protector according to this invention in use.

FIG. 107 shows a forty-seventh embodiment of this invention, in which the controlling unit 1001 and the oscillating electrode 1002 of the oscillator 1000 are detachable, and the controlling unit 1001 functions as the clasp of a brassiere.

Figure 108:
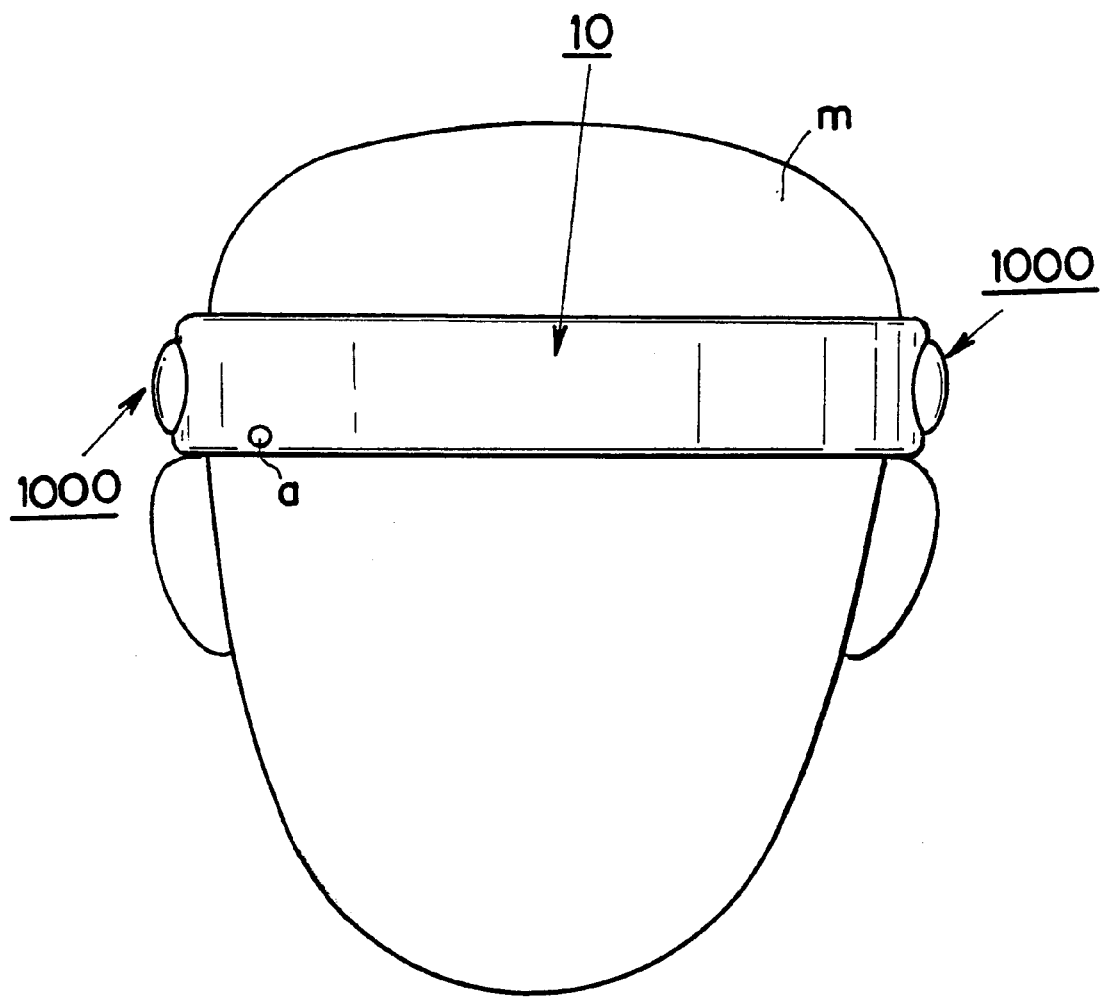
FIG. 108 is a view showing a forty-eighth embodiment of a physical protector according to this invention in use.

FIG. 108 shows a forty-eighth embodiment of this invention, in which the oscillators 1000 are incorporated in a head band to be wound around the head m. If there is a possibility that the low frequency stimulation brought about by the oscillator gives a user an unpleasant feeling, a magnet or the like may be used instead of the low frequency oscillator.

Figure 109:
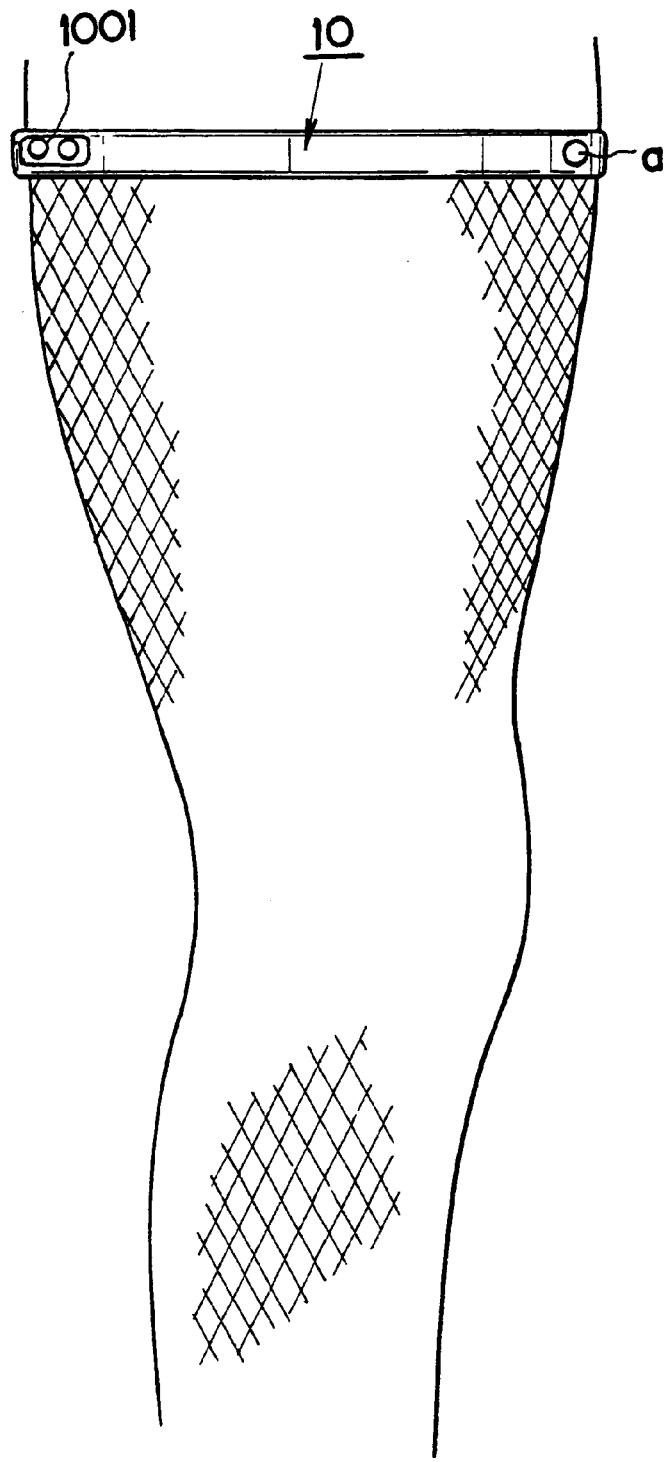
FIG. 109 is a view showing a forty-ninth embodiment of a physical protector according to this invention in use.

FIG. 109 shows a forty-ninth embodiment of this invention, in which the oscillator 1000 is incorporated in a garter or suspender to be wound around the leg.

Figure 110:
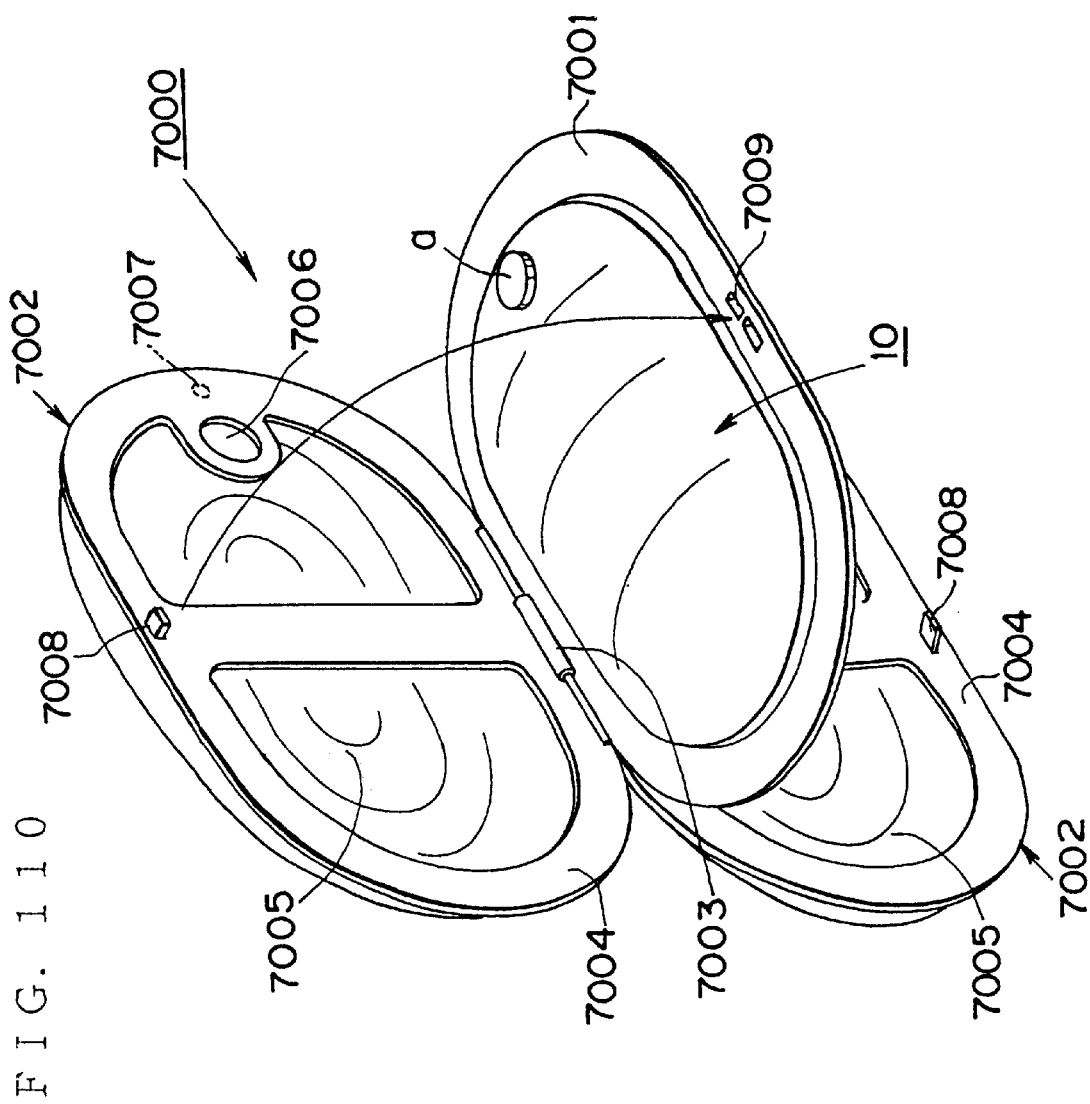
FIG. 110 is a perspective view showing a device for discharging fluid for use in the protector of this invention.

FIG. 110 shows a fluid discharging device 7000 which is used after using the physical protector according to the embodiments mentioned above of the present invention.

The fluid discharging device 7000 is formed by a pair of case halves 7002 connected to each other through a hinge 7003 like a cosmetic compact. Between the case halves, a flat partition member 7001 is interposed. The case half 7002 is formed by attaching a lid member 7005 of soft synthetic resin to the outside of a frame 7004 of hard synthetic resin. By pressing the lid member 7005 in the state that the aforesaid physical protector is placed between the partition member 7001 and the lid member 7005, the fluid G can be discharged acceleratedly.

The frame 7004 of the case half 7002 has a valve receiving portion 7006 into which the valve a is inserted. In the lid member 7005 of the case half 7002, there is bored a fluid outlet hole 7007 for allowing the fluid G discharged from the valve a to escape outward. Each frame 7004 of the case half 7002 has an engaging protrusion 7008, and correspondingly, the partition member 7001 has holes 7009 for receiving the engaging protrusions 7008 of the frames, so that the case halves 7002 and the partition member 7001 can be kept in their closed state.

According to this fluid discharging device 7000, the fluid G can be discharged from the bag member 10 easily and promptly.

The physical protector of the invention can be applied to various fields and purposes other than those mentioned above by use of its cushioning and heat-retaining functions. To further heighten these functions, there may be employed a material capable of emitting far infrared radiation and/or a mechanism using solar heat.

The various types of embodiments of the invention were described above on the assumption that expandable material is accommodated in the bag member 10 in its compressed state, but this should not be understood as limitative. The bag member 10 in which such expandable material is not accommodated can be inflated by operating the valve a to introduce air thereinto through the pump portion or mouth portion. The discharge of the air can be carried out by opening the valve a and pressing the bag member. Although the reinforcing member 30 is applied to some of the embodiments described above, it may be added to the bag member of the other embodiments if the need arises.

Also, the bag member 10 may be provided on its inner or outer side with deformation-retaining means made of resin material which is deformed into a fixed shape with body temperature. The resin material is what is known as polymer jell, hydro jell, smart jell, and terminal jell. The terminal jell assumes a fluid state at room temperature, but exhibits viscosity to assume a fixed shape when warmed with body temperature. Thus, the deformation-retaining means can assist to protect and/or cure each part of the human body.

As described above, since the physical protector according to the present invention comprises the inflatable bag member with a plurality of seal members which are different in deformability, a two-way valve capable of opening and closing due to the difference in deformability, which is remarkably made simple in structure and compact, can be realized. Also, since the protector makes use of the deformability of the seal members, an effect in that the protector is not embrittled nor malfunctions during repeated prolonged use can be brought about.

Furthermore, since the expandable material accommodated in the bag member can spontaneously expand to maintain its shape when opening the valve, it can be controlled in degree of expansion by depressing the valve, and therefore, suitably used as a physical protective means. Besides, the shape of the bag member thus expanded can be maintained and the degree of expansion of the bag member can be regulated by operating the valve.

As described above, since the physical protector according to this invention has the seal members constituting a valve which is disposed on a flat bag member and elastically deformed with a depressing force to form an air passage between the seal members and regains its original shape when releasing the depressing force to close the air passage, the bag member can conveniently be attached to an object to be protected and inflated with ease. Therefore, the physical protector can be applied for protecting and/or securing each part of the human body such as the trunk and limbs in various medical situations, or used as a supporter, protector or corset for various sports, or packaging means capable of easily and reliably protecting goods or articles of various shapes other than the human body.

What is claimed is:

1. A physical protector comprising gas-barrier seal members different in deformability: a valve which is opened by exerting a pushing force to said seal members to elastically deform said seal members and closed by releasing the pushing force to resume an original shape of said seal members; and a flat bag member capable of being attached to a physical part, said bag member being formed by sheet-like gas barrier membranes, and said valve being mounted onto said bag member so as to open or close said bag member, wherein said seal members comprise a soft seal member and a rigid seal member, wherein said seal member is formed of a film, and said rigid seal member is formed of a sheet having a desired thickness, and wherein said seal members are provided at different positions with vent holes and kept in intimate face contact with each other in a normal state, and wherein said rigid seal member is formed in a spherical shape having a central protrusion capable of being elastically deformed, and said soft seal member is placed on said rigid seal member in layers so as to be in intimate contact with the spherical surface of said rigid seal member.

2. A physical protector according to claim 1, wherein said rigid seal member is provided with a support column extending downward from center of, a lower surface of said rigid seal member.

3. A physical protector comprising gas-barrier seal members different in deformability: a valve which is opened by exerting a pushing force to said seal members to elastically deform said seal members and closed by releasing the pushing force to resume an original shape of said seal members; and a flat bag member capable of being attached to a physical part, said bag member being formed by sheet-like gas barrier membranes, and said valve being mounted onto said bag member so as to open or close said bag member, wherein said seal members comprise a soft seal member and a rigid seal member, wherein said soft seal member is formed of a film, and said rigid seal member is formed of a sheet having a desired thickness, and wherein said seal members are provided at different positions with vent holes and kept in intimate face contact with each other in a normal state, and wherein said soft seal member is provided in its central portion with a vent hole, and said rigid seal member is provided in its peripheral portion with vent holes.

4. A physical protector comprising gas-barrier seal members different in deformability; a valve which is opened by exerting a pushing force to said seal members to elastically deform said seal members and closed by releasing the pushing force to resume an original shape of said seal members; and a flat bag member capable of being attached to a physical part, said bag member being formed by sheet-like gas barrier membranes, and said valve being mounted onto said bag member so as to open or close said bag member, wherein said seal members comprise a soft seal member and a rigid seal member, and wherein said soft seal member constitutes a valve body having a substantially H-shaped vertical cross section, and said rigid seal member constitutes a sleeve-shaped valve seat having an accommodating hole for said valve body, said valve body being elastically deformed with a depressing force to form an air passage between said valve body and said accommodating hole.

5. A physical protector comprising gas-barrier seal members different in deformability; a valve which is opened by exerting a pushing force to said seal members to elastically deform said seal members and closed by releasing the pushing force to resume an original shape of said seal members, and a flat bag member capable of being attached to a physical part said bag member being formed by sheet-like gas barrier membranes, and said valve being mounted onto said bag member so as to open or close said bag member, wherein said seal members comprise a soft seal member and a rigid seal member, and wherein said soft seal member constitutes a valve body having a substantially H-shaped vertical cross section, and said rigid seal member constitutes a sleeve-shaped valve seat having an accommodating hole for said valve body, said valve body being provided with a rotary pressing member which is elastically deformable with a depressing force to form an air passage between said valve body and said accommodating hole.

6. A physical protector comprising gas-barrier seal members different in deformability a valve which is opened by exerting a pushing force to said seal members to elastically deform said seal members and closed by releasing the pushing force to resume an original shape of said seal members, and a flat bag member capable of being attached to a physical part, said bag member being formed by sheet-like gas barrier membranes, and said valve being mounted onto said bag member so as to open or close said bag member, wherein said seal members comprise a soft seal member and a rigid seal member, and wherein said rigid seal member constitutes a valve body having a substantially H-shaped vertical cross section, and said soft member constitutes a sleeve-shaped valve seat having an accommodating hole for said valve body, said valve body being elastically deformed with a depressing force to form an air passage between said valve body and said accommodating hole.

7. A physical protector comprising gas-barrier seal members different in deformability; a valve which is opened by exerting a pushing force to said seal members to elastically deform said seal members and closed by releasing the pushing force to resume an original shape of said seal members; and a flat bag member capable of being attached to a physical part, said bag member being formed by sheet-like gas barrier membranes, and said valve being mounted onto said bag member so as to open or close said bag member, wherein said seal members comprise a soft seal member and a rigid seal member, and wherein said soft seal member constitutes a valve body including a base plate and having a substantially H-shaped vertical cross section, and said rigid seal member constitutes a sleeve-shaped valve seat having a tapered accommodating hole for said valve body, so that an air passage is formed between said base plate and said accommodating hole by sliding said valve body with a depressing force.

8. A physical protector comprising gas-barrier seal members different in deformability; a valve which is opened by exerting a pushing force to said seal members to elastically deform said seal members and closed by releasing the pushing force to resume an original shape of said seal members; and a flat bag member capable of being attached to a physical part, said bag member being formed by sheet-like gas barrier membranes, and said valve being mounted onto said bag member so as to open or close said bag member, and further comprising a waterproof cover disposed on one part of said seal members.

9. A physical protector comprising gas-barrier seal members different in deformability; a valve which is opened by exerting a pushing force to said seal members to elastically deform said seal members and closed by releasing the pushing force to resume an original shape of said seal members; and a flat bag member capable of being attached to a physical part, said bag member being formed by sheet-like gas-barrier membranes and stuffed with an expandable member in its compressed state, said valve being mounted onto said bag member so as to open or close said bag member, wherein said seal members are a soft seal member and a rigid seal member, wherein said soft seal member is formed of a film, and said rigid seal member is formed of a sheet having a desired thickness, and said seal members are provided in different positions with vent holes and kept in intimate face contact with each other in a normal state, and wherein said rigid seal member is formed in a spherical shape having a central protrusion capable of being elastically deformed, and said soft seal member is placed on said rigid seal member in layers so as to be in intimate contact with the spherical surface of said rigid seal member.

10. A physical protector according to claim 9, wherein said rigid seal member is provided with a support column extending downward from a center of a lower surface of said rigid seal member.

11. A physical protector comprising gas-barrier seal members different in deformability; a valve which is opened by exerting a pushing force to said seal members to elastically deform said seal members and closed by releasing the pushing force to resume an original shape of said seal members; and a flat bag member capable of being attached to a physical part, said bag member being formed by sheet-like gas-barrier membranes and stuffed with an expandable member in its compressed state, said valve being mounted onto said bag member so as to open or close said bag member, wherein said seal members are a soft seal member and a rigid seal member, wherein said soft seal member is formed of a film, and said rigid seal member is formed of a sheet having a desired thickness, and said seal members are provided in different positions with vent holes and kept in intimate face contact with each other in a normal state, and wherein said soft seal member is provided in its central portion with a vent hole, and said rigid seal member is provided in its peripheral portion with vent holes.

12. A physical protector comprising gas-barrier seal members different in deformability; a valve which is opened by exerting a pushing force to said seal members to elastically deform said seal members and closed by releasing the pushing force to resume an original shape of said seal members; and a flat bag member capable of being attached to a physical part, said bag member being formed by sheet-like gas-barrier membranes and stuffed with an expandable member in its compressed state, said valve being mounted onto said bag member so as to open or close said bag member, wherein said seal members are a soft seal member and a rigid seal member, and wherein said soft seal member constitutes a valve body having a substantially H-shaped vertical cross section, and said rigid seal member constitutes a sleeve-shaped valve seat having an accommodating hole for said valve body, said valve body being elastically deformed with a depressing force to form an air passage between said valve body and said accommodating hole.

13. A physical protector comprising gas-barrier seal members different in deformability; a valve which is opened by exerting a pushing force to said seal members to elastically deform said seal members and closed by releasing the pushing force to resume an original shape of said seal members; and a flat bag member capable of being attached to a physical part, said bag member being formed by sheet-like gas-barrier membranes and stuffed with an expandable member in its compressed state, said valve being mounted onto said bag member so as to open or close said bag member, wherein said seal members are a soft seal member and a rigid seal member, and wherein said rigid seal member constitutes a valve body having a substantially H-shaped vertical cross section, and said soft seal member constitutes a sleeve-shaped valve seat having an accommodating hole for said valve body, said valve body being elastically deformed with a depressing force to form an air passage between said valve body and said accommodating hole.

14. A physical protector comprising gas-barrier seal members different in deformability; a valve which is opened by exerting a pushing force to said seal members to elastically deform said seal members and closed by releasing the pushing force to resume an original shape of said seal members; and a flat bag member capable of being attached to a physical part, said bag member being formed by sheet-like gas-barrier membranes and stuffed with an expandable member in its compressed state, said valve being mounted onto said bag member so as to open or close said bag member, wherein said seal members are a soft seal member and a rigid seal member, and wherein said soft seal member constitutes a valve body including a base plate and having a substantially H-shaped vertical cross section, and said rigid seal member constitutes a sleeve-shaped valve seat having a tapered accommodating hole for said valve body, so that an air passage is formed between said base plate and said accommodating hole by sliding said valve body with a depressing force.

15. A physical protector comprising gas-barrier seal members different in deformability; a valve which is opened by exerting a pushing force to said seal members to elastically deform said seal members and closed by releasing the pushing force to resume an original shape of said seal members; and a flat bag member capable of being attached to a physical part, said bag member being formed by sheet-like gas-barrier membranes and stuffed with an expandable member in its compressed state, said valve being mounted onto said bag member so as to open or close said bag member, wherein said seal members are a soft seal member and a rigid seal member, and further comprising a waterproof cover disposed on one part of said seal members.

16. A physical protector comprising gas-barrier seal members different in deformability; a valve which is opened by exerting a pushing force to said seal members to elastically deform said seal members and closed by releasing the pushing force to resume the an original shape of said seal members; and a flat bag member capable of being attached to a physical part, said bag member being formed by sheet-like gas-barrier membranes, stuffed with expandable member in its compressed state, and provided with a reinforcing member for maintaining the expanded state of the bag member, said valve being mounted onto said bag member so as to open or close said bag member.

17. A physical protector according to claim 16, wherein said seal members comprise a soft seal member and a rigid seal member.

18. A physical protector according to claim 17, wherein said soft seal member is formed of a film, and said rigid seal member is formed of a sheet having a desired thickness, and said seal members are provided at different positions with vent holes and kept in intimate face contact with each other in a normal state.

19. A physical protector according to claim 18, wherein said rigid seal member is formed in a spherical shape having a central protrusion capable of being elastically deformed, and said soft seal member is placed on said rigid seal member in layers so as to be in intimate contact with the spherical surface of said rigid seal member.

20. A physical protector according to claim 18, wherein said soft seal member is provided in its central portion with a vent hole, and said rigid seal member is provided in its peripheral portion with vent holes.

21. A physical protector according to claim 18, wherein said soft seal member has elongated vent holes each extending from a center toward a side peripheral portion thereof, and said rigid seal member has a vent hole at a position deviating from said vent holes in said soft, seal member.

22. A physical protector according to claim 19, wherein said rigid seal member is provided with a support column extending downward from a center of a lower surface of said rigid seal member.

23. A physical protector according to claim 17, wherein said soft seal member constitutes a valve body having a substantially H-shaped vertical cross section, and said rigid seal member constitutes a sleeve-shaped valve seat having an accommodating hole for said valve body, said valve body being elastically deformed with a depressing force to form an air passage between said valve body and said accommodating hole.

24. A physical protector according to claim 17, wherein said rigid seal member constitutes a valve body having a substantially H-shaped vertical cross section, and said soft seal member constitutes a sleeve-shaped valve seat having an accommodating hole for said valve body, said valve body being elastically deformed with a depressing force to form an air passage between said valve body and said accommodating hole.

25. A physical protector according to claim 17, wherein said soft seal member constitutes a valve body including a base plate and having a substantially H-shaped vertical cross section, and said rigid seal member constitutes a sleeve-shaped valve seat having a tapered accommodating hole for said valve body, so that an air passage is formed between said base plate and said accommodating hole by sliding said valve body with a depressing force.

26. A physical protector according to claim 17, further comprising a pump portion which is disposed on one part of said soft seal member so as exert pressure to fluid flowing through an air passage.

27. A physical protector according to claim 16, further comprising a waterproof cover is disposed on one part of said seal members.

28. A physical protector comprising gas-barrier seal members different in deformability; a valve which is opened by exerting a pushing force to said seal members to elastically deform said seal members and closed by releasing the pushing force to resume the original shape of said seal members; and a flat bag member capable of being attached to a physical part, said bag member being formed by sheet-like gas-barrier membranes, stuffed with an expandable member in its compressed state, and provided with a reinforcing member for maintaining the expanded state of the bag member, said valve being mounted onto said bag member so as to open or close said bag member, said bag member being provided with a oscillator for imparting stimulation.

29. A physical protector comprising gas-barrier seal members different in deformability; valve (a) which is opened by exerting a pushing force to said seal members to elastically deform said seal members and closed by releasing the pushing force to resume original shape of said seal members; and a flat bag member capable of being attached to a physical part, said bag member being formed by sheet-like gas-barrier membranes, said valve being mounted onto said bag member and so as to open or close said bag member, said bag member being provided with a deformation-retaining part which is deformed into a fixed shape under a body temperature.

30. A physical protector comprising gas-barrier seal members different in deformability; valve (a) which is opened by exerting a pushing force to said seal members to elastically deform said seal members and closed by releasing the pushing force to resume the original shape of said seal members; and a flat bag member capable of being attached to a physical part, said bag member being formed by sheet-like gas-barrier membranes and stuffed with an expandable member in its compressed state, said valve being mounted onto said bag member so as to open or close said bag member, said bag member being provided with a deformation-retaining part which is deformed into a fixed shape under body temperature.

31. A physical protector comprising gas-barrier seal members different in deformability; valve (a) which is opened by exerting a pushing force to said seal members to elastically deform said seal members and closed by releasing the pushing force to resume an original shape of said seal members; and a flat bag member capable of being attached to a physical part, said bag member being formed by sheet-like gas-barrier membranes, stuffed with an expandable member in its compressed state, and provided with a reinforcing member for maintaining the expanded state of the bag member, said valve being mounted onto said bag member so as to open or close said bag member and, said bag member being provided with a deformation-retaining part which is deformed into a fixed shape under body temperature.

32. A physical protector, comprising:

a bag member formed by gas barrier membranes, said bag member having an opening;

deformable gas-barrier seal members, each having at least one vent hole, attached to said bag member at said opening; and said seal members forming a valve and having a structure such that said valve can be opened by exerting a pushing force to said seal members, when in an original shape, so as to elastically deform said seal members, and closed by releasing the pushing force such that said seal members resume said original shape.

33. A physical protector according to claim 32 wherein said seal members comprise a soft seal member and a rigid seal member.

34. A physical protector according to claim 33, wherein said soft seal member is formed of a film, and said rigid seal member is formed of a sheet having a desired thickness, and said seal members are provided at different positions with vent holes and kept in intimate face contact with each other in a normal state.

35. A physical protector according to claim 34, wherein said rigid seal member is formed in a spherical shape having a central protrusion capable of being elastically deformed, and said soft seal member is placed on said rigid seal member in layers so as to be in intimate contact with the spherical surface of said rigid seal member.

36. A physical protector according to claim 34, wherein said soft seal member is provided in its central portion with a vent hole, and said rigid seal member is provided in its peripheral portion with vent holes.

37. A physical protector according to claim 34, wherein said soft seal member has elongated vent holes each extending from a center toward a side peripheral portion thereof, and said rigid seal member has a vent hole at a position deviating from said vent holes in said soft seal member.

38. A physical protector according to claim 35, wherein said rigid seal member is provided with a support column extending downward from a center of a lower surface of said rigid seal member.

39. A physical protector according to claim 33, wherein said soft seal member constitutes a valve body having a substantially H-shaped vertical cross section, and said rigid seal member constitutes a sleeve-shaped valve seat having an accommodating hole for said valve body, said valve body being elastically deformed with a depressing force to form an air passage between said valve body and said accommodating hole.

40. A physical protector according to claim 33, wherein said rigid seal member constitutes a valve body having a substantially H-shaped vertical cross section, and said soft seal member constitutes a sleeve-shaped valve seat having an accommodating hole for said valve body, said valve body being elastically deformed with a depressing force to form an air passage between said valve body and said accommodating hole.

41. A physical protector according to claim 33, wherein said soft seal member constitutes a valve body including a base plate and having a substantially H-shaped vertical cross section, and said rigid seal member constitutes a sleeve-shaped valve seat having a tapered accommodating hole for said valve body, so that an air passage is formed between said base plate and said accommodating hole by sliding said valve body with a depressing force.

42. A physical protector according to claim 33, further comprising a pump portion which is disposed on one part of said soft seal member so as to exert pressure to fluid flowing through an air passage.

43. A physical protector according to claim 33, further comprising a waterproof cover disposed on one part of said seal members.

* * * * *